(12) United States Patent
Su et al.

(10) Patent No.: US 10,421,768 B2
(45) Date of Patent: Sep. 24, 2019

(54) METHOD OF BIOTRANSFORMATION OF BENZOPYRONE COMPOUNDS INTO THE CORRESPONDING PHOSPHATE-CONJUGATED DERIVATIVES

(71) Applicant: National Taiwan University, Taipei (TW)

(72) Inventors: Nan-Wei Su, Taipei (TW); Chen Hsu, Taipei (TW); Shang-Ta Wang, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 11 days.

(21) Appl. No.: 15/496,534

(22) Filed: Apr. 25, 2017

(65) Prior Publication Data
US 2017/0305944 A1 Oct. 26, 2017

(30) Foreign Application Priority Data

Apr. 25, 2016 (TW) .............................. 105112812 A

(51) Int. Cl.
C12P 17/06 (2006.01)
C12N 9/12 (2006.01)
C07F 9/6558 (2006.01)
C07F 9/655 (2006.01)
C12P 17/02 (2006.01)

(52) U.S. Cl.
CPC ...... C07F 9/65586 (2013.01); C07F 9/65522 (2013.01); C12N 9/1294 (2013.01); C12P 17/06 (2013.01); C12Y 207/09 (2013.01)

(58) Field of Classification Search
CPC .. C12P 19/32; C12P 19/40; C12P 7/00; C12N 15/63; C12N 9/22
USPC .................. 435/105, 128, 108, 252.2, 320.1; 504/105, 136, 227
See application file for complete search history.

(56) References Cited

PUBLICATIONS

Kisselev L., Structure, 2002, vol. 10: pp. 8-9.*
Kwiatkowski et al., Biochemistry 1999; vol. 38:pp. 11643-11650.*
Quarterly Reviews of Biophysics 2003, vol. 36 (3): pp. 307-340.*
Davos et al., Proteins: Structure, Function and Genetics, 2000, vol. 41: pp. 98-107.*

* cited by examiner

Primary Examiner — Robert B Mondesi
Assistant Examiner — Mohammad Y Meah
(74) Attorney, Agent, or Firm — Muncy, Geissler, Olds & Lowe, P.C.

(57) ABSTRACT

The present invention is related to a biotransformation process, effected by means of an isolated polypeptide possessing benzopyrone phosphate synthetase activity, and also a microorganism comprising a nucleic acid sequence that encodes the polypeptide, for the preparation of phosphate-conjugated derivatives of benzopyrone compounds. The hydrophilic property of the benzopyrone compounds is enhanced after catalyzed by the benzopyrone phosphate synthetase of the present invention.

5 Claims, 28 Drawing Sheets
Specification includes a Sequence Listing.

METHOD OF BIOTRANSFORMATION OF BENZOPYRONE COMPOUNDS INTO THE CORRESPONDING PHOSPHATE-CONJUGATED DERIVATIVES

BACKGROUND OF THE INVENTION

1. Technical Field

The present invention is related to a biotransformation process, effected by means of an isolated polypeptide possessing benzopyrone phosphate synthetase activity, and also a microorganism comprising a nucleic acid sequence that encodes the polypeptide, for the preparation of phosphate-conjugated derivatives of benzopyrone compounds.

2. Description of Related Art

Benzopyrone exists extensively in nature products and refers to either of two ketone derivatives of benzopyran, namely chromone (1-benzopyran-4-one) and coumarin (1-benzopyran-2-one), according to the different positions of double bound and carbonyl group in the heterocyclic pyrone ring. Benzopyrone contains the core skeleton of mostly flavonoid compounds. Flavonoid is considered a large category of natural products that derive from pyrones. All flavonoid compounds, which are derived from either 2-phenylbenzopyrone or 3-phenylbenzopyrone, can be classified into 10 groups: chalcones, flavanones, flavones, flavonols, anthocyanidins (flavylium cations), flavan 3-ols (catechins), flavan 3,4-diols (proanthocyanidins), biflavonoids and oligomeric flavonoids, isoflavonoids, and the aurones. So far, over 7000 compounds of flavonoids have been discovered and most of them are in fruits, legumes or other plant foods. They have caught medical society's attention and been extensively studied in recent years because of their physiological activity and pharmacological effects to human beings, such as anti-oxidation, anti-inflammatory, inhibition of cancer cell activity, prevention of cardiovascular diseases, and other health effects.

Isoflavones, a type of naturally occurring isoflavonoids, is produced almost exclusively by the members of the Fabaceae family, particularly soybeans. Isoflavones are regarded as phytoestrogens in mammals due to their structural similarity to 17β-estradiol, a type of human estrogen. Currently, there are 12 species of known soy isoflaveones, including: aglyconic forms of genistein, daidzein, and glycitein; and their glucosidic form, acetylglucosidic form and malonylglucosidic form. Among them, aglycone has been considered as the one with the best physiological activity. Therefore, many studies have devoted to the transformation of isoflavones in glycosylated form to aglycone form by de-glycosylation. In recent years, many studies have shown that daidzein and genistein (aglycone form of soy isoflavone) can deliver their postively physiological activities in osteoporosis, cardiovascular diseases, breast cancer and prostate cancer.

However, according to Merck Index, both daidzein and genistein are practically insoluble in water. Moreover, based on the Biopharmaceutical Classification System (BCS), a guide for predicting the intestinal drug absorption provided by the U.S. Food and Drug Administration, in the descriptions by Waldmann et al., 2012, both daidzein and genistein were categorized into BCS class IV chemicals. It means they are not easily physiologically absorbed because of their low aqueous solubility, low gastrointestinal permeability and, consequently, low bioavailability. Therefore, if the water solubilities of daidzein and genistein can be increased, their bioavailabilities can also be improved. Several studies reported improved the solubility of aglyconic isoflavones by chemical modification, enzymatic and microbial conversion to transform the structures of isoflavones to increase their water solubility. The derivatives transformed from isoflavones are, for instance, diisopropyl genistein-7-yl phosphate, daidzein-7-O-sulfate, daidzein-7-O-triglucoside, 2'-hydroxy genistein, 6-hydroxy genistein, and 8-hydroxy genistein, which have higher water solubility than that of aglyconic form of isoflavones.

BRIEF SUMMARY OF THE INVENTION

Until now, literature regarding microbials and/or their relevant enzyme mediated phosphorylation of benzopyrone chemicals has not been reported yet. Thus, the present invention provides a novel biological conversion model involving phosphorylation of benzopyrone chemicals. This invention provides a method for producing benzopyrone phosphate derivatives, comprising: using (1) an isolated polypeptide which is a benzopyrone phosphate synthetase, comprising the following amino acid sequences (a), (b), and (c) sequentially: (a) an amino acid sequence of ATP binding domain; (b) an amino acid sequence of substrate binding domain having at least 40% identical to an amino acid sequence of SEQ ID NO: 1, or an amino acid sequence of substrate binding domain having one or several amino acid have been deleted, substituted, inserted, and/or added in the amino acid sequence of SEQ ID NO: 1; and (c) an amino acid sequence of mobile catalyzing domain; or (2) a microorganism having a nucleic acid sequence encoding the said isolated polypeptide, to contact or to cultivate with a benzopyrone compound.

Preferably, the benzopyrone phosphate synthetase catalyzes phosphorylation of a benzopyrone compound.

Preferably, the amino acid sequence of the ATP binding domain is SEQ ID NO: 2.

Preferably, the amino acid sequence of the mobile catalyzing domain is SEQ ID NO: 3.

Preferably, the benzopyrone compound is selected from the group consisting of the following formula (I), (II), (III), (IV), and (V):

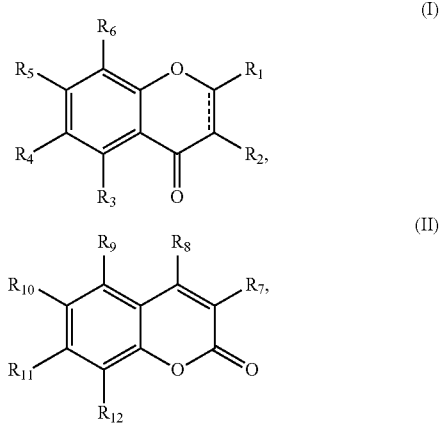

-continued (III)

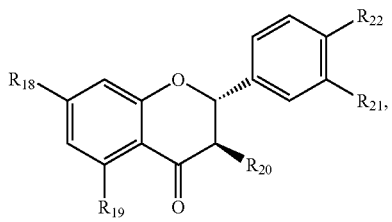

(IV)

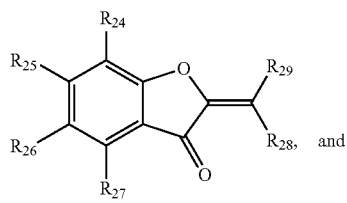

(V)

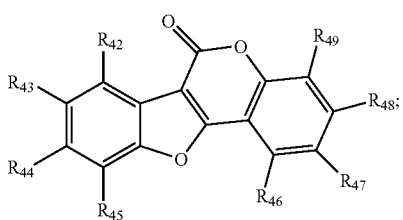

wherein $R_1$ and $R_2$ are independently selected from H, OH,

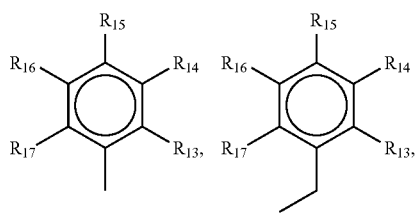

or $R_1$ and $R_2$ are fused to form $C_3$-$C_6$ cycloalkyl or $C_6$-$C_{10}$ aryl group;
$R_3$, $R_4$, $R_6$, $R_9$, $R_{10}$, $R_{12}$, $R_{15}$, and $R_{16}$ are H, OH, or $OCH_3$;
$R_5$ and $R_{11}$ are OH;
$R_7$ and $R_8$ are independently selected from H, OH, $OCH_3$, or $R_7$ and $R_8$ are fused to form $C_3$-$C_6$ cycloalkyl or $C_6$-$C_{10}$ aryl group, and optionally substituted by OH;
$R_{13}$ and $R_{14}$ are independently selected from H, OH, $OCH_3$, or

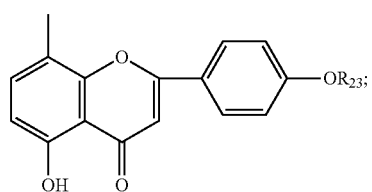

$R_{21}$ and $R_{22}$ are independently selected from hydrogen atom, halogen atom, nitro group, ($C_1$-$C_6$)alkyl, ($C_1$-$C_6$)alkyl-COOH, ($C_1$-$C_6$)alkylCOONa, trifluoro($C_1$-$C_6$)alkyl, ($C_3$-$C_6$)cycloalkyl, acyl, ($C_2$-$C_6$)alkenyl, ($C_2$-$C_6$)alkynyl, ($C_6$-$C_{18}$)aryl, ($C_6$-$C_{18}$)arylCOOH, ($C_6$-$C_{18}$)arylCOONa, ($C_6$-$C_{18}$)aryl($C_1$-$C_4$)alkyl, ($C_1$-$C_6$)alkyl($C_6$-$C_{18}$)aryl, ($C_5$-$C_{18}$)heteroaryl containing 1 to 3 heteroatoms, CH(OH)($C_6$-$C_{18}$)aryl, CO($C_6$-$C_{18}$)aryl, $(CH_2)_n$CONH—$(CH_2)_m$—($C_6$-$C_{18}$)aryl, $(CH_2)_n$$SO_2$NH—$(CH_2)_m$—($C_6$-$C_{18}$)aryl or $(CH_2)_n$CONH—CH(COOH)—$(CH_2)_p$—($C_6$-$C_{18}$)aryl group, wherein n is 1 to 4, m is 0 to 3 and p is 0 to 2, or $OR_x$, $SR_x$, $NR_xR_y$, wherein (i) $R_x$ and $R_y$, independent of each other, are chosen from a hydrogen atom and ($C_1$-$C_6$)alkyl, ($C_3$-$C_6$)cycloalkyl, ($C_6$-$C_{18}$)aryl, ($C_6$-$C_{18}$)aryl($C_1$-$C_4$)alkyl, ($C_1$-$C_{12}$)alkyl($C_6$-$C_{18}$)aryl, ($C_3$-$C_6$)cyclo-alkyl($C_6$-$C_{12}$)aryl, ($C_5$-$C_{12}$)heteroaryl containing 1 to 3 heteroatoms, NR'R" and NHCOR'R" groups, where in R' and R", independent of each other, are chosen from a hydrogen atom and ($C_1$-$C_6$)alkyl, ($C_3$-$C_6$)cycloalkyl and ($C_6$-$C_{12}$)aryl groups, and aromatic or non-aromatic ($C_5$-$C_{12}$)heterocycles, containing 1 to 3 heteroatoms, or (ii) $R_x$ and $R_y$ together form a linear or branched hydrocarbon-based chain containing 2 to 6 carbon atoms, optionally comprising one or more double bonds and/or optionally include an oxygen, sulfur or nitrogen atom;
$R_{23}$ is H or $CH_3$; ═ is a single bond or a double bond;
$R_{24}$, $R_{26}$, and $R_{27}$ are independently selected from H, ($C_1$-$C_5$)alkyl, hydroxyl, $OR_{30}$, $OCH_2OR_{31}$, $OCOR_{32}$, $COR_{33}$, $CO_2R_{34}$, $OCH_2COOR_{35}$, $OCH_2(OR_{36})_2$, OC═$ONHR_{37}$, halogen, nitro, amino, $NR_{38}R_{39}$, cyano, mercapto, $SR_{40}$, $S(O)_qR_{41}$, ($C_1$-$C_5$)chloroalkyl, ($C_1$-$C_5$)haloalkoxy, ($C_2$-$C_6$)alkenyl, ($C_2$-$C_6$)alkynyl, ($C_3$-$C_{10}$)Cycloalkyl, ($C_6$-$C_{11}$)phenyl, or ($C_7$-$C_{12}$)benzyl, wherein q is an integral of 1 to 3;
$R_{25}$ is OH;
$R_{28}$ is H, ($C_1$-$C_3$)alkyl, ($C_1$-$C_3$)alkoxy, ($C_1$-$C_3$)chloroalkoxy, halogen, nitro, amino, cyano, mercapto, or hydroxyl;
$R_{29}$ is five member ring or six member ring, including benzene, pyridine, furan, thiophene, pyrrole, thiazole, pyridazine, or pyrimidine;
$R_{42}$, $R_{44}$, $R_{45}$, $R_{46}$, $R_{47}$, and $R_{49}$ are independently selected from H, ($C_1$-$C_5$)alkyl, hydroxyl, $OR_{30}$, $OCH_2OR_{31}$, $OCOR_{32}$, $COR_{33}$, $CO_2R_{34}$, $OCH_2COOR_{35}$, $OCH_2(OR_{36})_2$, OC═$ONHR_{37}$, halogen, nitro, amino, $NR_{38}R_{39}$, cyano, mercapto, $SR_{40}$, $S(O)_rR_{41}$, ($C_1$-$C_5$)chloroalkyl, ($C_1$-$C_5$)haloalkoxy, ($C_2$-$C_6$)alkenyl, ($C_2$-$C_6$)alkynyl, ($C_3$-$C_{10}$)Cycloalkyl, ($C_6$-$C_{11}$)phenyl, or ($C_7$-$C_{12}$)benzyl, wherein r is an integral of 1 to 3;
$R_{43}$ and $R_{48}$ are OH;
$R_{30}$ and $R_{31}$ are independently selected from ($C_1$-$C_5$)alkyl, ($C_1$-$C_5$)haloalkyl, ($C_2$-$C_6$)alkenyl, ($C_2$-$C_6$)alkynyl, ($C_6$-$C_{11}$)phenyl, or ($C_7$-$C_{12}$)benzyl;
$R_{32}$ is ($C_1$-$C_5$)alkyl, ($C_1$-$C_5$)haloalkyl, ($C_6$-$C_{11}$)phenyl, or ($C_7$-$C_{12}$)benzyl;
$R_{33}$ is ($C_1$-$C_5$)alkyl, ($C_1$-$C_5$)haloalkyl, ($C_2$-$C_6$)alkenyl, ($C_2$-$C_6$)alkynyl, ($C_6$-$C_{11}$)phenyl, or ($C_7$-$C_{12}$)benzyl;
$R_{34}$, $R_{35}$, $R_{36}$ and $R_{37}$ are independently selected from ($C_1$-$C_5$)alkyl or ($C_1$-$C_5$)haloalkyl;
$R_{38}$ and $R_{39}$ are independently selected from H, ($C_1$-$C_5$)alkyl or ($C_1$-$C_5$)haloalkyl, wherein only one of $R_{38}$ and $R_{39}$ is H; and,
$R_{40}$ and $R_{41}$ are independently selected from ($C_1$-$C_5$)alkyl or ($C_1$-$C_5$)haloalkyl.

Preferably, the benzopyrone compound is flavonol, flavone, flavanone, flavonoids lignans, isoflavones, or coumarin.

Preferably, the microorganism is derived from *Bacillus*.
Preferably, the microorganism is *Bacillus subtilis*.

In the present invention, the isolated benzopyrone phosphate synthetase can phosphorylate benzopyrone compounds, especially flavone compounds, such as isoflavone, flavone, flavonol, and flavanone, and coumarins. This can improve water solubility, enhance bioavailability and demonstrate advantageous bioactivity of benzopyrone compounds.

BRIEF DESCRIPTION OF DRAWINGS

FIG. 2a is the HPLC chromatograms of the reaction of genistein and benzopyrone phosphate synthetase under the reaction times of 2a 0 min, 2b 15 min, 2c 30 min, 2d 60 min, 2e 90 min, and 2f 120 min; FIG. 2g is the concentration changing curves over the reaction time for genistein and the benzopyrone phosphate synthetase.

FIG. 3a is the HPLC-UV/Vis (254 nm) chromatograms of genistein, genistein-7-O-phosphate, and genistein-4'-O-phosphate before and after the reaction (40° C., pH 7.8, 1 h); FIG. 3b is the ESI-MS spectrum of parent ion and fragment ion of genistein-7-O-phosphate; FIG. 3c is the ESI-MS spectrum of parent ion and fragment ion of genistein-4'-O-phosphate.

FIG. 4a is the HPLC-UV/Vis (254 nm) chromatograms of daidzein, daidzein-7-O-phosphate, and daidzein-4'-O-phosphate before and after the reaction (40° C., pH 7.8, 1 h); FIG. 4b is the ESI-MS spectrum of parent ion and fragment ion of daidzein-7-O-phosphate; FIG. 4c is the ESI-MS spectrum of parent ion and fragment ion of daidzein-4'-O-phosphate.

FIG. 5a is the HPLC-UV/Vis (270 nm) chromatograms of apigenin, apigenin-7-O-phosphate, and apigenin-4'-O-phosphate before and after the reaction (40° C., pH 7.8, 1 h); FIG. 5b is the UV-Visible absorption spectrum and the ESI-MS spectrum of parent ion and fragment ion of apigenin; FIG. 5c is the UV-Visible absorption spectrum and the ESI-MS spectrum of parent ion and fragment ion of apigenin-7-O-phosphate; FIG. 5d is the UV-Visible absorption spectrum and the ESI-MS spectrum of parent ion and fragment ion of apigenin-4'-O-phosphate.

FIG. 6a is the HPLC-UV/Vis (270 nm) chromatograms of 6-hydroxyflavone and flavone-6-O-phosphate before and after the reaction (40° C., pH 7.8, 1 h); FIG. 6b is the UV-Visible absorption spectrum and the ESI-MS spectrum of parent ion and fragment ion of 6-hydroxyflavone; FIG. 6c is the UV-Visible absorption spectrum and the ESI-MS spectrum of parent ion and fragment ion of flavone-6-O-phosphate.

FIG. 7a is the HPLC-UV/Vis (360 nm) chromatograms of kaempferol, kaempferol-7-O-phosphate, and kaempferol-4'-O-phosphate before and after the reaction (40° C., pH 7.8, 1 h); FIG. 7b is the UV-Visible absorption spectrum and the ESI-MS spectrum of parent ion and fragment ion of kaempferol; FIG. 7c is the UV-Visible absorption spectrum and the ESI-MS spectrum of parent ion and fragment ion of kaempferol-7-O-phosphate.

FIG. 8a is the HPLC-UV/Vis (360 nm) chromatograms of quercetin, quercetin-7-O-phosphate, and quercetin-4'-O-phosphate before and after the reaction (40° C., pH 7.8, 1 h); FIG. 8b is the UV-Visible absorption spectrum and the ESI-MS spectrum of parent ion and fragment ion of quercetin; FIG. 8c is the UV-Visible absorption spectrum and the ESI-MS spectrum of parent ion and fragment ion of quercetin-7-O-phosphate.

FIG. 9a is the HPLC-UV/Vis (285 nm) chromatograms of naringenin, naringenin-7-O-phosphate, and naringenin-4'-O-phosphate before and after the reaction (40° C., pH 7.8, 1 h); FIG. 9b is the UV-Visible absorption spectrum and the ESI-MS spectrum of parent ion and fragment ion of naringenin; FIG. 9c is the UV-Visible absorption spectrum and the ESI-MS spectrum of parent ion and fragment ion of naringenin-7-O-phosphate.

FIG. 10a is the HPLC-UV/Vis (285 nm) chromatograms of hesperetin, hesperetin-7-O-phosphate, and hesperetin-4'-O-phosphate before and after the reaction (40° C., pH 7.8, 1 h); FIG. 10b is the UV-Visible absorption spectrum and the ESI-MS spectrum of parent ion and fragment ion of hesperetin; FIG. 10c is the E UV-Visible absorption spectrum and the ESI-MS spectrum of parent ion and fragment ion of hesperetin-7-O-phosphate; FIG. 10d is the UV-Visible absorption spectrum and the ESI-MS spectrum of parent ion and fragment ion of hesperetin-4'-O-phosphate.

FIG. 11a is the HPLC-UV/Vis (280 nm) chromatograms of urolithin A, urolithin A-6-O-phosphate, and urolithin A-8-O-phosphate before and after the reaction (40° C., pH 7.8, 1 h); FIG. 11b is the UV-Visible absorption spectrum of urolithin A; FIG. 11c is the UV-Visible absorption spectrum of urolithin A-6-O-phosphate; FIG. 11d is the UV-Visible absorption spectrum of urolithin A-8-O-phosphate.

FIG. 12a is the HPLC-UV/Vis (287 nm) chromatograms of silibinin and silibinin-7-O-phosphate before and after the reaction (40° C., pH 7.8, 1 h); FIG. 12b is the UV-Visible absorption spectrum of silibinin; FIG. 12c is the UV-Visible absorption spectrum of silibinin-7-O-phosphate.

DETAILED DESCRIPTION OF THE INVENTION

Isolated Polypeptides of the Present Invention

The main objective of the present invention is to provide an isolated polypeptide, comprising the following amino acid sequences (a), (b), and (c) sequentially: (a) an amino acid sequence of ATP binding domain; (b) an amino acid sequence of substrate binding domain having at least 40% identical to an amino acid sequence of SEQ ID NO: 1, or an amino acid sequence of substrate binding domain having one or several amino acid have been deleted, substituted, inserted, and/or added in the amino acid sequence of SEQ ID NO: 1; and (c) an amino acid sequence of mobile catalyzing domain; wherein the polypeptide has the activity of benzopyrone phosphate synthetase.

Figure 1A:
FIG. 1a is the schematic diagram of the functional domain arrangement of the polypeptide classified in EC 2.7.9 according to biochemical characteristic.
Figure 1B:
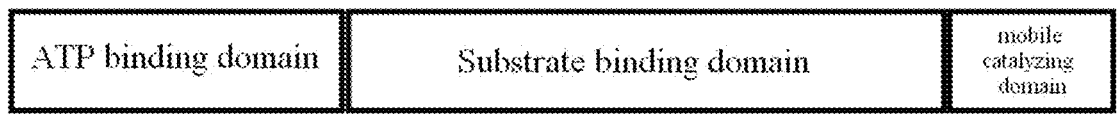
FIG. 1b is the schematic diagram of the functional domain arrangement of the polypeptide of the present invention.

In general, polypeptide classified in EC 2.7.9 according to the biochemical characteristic, is conventionally having a sequential order of ATP binding domain, mobile catalyzing domain, and substrate binding domain, as shown in FIG. 1a. However, the inventor of the present invention found that the functional domain architecture of isolated polypeptide of the present invention having a different order to those classified in EC 2.7.9.1 or EC 2.7.9.2; namely, the isolated polypeptide of the present invention having substrate binding domain located prior to the mobile catalyzing domain. In addition, the substrate being phosphorylated by the enzyme classified in EC 2.7.9 is completely different to that of the isolated polypeptide of the present invention. Furthermore, the ATP binding domain and the mobile catalyzing domain are generally conservative in the amino acid sequences without extensive variation when alignment of homologous protein or polypeptide. The aforementioned (a) amino acid sequence of ATP binding domain is preferably SEQ ID NO: 2, and the aforementioned (c) amino acid sequence of mobile catalyzing domain is preferably SEQ ID NO: 3.

In the present invention, "identity" of the amino acid sequences means the degree of exactly matching between two amino acid sequences; "similarity" of the amino acid sequences means the degree of resemblance and/or conservation between two sequences. It is known to the ordinary person in the art that there are only partial segments of amino acid sequences have functionality, called "functional domain", in long chain amino acid sequences of polypeptides and protein. When two different polypeptides or proteins have the same functional domain they share the same function. In general, when the identity of the amino acid sequences of the polypeptides and proteins are at least 40%, they share the same function (referring to "How Protein Work", Williamson, 2011). After alignment of homologous protein or polypeptide, the aforementioned (b) amino acid sequence of substrate binding domain has at least 40% amino acid sequence identity with SEQ ID NO: 1, preferably at least 45%, more preferably at least 50%, and most preferably 55%.

In the present invention, the amino acid sequence alignment for obtaining the identity can be any conventional amino acid sequence alignment tool, and the sequence alignment algorithms includes Needle-Wunsch algorithm, Smith-Waterman algorithm, or Karling & Altschul algorithm, but is not limited thereto; the amino acid sequence alignment tool includes BLAST (Basic Local Alignment Search Tool), BLAT (BLAST-like Alignment Tool), Grapped BLAST or FASTA, but is not limited thereto.

The aforementioned (b) substrate binding domain "having at least 40% identical to an amino acid sequence of SEQ ID NO: 1 or having one or more amino acid have been deleted, substituted, inserted, and/or added in the amino acid sequence of SEQ ID NO: 1" means that, without loss of functionality of the (b) substrate binding domain, there is one or more amino acid being deleted, substituted, inserted, and/or added in the amino acid sequence of SEQ ID NO: 1 by any conventional mutagenesis method, such as site-directed mutagenesis, and the number of amino acids has no limitation.

The aforementioned benzopyrone phosphate synthetase activity is predicted to have the following mechanism for phosphorylation of the benzopyrone compound:

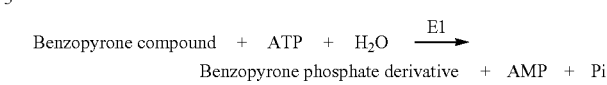

Benzopyrone compound + ATP + H$_2$O $\xrightarrow{E1}$ Benzopyrone phosphate derivative + AMP + Pi E1: benzopyrone phosphate synthetase The optimal temperature and pH for the activity of the purified benzopyrone phosphate synthetase are 30° C. to 50° C. and pH 6.5 to pH 8.5, respectively, and the most preferable temperature and pH is 40° C. and pH 7.5, respectively. Under pH 7.5, the relative activity of benzopyrone phosphate synthetase at 30° C. and 50° C. is about 26% and 8% of its activity determined at 40° C. In addition, about 37% and 42% of the relative activity at 40° C. is retained at pH 6.5 and 8.5, respectively. However, the relative activity dropped markedly to only about 5% at pH 5.5. This point would be critical in practical use. The benzopyrone phosphate synthetase is stable at pH 7-8 and at temperatures below 40° C. After incubation at 40° C. and pH 7.5 for 1 h, benzopyrone phosphate synthetase still retained about 85% of its original activity.

The benzopyone phosphate synthetase mentioned above maintains a relatively stable activity within neutral to slightly alkaline environment (pH 7-8). Comparison to react at pH 7, the enzyme reveals 88% of activity at pH 7.8, and the enzyme activity drops to 42% and 37% at pH 8.5 and pH 6.5, respectively. When the pH is at 5.5, the enzyme loses its reaction activity. Thus, the preferable environment for benzopyrone phosphate synthetase is neutral to slightly alkaline condition, preferable pH 7 to 8, more preferable pH 7.5.

The aforementioned benzopyrone compound is selected from the group consisting of the following formula (I) to (V):

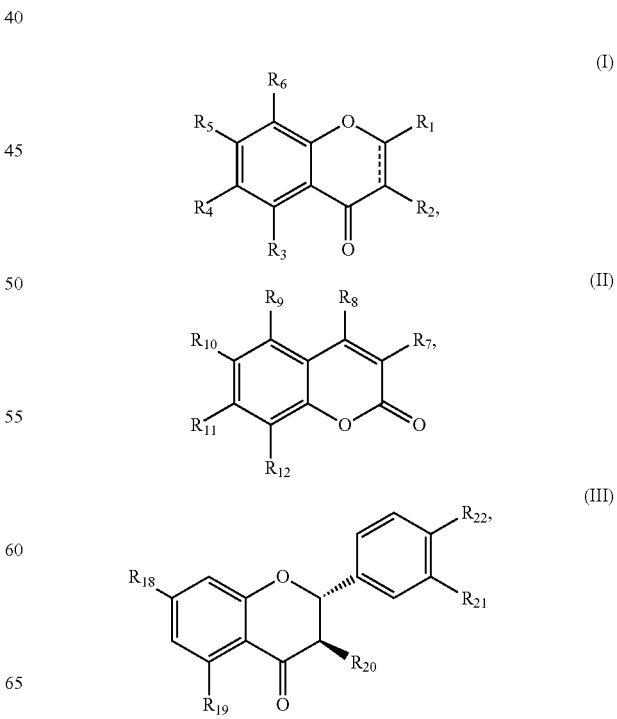

-continued

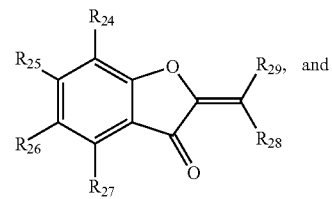
(IV)

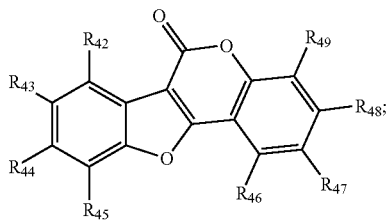
(V)

wherein $R_1$ and $R_2$ are independently selected from H, OH,

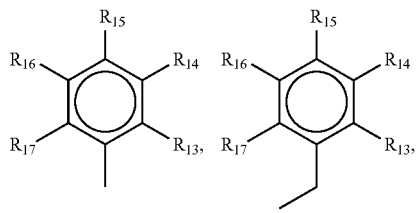

or $R_1$ and $R_2$ are fused to form $C_3$-$C_6$ cycloalkyl or $C_6$-$C_{10}$ aryl group;

$R_3$, $R_4$, $R_6$, $R_9$, $R_{10}$, $R_{12}$, $R_{15}$, and $R_{16}$ are H, OH, or $OCH_3$;

$R_5$ and $R_{11}$ are OH;

$R_7$ and $R_8$ are independently selected from H, OH, $OCH_3$, or $R_7$ and $R_8$ are fused to form $C_3$-$C_6$ cycloalkyl or $C_6$-$C_{10}$ aryl group, and optionally substituted by OH;

$R_{13}$ and $R_{14}$ are independently selected from H, OH, $OCH_3$, or

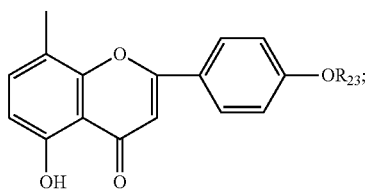

$R_{21}$ and $R_{22}$ are independently selected from hydrogen atom, halogen atom, nitro group, $(C_1$-$C_6)$alkyl, $(C_1$-$C_6)$alkyl-COOH, $(C_1$-$C_6)$alkylCOONa, trifluoro$(C_1$-$C_6)$alkyl, $(C_3$-$C_6)$cycloalkyl, acyl, $(C_2$-$C_6)$alkenyl, $(C_2$-$C_6)$alkynyl, $(C_6$-$C_{18})$aryl, $(C_6$-$C_{18})$arylCOOH, $(C_6$-$C_{18})$arylCOONa, $(C_6$-$C_{18})$aryl$(C_1$-$C_4)$alkyl, $(C_1$-$C_6)$alkyl$(C_6$-$C_{18})$aryl, $(C_5$-$C_{18})$ heteroaryl containing 1 to 3 heteroatoms, CH(OH)$(C_6$-$C_{18})$ aryl, CO$(C_6$-$C_{18})$aryl, $(CH_2)_n$CONH—$(CH_2)_n$—$(C_6$-$C_{18})$ aryl, $(CH_2)_n$SO$_2$NH—$(CH_2)_m$—$(C_6$-$C_{18})$aryl or $(CH_2)_n$CONH—CH(COOH)—$(CH_2)_p$—$(C_6$-$C_{18})$ar.

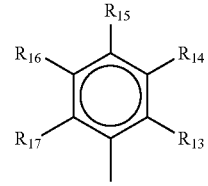

n is 1 to 4, m is 0 to 3 and p is 0 to 2, or $OR_x$, $SR_x$, $NR_xR_y$, wherein (i) pendent of each other, are chosen from a hydrogen atom and $(C_1$-$C_6)$alkyl, $(C_3$-$C_6)$cycloalkyl, $(C_6$-$C_{18})$aryl, $(C_6$-$C_{18})$aryl$(C_1$-$C_4)$alkyl, $(C_1$-$C_{12})$alkyl$(C_6$-$C_{18})$ aryl, $(C_3$-$C_6)$cyclo-alkyl$(C_6$-$C_{12})$aryl, $(C_5$-$C_{12})$heteroaryl containing 1 to 3 heteroatoms, NR'R" and NHCOR'R" groups, where in R' and R", independent of each other, are chosen from a hydrogen atom and $(C_1$-$C_6)$alkyl, $(C_3$-$C_6)$ cycloalkyl and $(C_6$-$C_{12})$aryl groups, and aromatic or non-aromatic $(C_5$-$C_{12})$heterocycles, containing 1 to 3 heteroatoms, or (ii) $R_x$ and $R_y$ together form a linear or branched hydrocarbon-based chain containing 2 to 6 carbon atoms, optionally comprising one or more double bonds and/or optionally include an oxygen, sulfur or nitrogen atom;

$R_{23}$ is H or $CH_3$;

⸺ is a single bond or a double bond;

$R_{24}$, $R_{26}$, and $R_{27}$ are independently selected from H, $(C_1$-$C_5)$alkyl, hydroxyl, $OR_{30}$, $OCH_2OR_{31}$, $OCOR_{32}$, $COR_{33}$, $CO_2R_{34}$, $OCH_2COOR_{35}$, $OCH_2(OR_{36})_2$, OC=ONHR$_{37}$, halogen, nitro, amino, $NR_{38}R_{39}$, cyano, mercapto, $SR_{40}$, $S(O)_qR_{41}$, $(C_1$-$C_5)$chloroalkyl, $(C_1$-$C_5)$haloalkoxy, $(C_2$-$C_6)$ alkenyl, $(C_2$-$C_6)$alkynyl, $(C_3$-$C_{10})$cycloalkyl, $(C_6$-$C_{11})$phenyl, or $(C_7$-$C_{12})$benzyl, wherein q is an integral of 1 to 3;

$R_{25}$ is OH;

$R_{28}$ is H, $(C_1$-$C_3)$alkyl, $(C_1$-$C_3)$alkoxy, $(C_1$-$C_3)$chloroalkoxy, halogen, nitro, amino, cyano, mercapto, or hydroxyl;

$R_{29}$ is five member ring or six member ring, including benzene, pyridine, furan, thiophene, pyrrole, thiazole, pyridazine, or pyrimidine;

$R_{42}$, $R_{44}$, $R_{45}$, $R_{46}$, $R_{47}$, and $R_{49}$ are independently selected from H, $(C_1$-$C_5)$alkyl, hydroxyl, $OR_{30}$, $OCH_2OR_{31}$, $OCOR_{32}$, $COR_{33}$, $CO_2R_{34}$, $OCH_2COOR_{35}$, $OCH_2(OR_{36})_2$, OC=ONHR$_{37}$, halogen, nitro, amino, $NR_{38}R_{39}$, cyano, mercapto, $SR_{40}$, $S(O)_rR_{41}$, $(C_1$-$C_5)$chloroalkyl, $(C_1$-$C_5)$haloalkoxy, $(C_2$-$C_6)$alkenyl, $(C_2$-$C_6)$alkynyl, $(C_3$-$C_{10})$cycloalkyl, $(C_6$-$C_{11})$phenyl, or $(C_7$-$C_{12})$benzyl, wherein r is an integral of 1 to 3;

$R_{43}$ and $R_{48}$ are OH;

$R_{30}$ and $R_{31}$ are independently selected from $(C_1$-$C_5)$alkyl, $(C_1$-$C_5)$haloalkyl, $(C_2$-$C_6)$alkenyl, $(C_2$-$C_6)$alkynyl, $(C_6$-$C_{11})$ phenyl, or $(C_7$-$C_{12})$benzyl;

$R_{32}$ is $(C_1$-$C_5)$alkyl, $(C_1$-$C_5)$haloalkyl, $(C_6$-$C_{11})$phenyl, or $(C_7$-$C_{12})$benzyl;

$R_{33}$ is $(C_1$-$C_5)$alkyl, $(C_1$-$C_5)$haloalkyl, $(C_2$-$C_6)$alkenyl, $(C_2$-$C_6)$alkynyl, $(C_6$-$C_{11})$phenyl, or $(C_7$-$C_{12})$benzyl;

$R_{34}$, $R_{35}$, $R_{36}$ and $R_{37}$ are independently selected from $(C_1$-$C_5)$alkyl or $(C_1$-$C_5)$haloalkyl;

$R_{38}$ and $R_{39}$ are independently selected from H, $(C_1$-$C_5)$alkyl or $(C_1$-$C_5)$haloalkyl, wherein only one of $R_{38}$ and $R_{39}$ is H; and, $R_{40}$ and $R_{41}$ are independently selected from $(C_1$-$C_5)$alkyl or $(C_1$-$C_5)$haloalkyl.

The aforementioned benzopyrone compound is flavonol, flavone, flavanone, flavonoids lignans, isoflavone, or coumarin.

A Microorganism Comprising the Nucleic Acid Sequence Encoding the Isolate Polypeptide of the Present Invention Another main objective of the present invention is to provide a microorganism, comprising a nucleic acid sequence encoding the aforementioned polypeptide of the present invention that has the benzopyrone phosphate synthetase activity.

The aforementioned nucleic acid sequence is derived from Bacillus, preferably Bacillus subtilis var. natto, Bacillus subtilis, Bacillus tequilensis, Bacillus vallismortis, Bacillus mojavensis, Bacillus atropharus, Bacillus amyloliquefaciens, Bacillus pumilus, or Bacillus megaterium, more preferably Bacillus subtilis var. natto. The aforementioned strains have homologues polypeptide with the benzopyrone phosphate synthetase activity. Using the substrate binding domain of the benzopyrone phosphate synthetase (amino acids 313 to 761) of Bacillus subtilis natto (i.e. SEQ ID NO: 1 of the present invention) for homology strain sequence alignment, the amino acids 305 to 753 of Bacillus subtilis (i.e. SEQ ID NO: 7) has 99% identity to SEQ ID NO: 1; the amino acids 305 to 753 of Bacillus tequilensis (i.e. SEQ ID NO: 8) has 88% identity to SEQ ID NO: 1; the amino acids 305 to 754 of Bacillus vallismortis (i.e. SEQ ID NO: 9) has 88% identity to SEQ ID NO: 1; the amino acids 305 to 753 of Bacillus mojavensis (i.e. SEQ ID NO: 10) has 85% identity to SEQ ID NO: 1; the amino acids 305 to 756 of Bacillus atropharus (i.e. SEQ ID NO: 11) has 70% identity to SEQ ID NO: 1; the amino acids 306 to 754 of Bacillus amyloliquefaciens (i.e. SEQ ID NO: 12) has 64% identity to SEQ ID NO: 1; the amino acids 293 to 762 of Bacillus pumilius (i.e. SEQ ID NO: 13) has 45% identity to SEQ ID NO: 1; and the amino acids 295 to 767 of Bacillus megaterium (i.e. SEQ ID NO: 14) has 42% identity to SEQ ID NO: 1.

The aforementioned microorganism can be any kind of microorganism obtained by genetic engineering or molecular biotechnology which can normally express the nucleic acid sequence encoding the aforementioned polypeptide (sequentially including ATP binding domain, substrate binding domain, and mobile catalyzing domain) after transferring or transplanting genetic materials.

The microorganism mentioned above can be genetically modified microorganisms which express the aforementioned nucleic acid sequence. The genetic modification includes genetic modification of organisms, which enhances or strengthens the production of polypeptides in the organism. The genetic modified organisms include bacteria, single-cell organisms, microalgae, fungi or other microorganisms. The genetic modified microorganisms contain a genome, which is modified from normal form, i.e., wild type or natural occurrence through genetic modification or mutation in order to accomplish the desired results, i.e., can produce benzopyrone phosphate synthetase of the present invention or have the benzopyrone phosphate synthetase activity of the present invention). Genetic modification of microorganisms can be achieved by typical strain development and/or molecular genetic techniques, which are known techniques commonly applied to microorganisms. The genetically modified microorganisms include microorganisms whose nucleic acids are genetically modified by insertion, deletion or other forms of modification such as mutation (e.g., insertion, deletion, substitution and/or inversion of nucleotides), so that such microorganism can provide desired effects.

The Method for Producing Benzopyrone Phosphate Derivatives of the Present Invention Another objective of the present invention is to provide a method for producing benzopyrone phosphate derivatives, which includes contact or cultivation of the isolated polypeptide or microorganisms mentioned above with a benzopyrone compounds. The preferable benzopyrone compounds have the structures defined in formula (I) to (V) as mentioned above.

After contact or cultivation with the isolated polypeptide or microorganisms in the present invention, benzopyrone compounds can be turned into benzopyrone phosphate derivatives. Comparing to the benzopyrone compounds without phosphorylation, the benzopyrone phosphate derivatives have higher absorption rate and bioavailability, and hence better biological activity. Thus, the benzopyrone phosphate derivatives can be used for manufacturing of food, pharmaceuticals, and industrial raw materials. The term "food," for example, includes food supplements, health supplements, functional supplements, baby food and geriatric food. The food can be in the form of solid, fluid, liquid, and mixture thereof, but preferably liquid. If the benzopyrone phosphate derivatives are used as pharmaceuticals, there is no particular limit to dosage form. They can be in any form, such as solution, paste, gel, solid and powder. The pharmaceuticals can also contain other pharmaceutically active ingredients (e.g., anti-inflammatory ingredients) or grants components (e.g., a lubricating composition, the carrier component).

EMBODIMENT EXAMPLE

[Preparation Example] Isolation and Purification of Benzopyrone Phosphate Synthetase from Bacillus subtilis The Bacillus subtilis natto strain (deposited in Bioresource Collection and Research Center of Food Industry Research Development Institute, numbered as BCRC 19679) was cultured at 37° C. for 12 h at NA nutrient agar plate. Single colony was removed and cultured in the NB medium at 37° C. and 150 rpm for 12 h. When the $OD_{600}$ was about 1.0 ($2\times10^8$ CFU/mL), it was used as an seed culture. 5% of seed culture was inoculated in 500 mL broth at 37° C. and 150 rpm for 24 h. When the $OD_{600}$ was about 3.5 ($3\times10^9$ CFU/mL), the broth was centrifuged. The pellets were washed twice by Tris-HCl buffer (pH 7.8) and stored at −20° C.

Isolation and Purification of Benzopyrone Phosphate Synthetase

1. Ammonium Sulfate Precipitation:

The pellet was re-suspended with cell lysis buffer (0.1 M Tris-HCl buffer, pH 7.8) containing protease inhibitors. The suspension was placed on ice for ultrasonic lysis for 20 min, followed by cold centrifuge, and the supernatant was collected as crude extract. Ammonia sulfate powder with different saturation percentage was slowly added to the 50 mL crude extract in accordance with the ammonium sulfate saturation percentage scale, and protein precipitates of 0-20%, 20-40%, 40-60%, 60-80%, 80-100%, and 100% saturation of ammonia sulfate were collected. The protein precipitates were back dissolved into 10 mL enzyme solution and dialyzed by Amicon Ultra-15 centrifuge tube (30,000 Da, MWCO) to remove the ammonia sulfate. Then, the protein was concentrated to 1 mL for the determination of enzyme activity. Most active enzyme was found in 40-60% saturation of ammonia sulfate.

2. DEAE FF Column for Anion Exchange Chromatography:

The dialyzed crude extracts were injected into DEAE FF column for anion exchange chromatography. The column was first washed over by 10 column volumes of 0.1 M Tris-HCl buffer (pH 7.8) to remove non-adsorbed protein, and then washed by 0.1, 0.2, and 0.5 M NaCl solution. The eluent was collected in a series of fractions for determination of protein content and enzyme activity. Active enzymes was concentrated in the eluent of 0.2 M NaCl-0.1 M Tris-HCl buffer (pH 7.8), which had specific activity of 3.0 unit/mg and the total amount of protein was 36 mg. The aforementioned active eluent was collected for the next step of purification.

3-1. First Q Anion Exchange Resin Chromatography:

The aforementioned active eluent from DEAE FF was dialyzed by centrifuge tubes for removal of NaCl and then injected into Q Sepharose HP column for anion exchange chromatography. The column was first washed over by 0.1 M Tris-HCl buffer (pH 7.8) for removal of non-adsorbed protein, and then washed by aforementioned buffer containing 0.1 to 0.3 M NaCl. The eluent was collected in a series of fractions for determination of protein content and enzyme activity. The eluent with the highest specific activity, 88.5 unit/mg, was collected and the total protein content was 0.38 mg.

3-2. Second Q Anion Exchange Resin Chromatography:

The aforementioned Q Sepharose HP eluent with the highest specific activity was dialyzed by the centrifuge tube for removal of NaCl and then injected into Q Sepharose HP column for second anion exchange chromatography. The column was first washed over by 0.1 M Tris-HCl buffer (pH 7.8) for removal of non-adsorbed protein, and then washed by aforementioned buffer containing 0.15 to 0.3 M NaCl. The eluent was collected in a series of fractions for determination of protein content and enzyme activity. The second anion exchange chromatography of Q Sepharose HP column narrowed the range of salt gradient, which allowed finer separation of proteins and thus the purity and specific activity were enhanced. The eluent with the highest specific activity, 103.9 unit/mg, was collected and the total protein content was 0.02 mg.

4. Pheyl Hydrophobic Chromatography:

The aforementioned eluent of the second Q Sepharose HP with highest specific activity was dialyzed by the centrifuge tubes for removal of NaCl, and then back dissolved in 1 M $(NH_4)_2SO_4$-0.1 M Tris-HCl (pH 7.8) buffer before injected into a Phenyl HP column for hydrophobic chromatography. The column was first washed over by 25 column volumes of the aforementioned buffer for removal of non-adsorbed protein, and then washed by 25 column volume of 0.1 M Tris-HCl (pH 7.8) buffer mentioned above to lower the ammonia sulfate concentration in the column. The eluent was collected in a series of fractions for determination of protein content and enzyme activity. The eluent with the highest specific activity, 120.9 unit/mg, was collected and the total protein content was 13.5 µg.

5. Superdex 75 Gel-Filtration Chromatography:

The aforementioned elution of the Phenyl HP with highest specific activity was dialyzed by the centrifuge tube for removal of ammonia sulfate and then back dissolved in 0.1 M Tris-HCl (pH 7.8) buffer before injected into a Superdex 75 column for gel-filtration chromatography. The eluent was collected in a series of fractions for determination of protein content and enzyme activity. The eluent with the highest specific activity, 127.7 unit/mg, was collected and the total protein content was 3.7 µg. Low molecular protein, as a standard reference, was injected into a Superdex 75 column and washed by the same wishing condition in order to obtain the linear relationship between molecular weight and washing time. Based on the linear relationship and extrapolation, we concluded that the molecular weight of the original form of benzopyrone phosphate synthetase is 90 kDa in the eluent with the highest specific activity.

6. SDS-PAGE Analysis:

The crude extract was analyzed by SDS-PAGE electrophoresis after purification by the aforementioned method, and a clear band was shown, indicating that the molecular weight of the crude extract is 95 kDa, which is benzopyrone phosphate synthetase. Next, the band was cut from the gel and hydrolyzed by trypsin before proteomics analysis by LC-MS/MS. The results showed that protein has 831 amino acids and the molecular weight is 94.9 kDa, which is the same as the molecular weight of the band on the gel. The pI value was 4.81, and the Mowse value was 765. The protein sequence coverage was 31%. The peptide sequence was a unique peptide sequence based on the results of protein mass spectrometry. This protein was benzopyrone phosphate synthetase and the gene of the target protein was yvkC hypothetical protein [*B. subtilis* subsp. natto BEST195] (Gene ID: 14103593), which consisted of 2520 base. Next, gene cloning and DNA sequencing verified that the nucleic acid sequence encoding the substrate binding domain, ATP binding domain and mobile catalyzing domain, respectively are SEQ ID NO: 4, SEQ ID NO: 5, and SEQ ID NO: 6.

[Test Example] Determination of Activity of the Benzopyrone Phosphate Synthetase In this test example, genistein, a kind of isoflavone, was used for determination of the enzymatic activity of the benzopyrone phosphate synthetase. One unit activity (unit) is defined as the amount of enzyme required to generate 1 nmol of benzopyrone phosphate derivative per minute. The enzyme reaction solution comprised 0.2 mM of benzopyrone compounds, 10 mM of ATP, 10 mM of $MgCl_2$, 0.1 M of Tris-HCl buffer (pH 7.8), 2 mM of DTT, and 5% of glycerol.

Figure 2A:
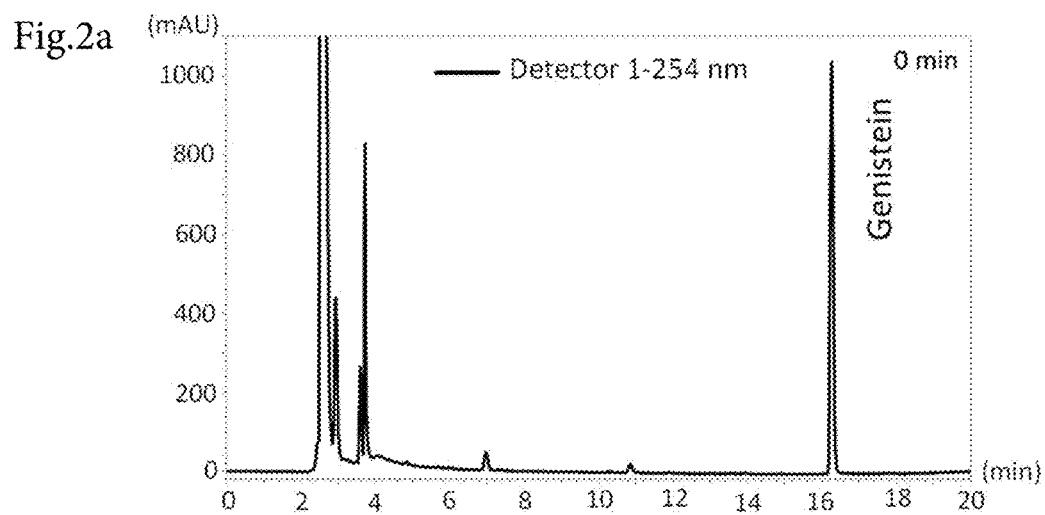
FIG. 2a-2g are the experiment result of the test example for determining the activity of the benzopyrone phosphate synthetase.
Figure 2B:
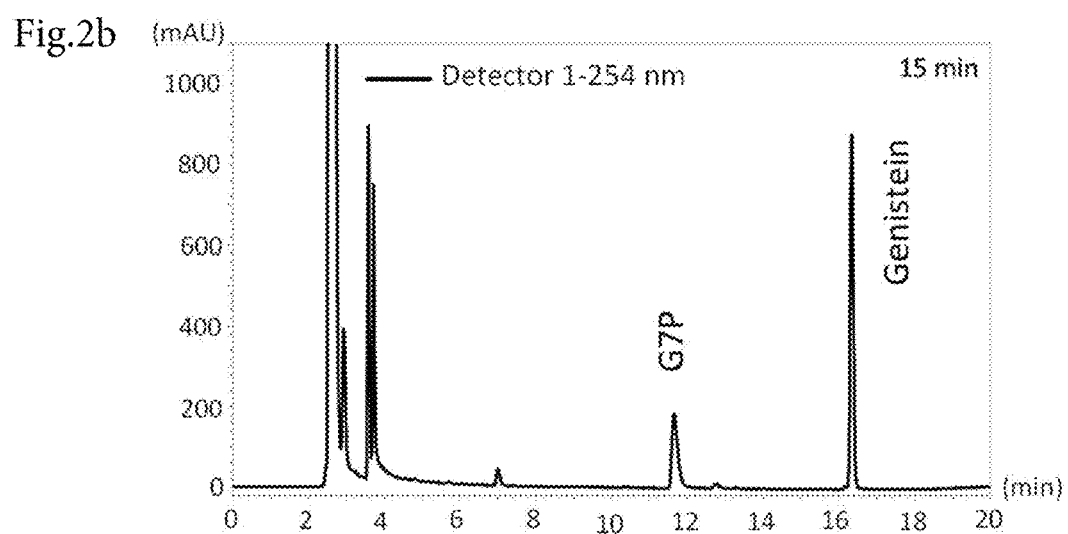
Figure 2C:
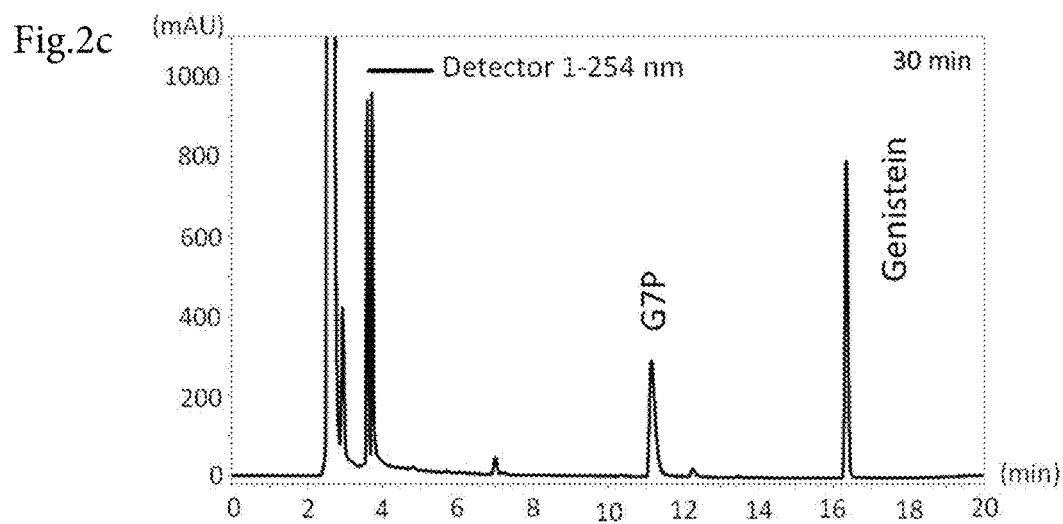
Figure 2D:
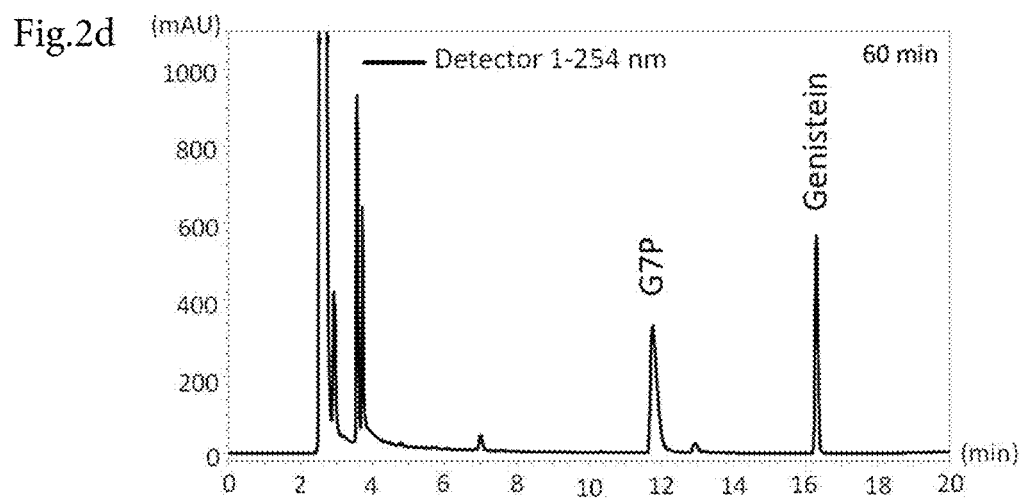
Figure 2E:
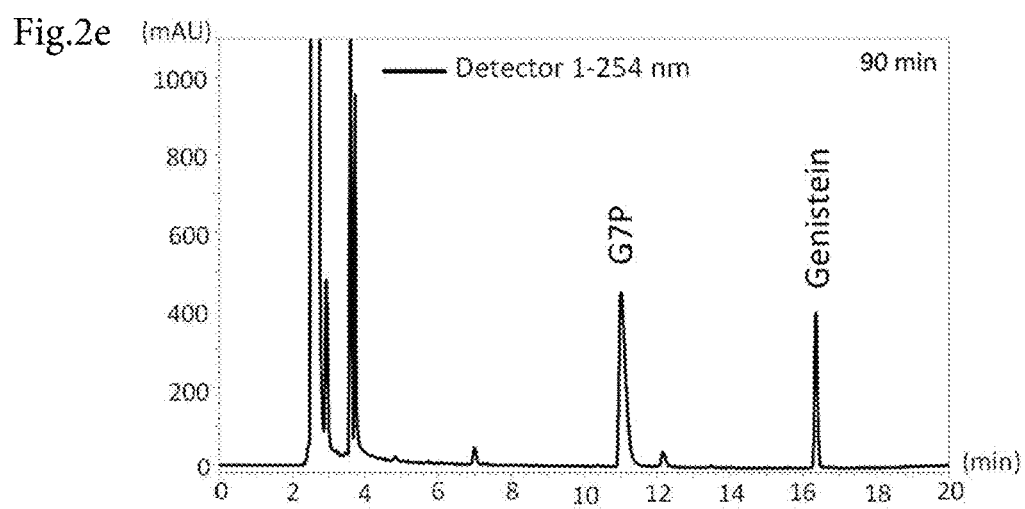
Figure 2F:
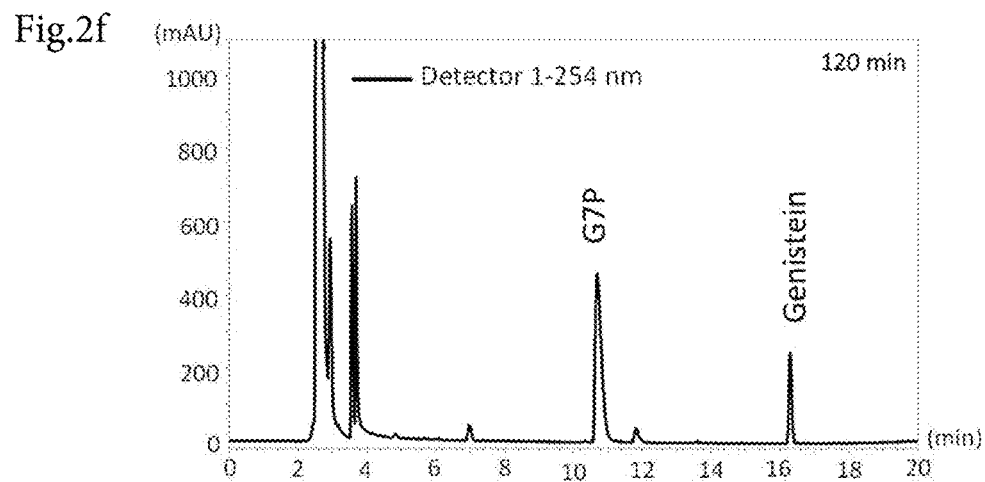
Figure 2G:
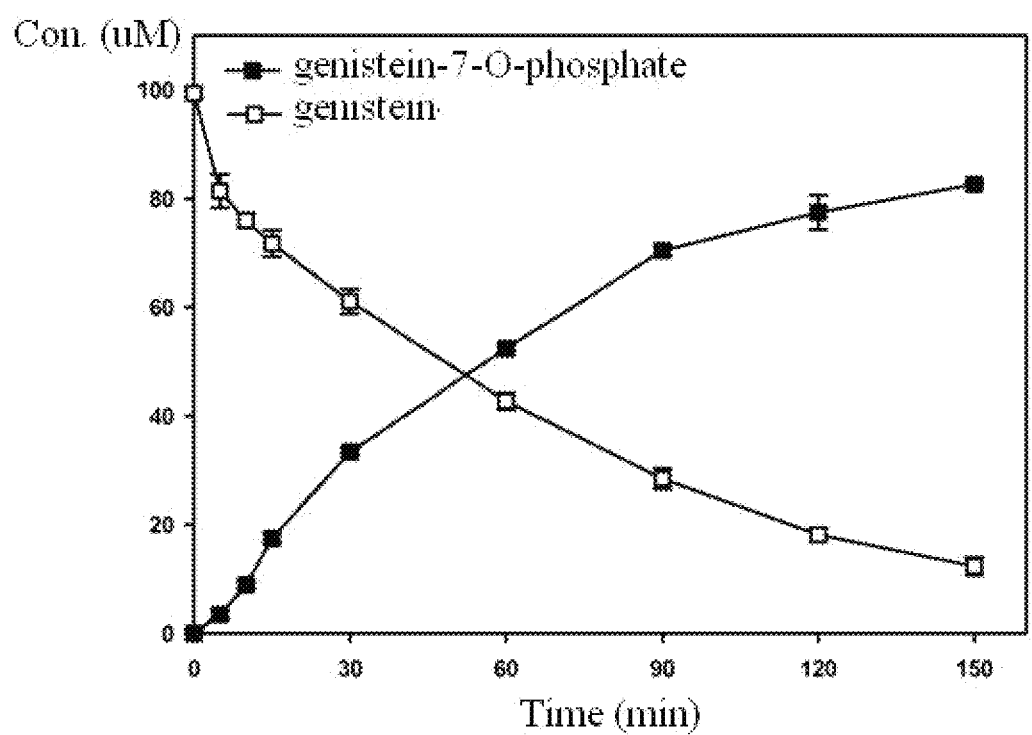

Quantitative Analysis for the Benzopyrone Phosphate Derivanates:

50 µL of the enzyme reaction solution and 50 µL of the benzopyrone phosphate synthetase of the preparation example were well-mixed and reacted at 40° C. for 15 min, 30 min, 60 min, 90 min, and 120 min respectively. 100 µL of methanol was added to terminate the reaction. The samples were centrifuged and the supernatants were analyzed by HPLC-UV/Vis for the content of genistein and the genistein derivates of genistein-7-O-phosphate (G7P), as shown in FIGS. 2a and 2b. In FIG. 2a, (a) to (g) are the HPLC-UV/Vis mass spectra of the reaction results of the reactant solution and benzopyrone phosphate at 40° C. for 0 min, 15 min, 30 min, 60 min, 90 min, and 120 min respectively. As shown in FIG. 2b, the genistein concentration decreased but the genistein-7-O-phosphate (G7P) concentration increased as the reaction time increased. After 60 min of reaction, the genistein concentration was less than genistein-7-O-phosphate (G7P) concentration, and the concentration change slowed down after 120 min of reaction.

Production of Benzopyrone Phosphates

Examples 1 to 5 shows that different types of benzopyrone compounds were phosphorylated by the purified enzyme in order to understand the specificity of *B. subtilis* BCRC 19679 benzopyrone phosphate synthetase to different substrates. According to the above testing example, the reaction time is set as 60 min, and the experimental steps are as follows.

The enzyme reaction solution was made of 0.2 mM isoflavone (daidzein and genistein), flavone (apigenin and 6-hydroxyflavone), flavonol (kaempferol and quercetin), flavanone (naringenin and hesperetin), and others (Urolithin A and silymarin). The enzyme reaction solution and enzyme solution were mixed in 1:1 (v:v) ratio and reacted at 40° C. for 1 h. Methanol was added to terminate the reaction. The supernatant was analyzed by HPLC after shaking and centrifugation, and the chemical compound was detected by a photo diode array (PDA) detector. Then, the derivatives were collected at the outlet of PDA detector, and molecular weight of the derivatives was determined by ESI-MS analysis.

The condition for HPLC analysis on the enzymatic reaction product is as follows: YMC-Pack ODS-AM column (250 mm×4.6 mm, 5 μm); 20 μL injection volume; UV detector (wavelength are shown in FIGS. 1 to 10); mobile phase were: Solvent A: 0.1% (v/v) acetic acid in $H_2O$, and Solvent B: 0.1% (v/v) acetic acid in acetonitrile; flow rate was 1.0 mL/min; HPLC gradient elution condition: after the sample injection, Solvent B was increased from 15% to 25% within 5 min, from 25% to 40% in the next 5 min, from 40% to 75% in the following 20 min, and returned to 15% in the last 5 min, followed by 5 min balance. The sample was balanced for 5 min with 15% Solvent B before reinjection.

The condition of LC-MS/MS analysis is as follows: the mass spectrometer was Thermo electrospray ionization mass spectrometer (Thermo Finnigan LXQ Aadvantag, San Jose, Calif.); the source of ion was from electron spray ionization (ESI); the mass analyzer was ion trap; positive mode; capillary temperature of 200.5° C.; 40 V of injection cone voltage; 3.73 V of capillary voltage.

[Example 1] Reactions of Benzopyrone Phosphate Synthetase with Isoflavone

Figure 3A:
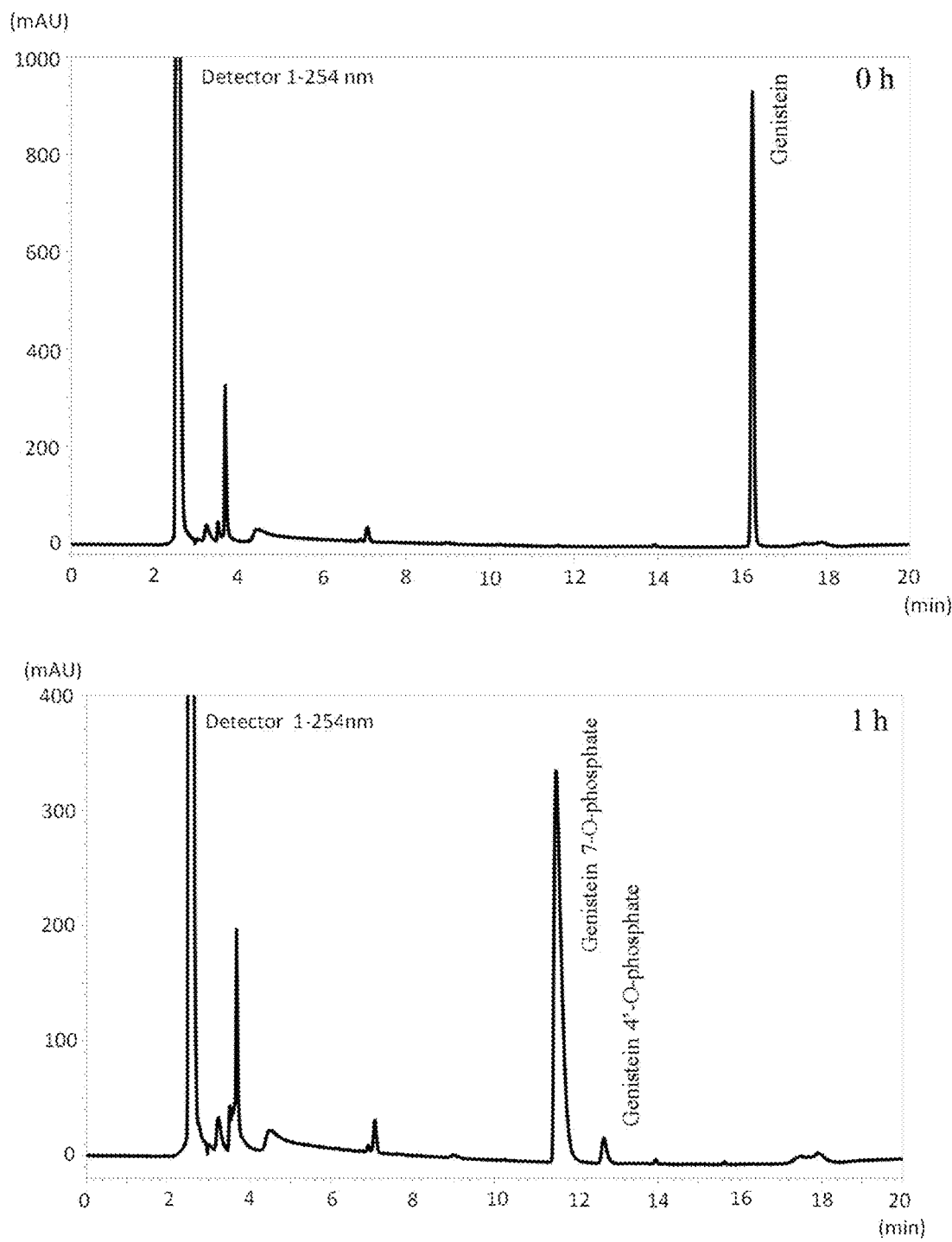
FIG. 3a-3c are the HPLC chromatograms of example 1 for the reaction of genistein and benzopyrone phosphate synthetase.
Figure 3B:
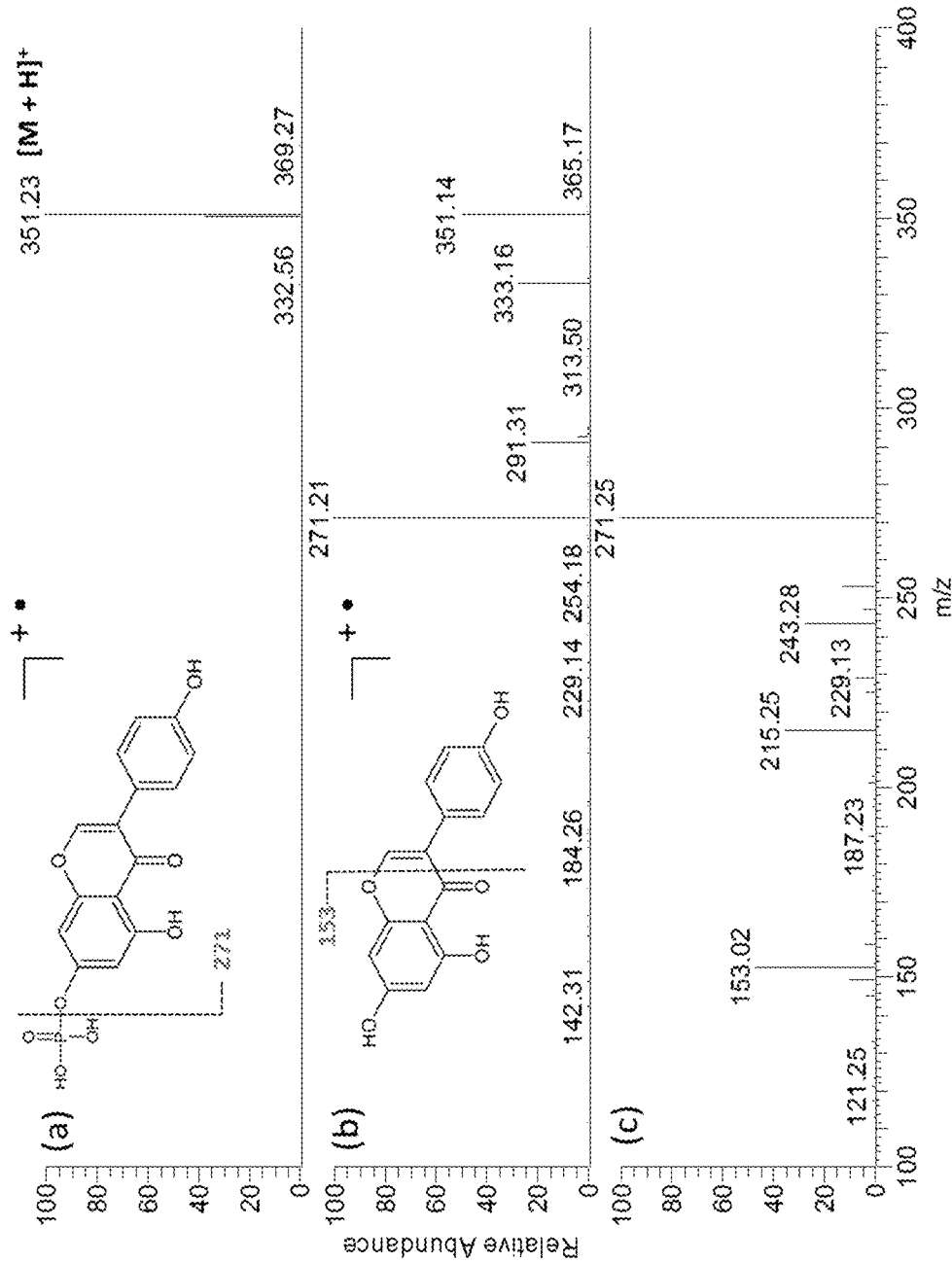
Figure 3C:
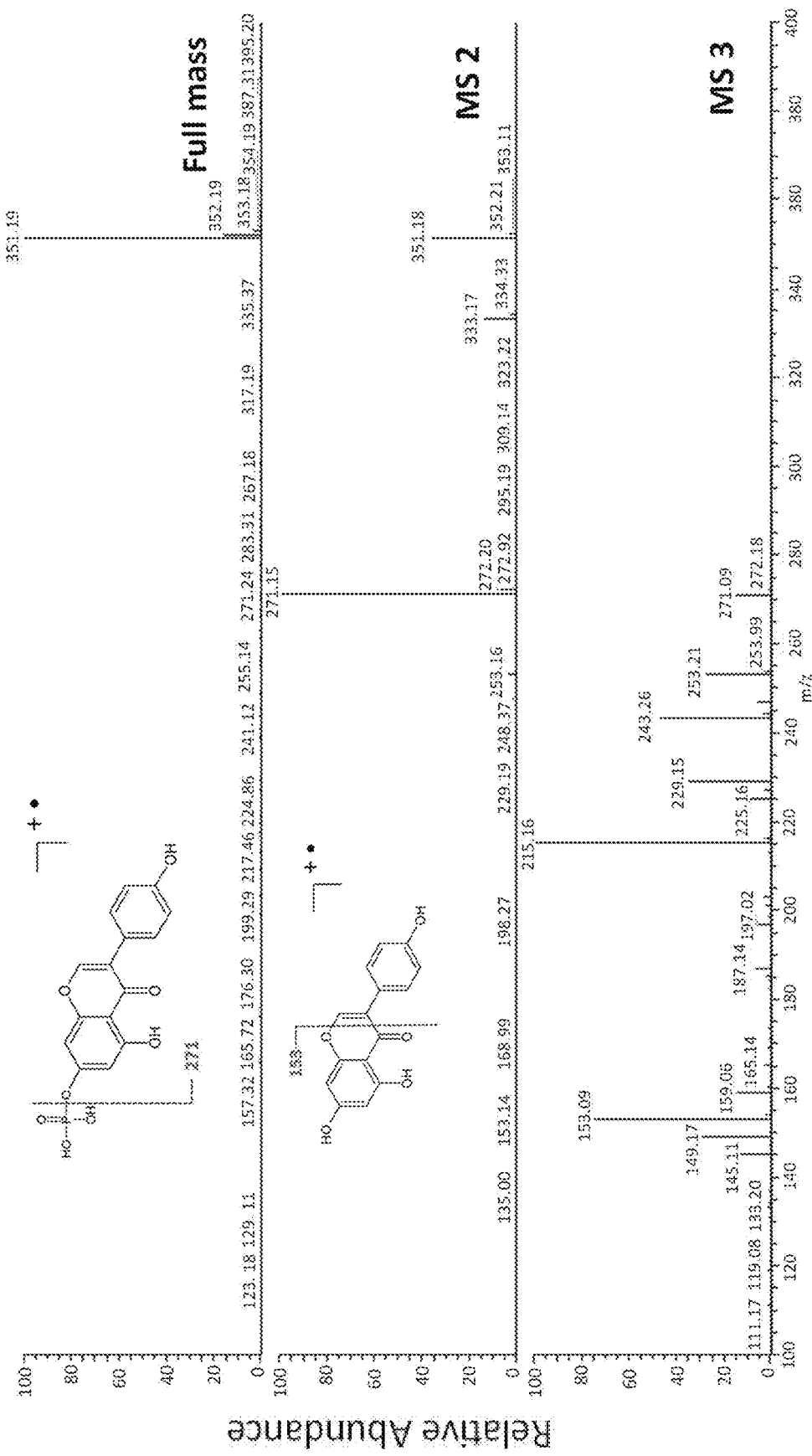
Figure 4A:
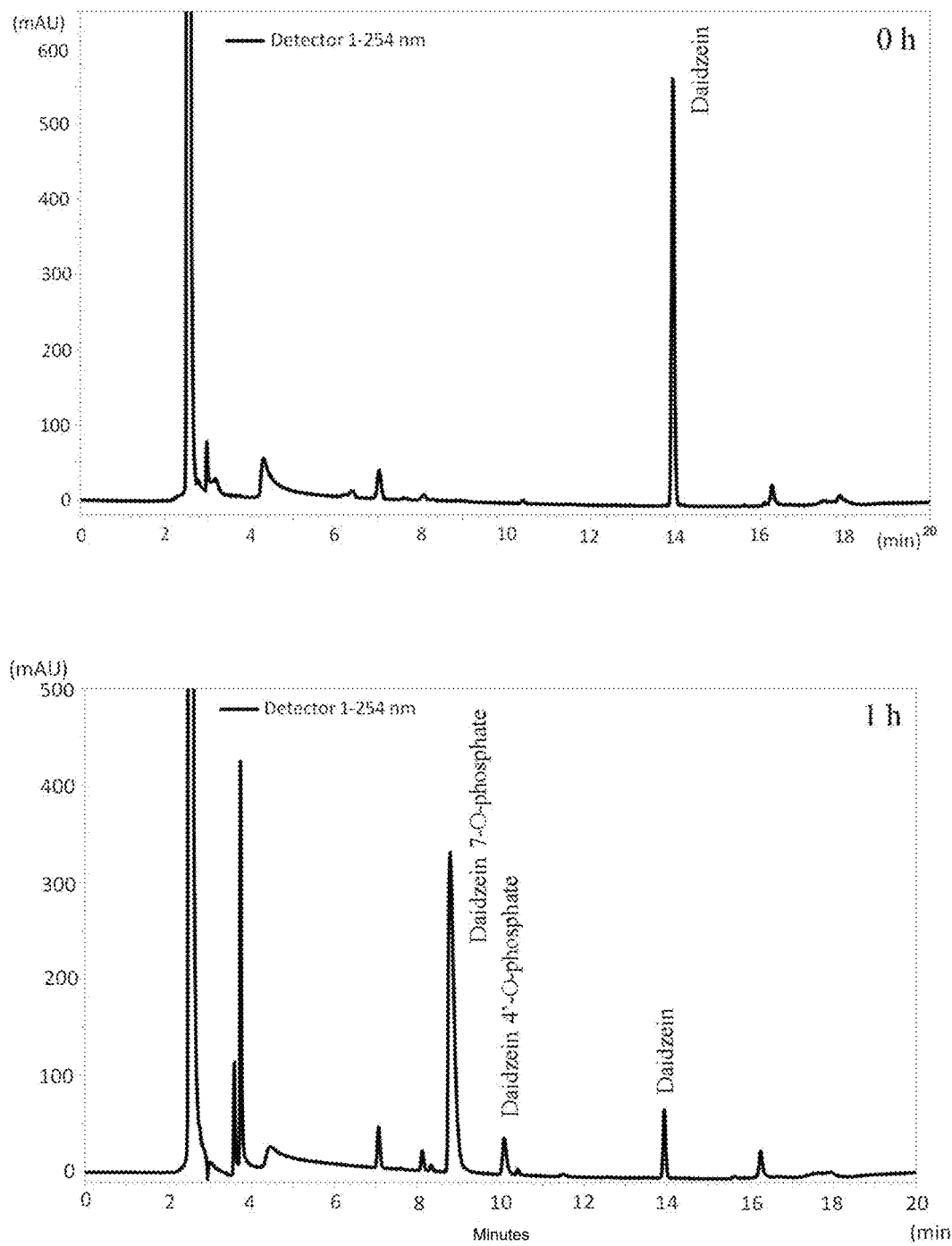
FIG. 4a-4c are the HPLC chromatograms of example 1 for the reaction of daidzein and benzopyrone phosphate synthetase.
Figure 4B:
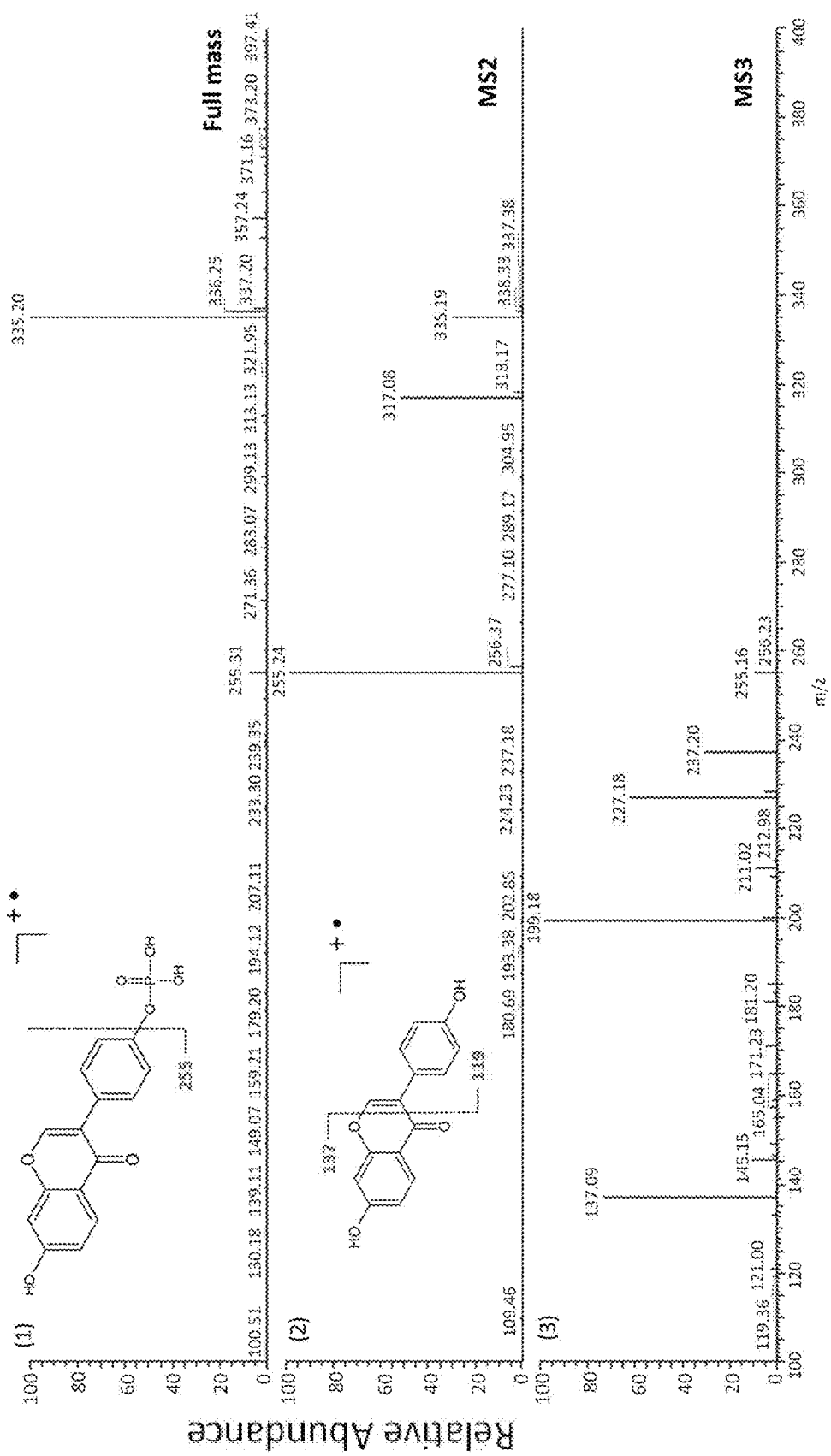
Figure 4C:
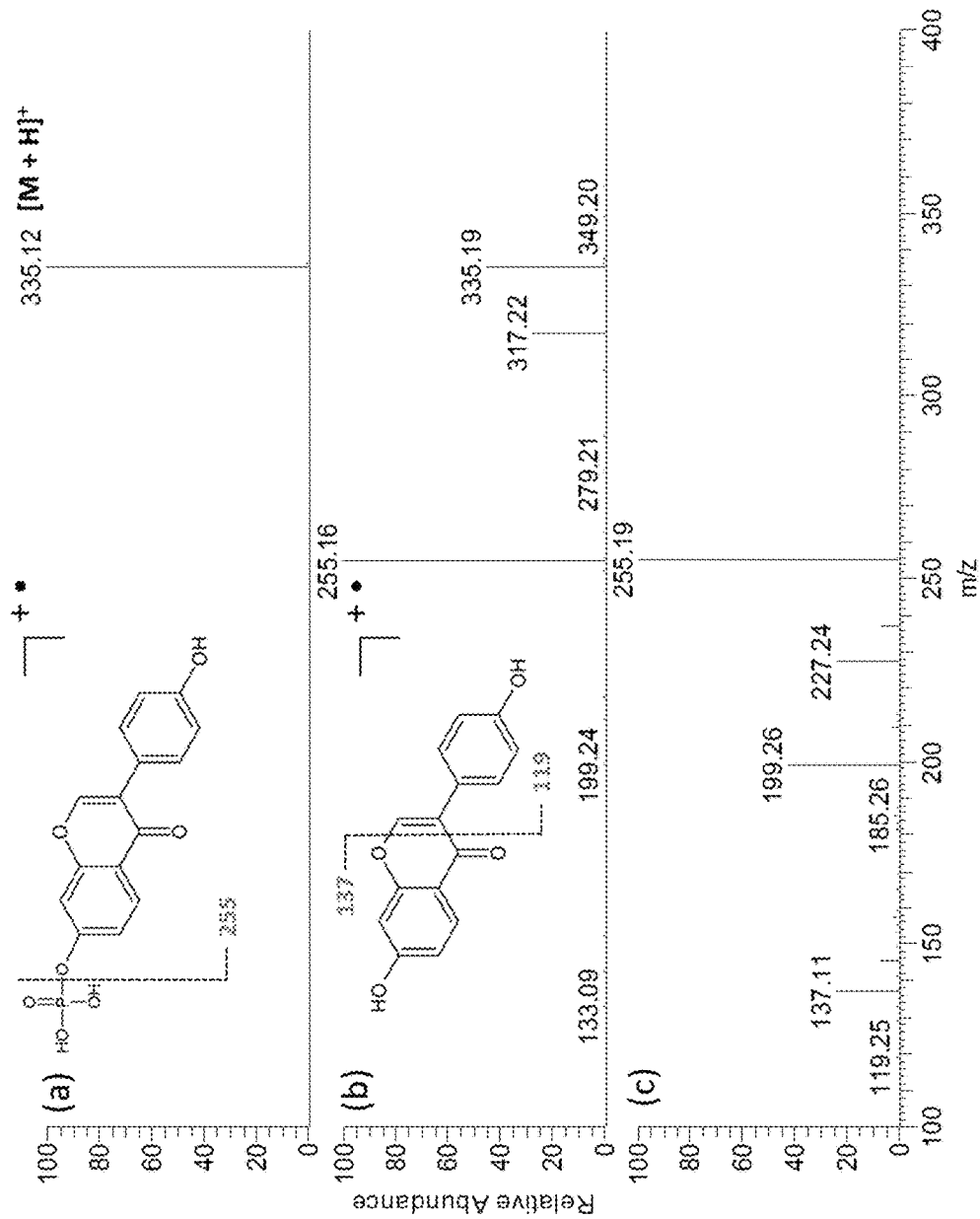
Figure 5A:
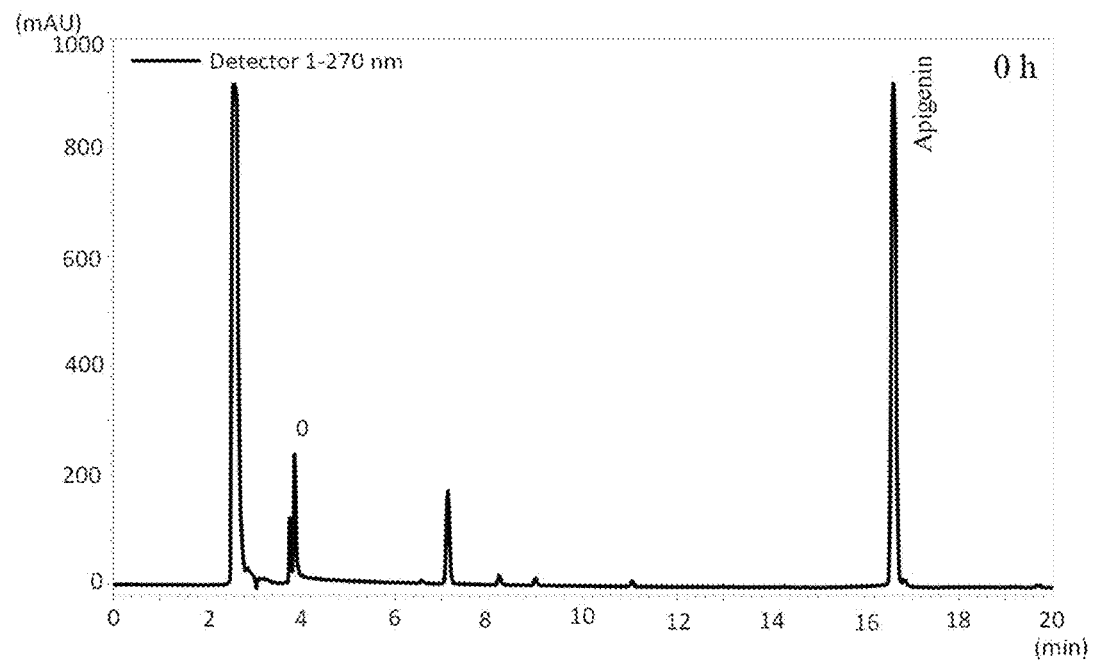
FIG. 5a-5d are the HPLC chromatograms of example 2 for the reaction of apigenin and benzopyrone phosphate synthetase.
Figure 5A:
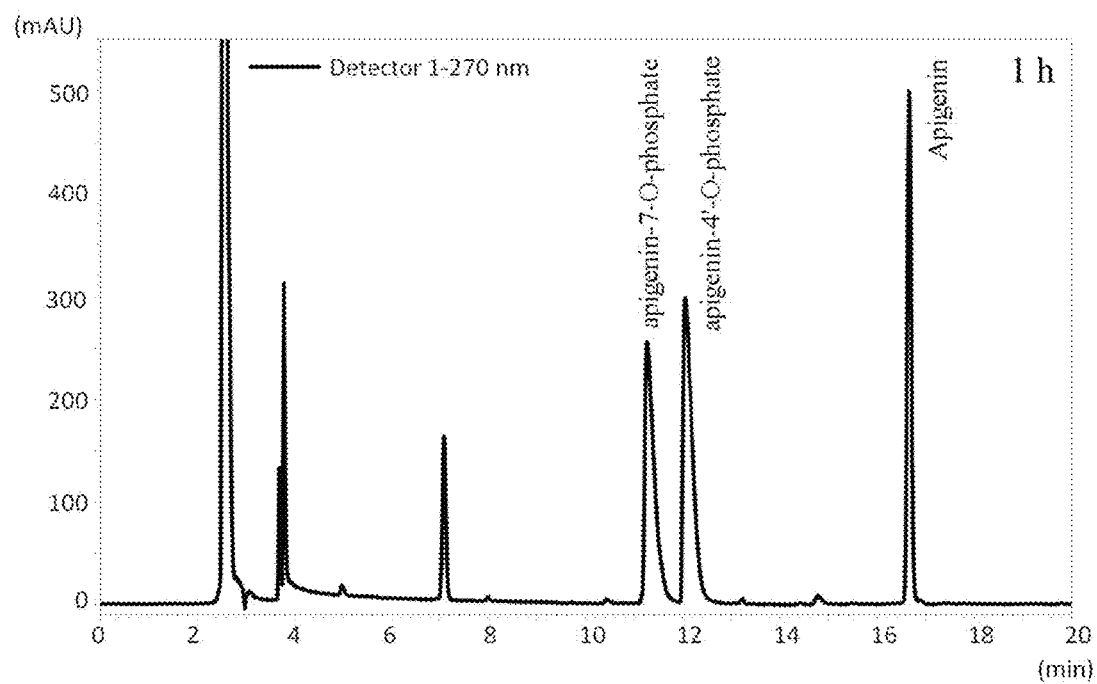
Figure 5B:
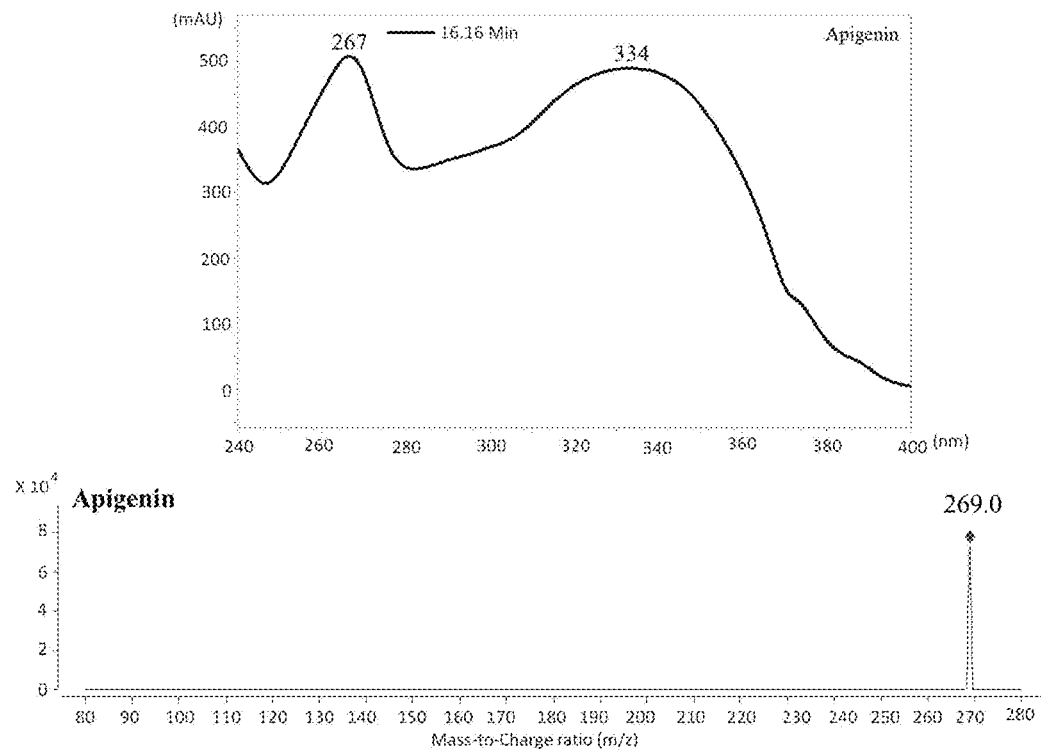
Figure 5C:
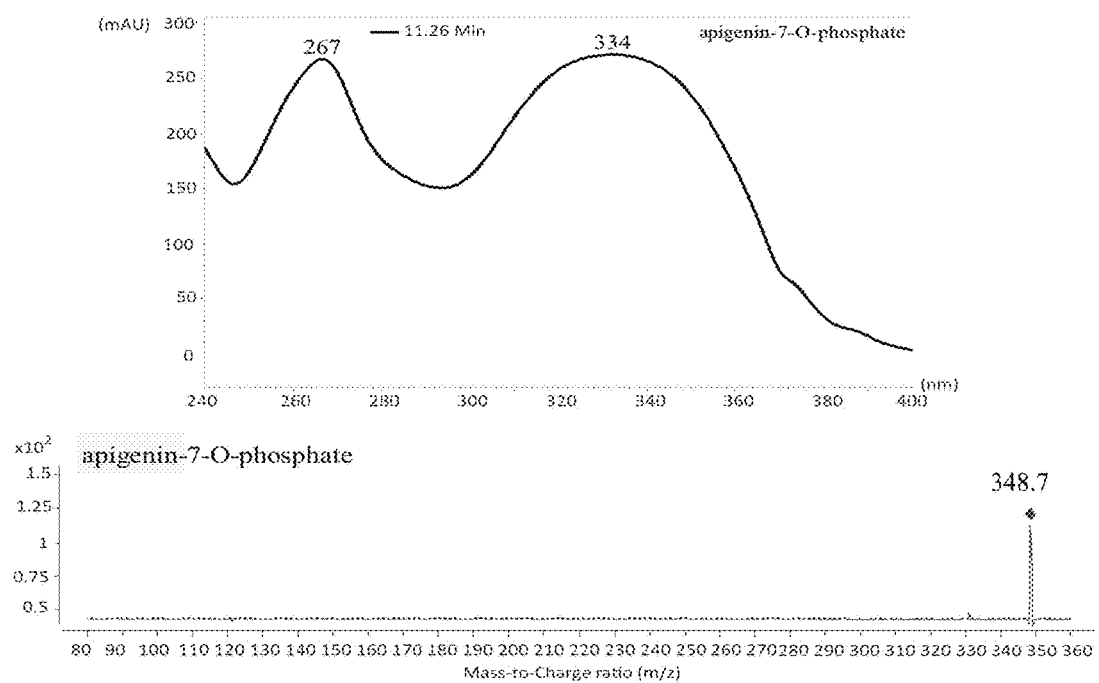
Figure 5D:
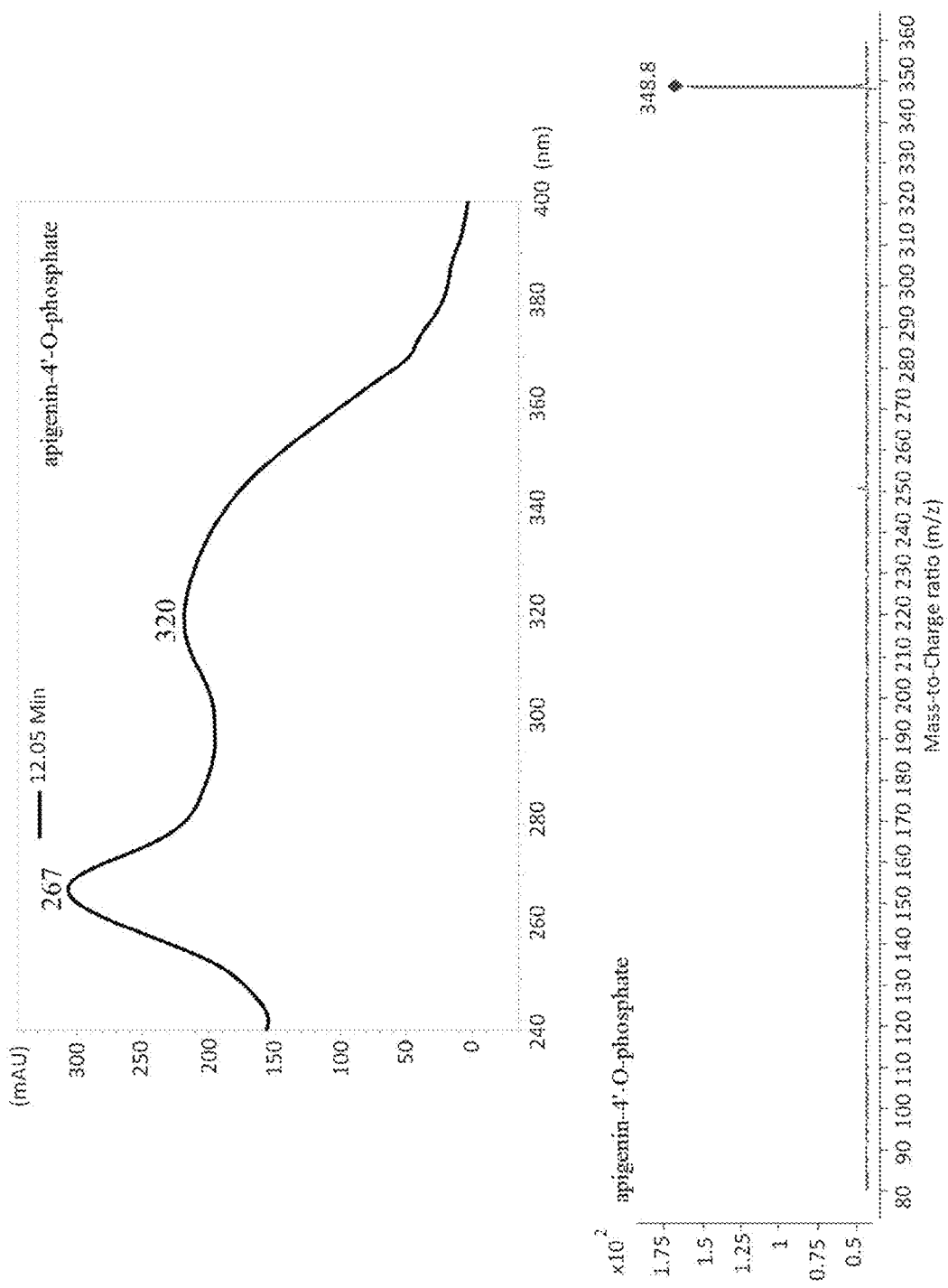

FIGS. 3 and 4 are described together as followed. The solubility of isoflavones in water is quite low. The solubility of genistein and daidzein is 0.8 and 8.2 μg/mL, respectively. Isoflavones are classified as Class 4 substances in BCS classification (low solubility, low penetration). FIGS. 3 and 4 show the spectral information (UV absorption spectrum and ESI-MS spectrum of parent ion and fragment ion) of the derivatives generated by reaction between benzopyrone phosphate synthetase and isoflavones. The reaction between genistein and benzopyrone phosphate synthetase generates genistein-7-O-phosphate and genistein-4'-O-phosphate, as shown in Formula 1. After daidzein reacts with benzopyrone phosphate synthetase, daidzein-7-O-phosphate and daidzein-4'-O-phosphate are generated, as illustrated in Formula 2.

Formula 1

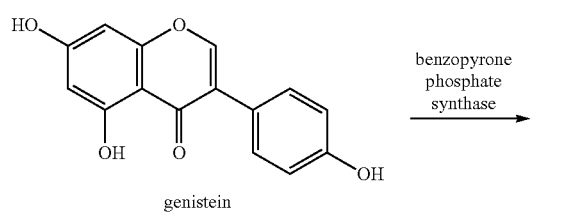

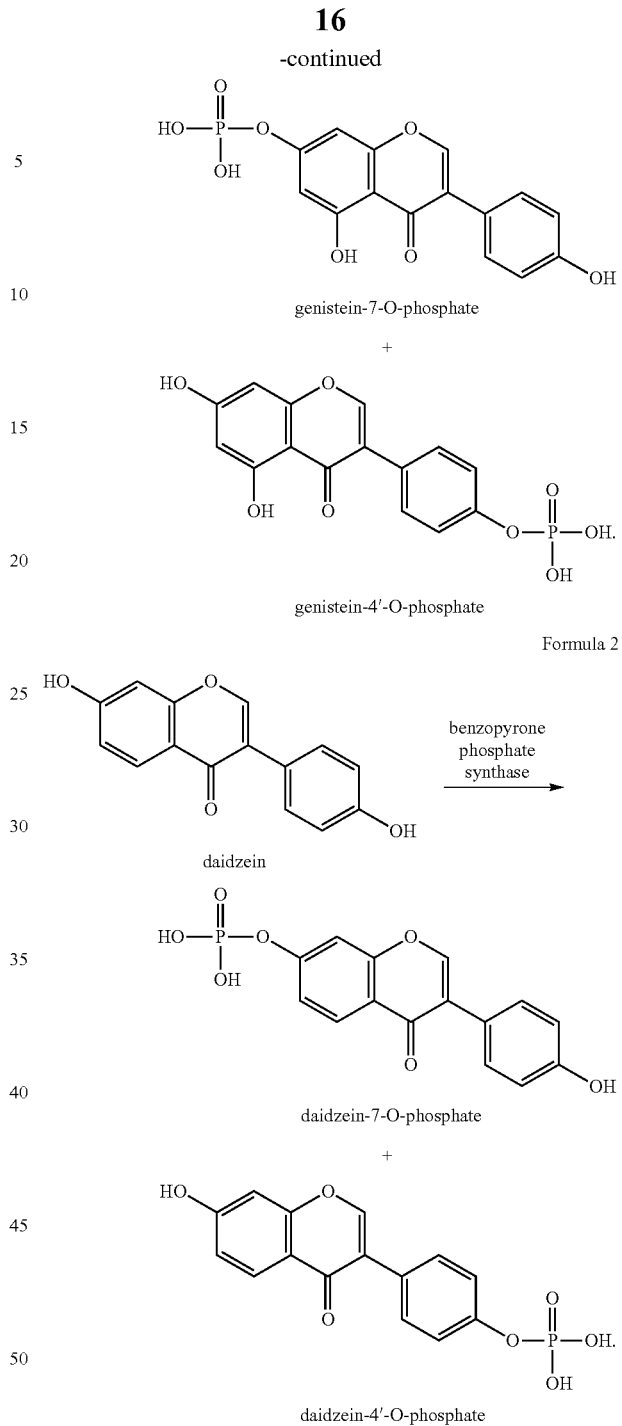

Solubility of Isoflavones

As shown in Table 1, the solubility of genistein and genistein-7-O-phosphate are 0.82 mg/L and $1.0 \times 10^5$ mg/L, respectively, in 25° C. water. The solubility of daidzein and daidzein-7-O-phosphate are 1.36 mg/L and $1.79 \times 10^5$ mg/L, respectively, in 25° C. water. The solubility of genistein-7-O-phosphate and daidzein-7-O-phosphate is ten million times higher than that of genistein and daidzein, which demonstrates that the solubility of de-glycosylated isoflavones can be increased by turned into isoflavones phosphate. This can increase the application of isoflavones in pharmaceuticals, food, and cosmetics.

TABLE 1

Solubility of isoflavone phosphate conjugates and aglycones in DI water (25° C.)

| Compound | Water solubility (mg/L) | Solubility enhancement ratio[a] |
|---|---|---|
| Genistein | 0.82 | — |
| Genistein-7-O-phosphate | $1.0 \times 10^5$ | $1.2 \times 10^5$ |
| Daidzein | 1.36 | — |
| Daidzein-7-O-phosphate | $1.79 \times 10^5$ | $1.3 \times 10^5$ |

[a] Solubility enhancement ratio = $\dfrac{\text{Solubility of isoflavone phosphate conjugates (mg/L)}}{\text{Solubility of aglycones (mg/L)}}$

[Example 2] Reactions of Benzopyrone Phosphate Synthetase with Flavones

Figure 6A:
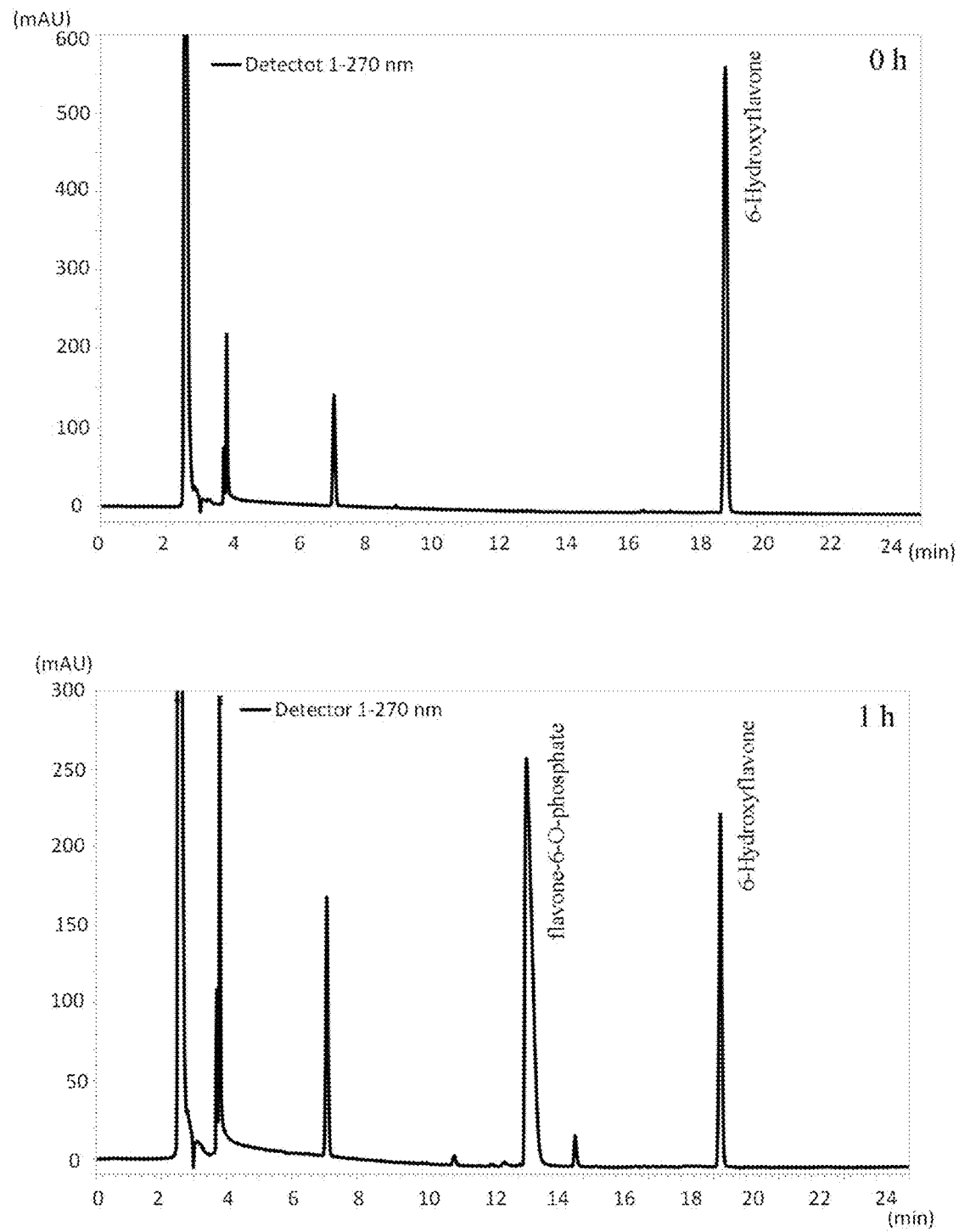
FIG. 6a-6c are the HPLC chromatograms of example 2 for the reaction of 6-hydroxyflavone and benzopyrone phosphate synthetase.
Figure 6B:
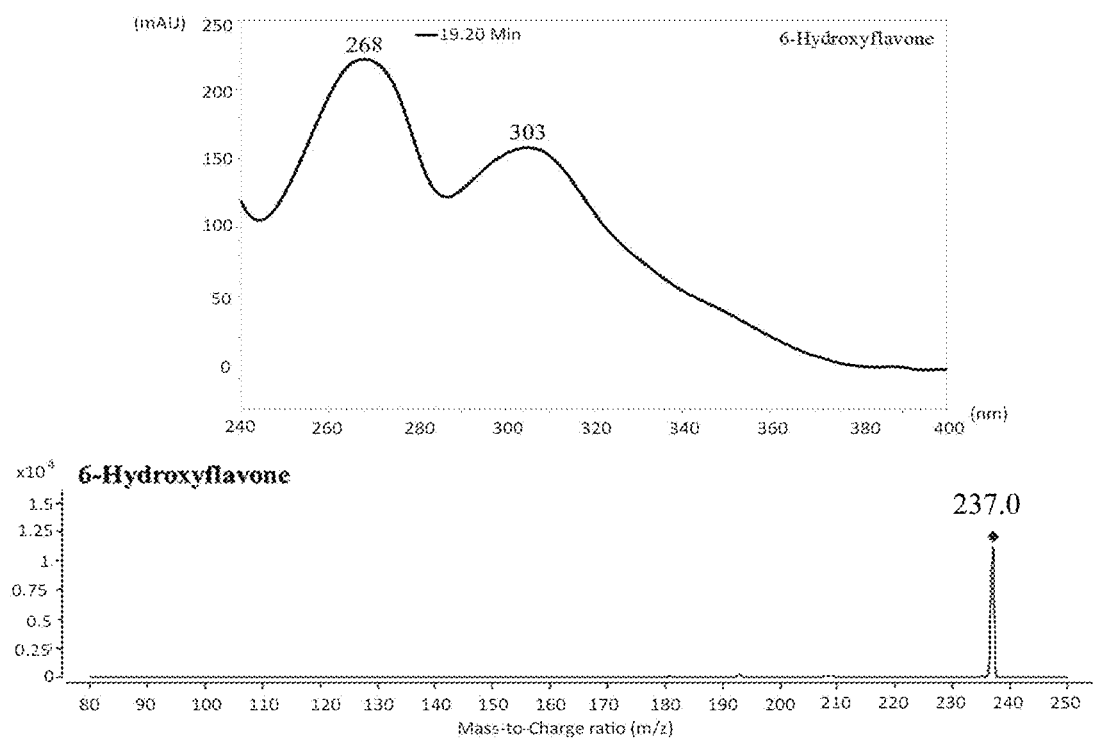
Figure 6C:
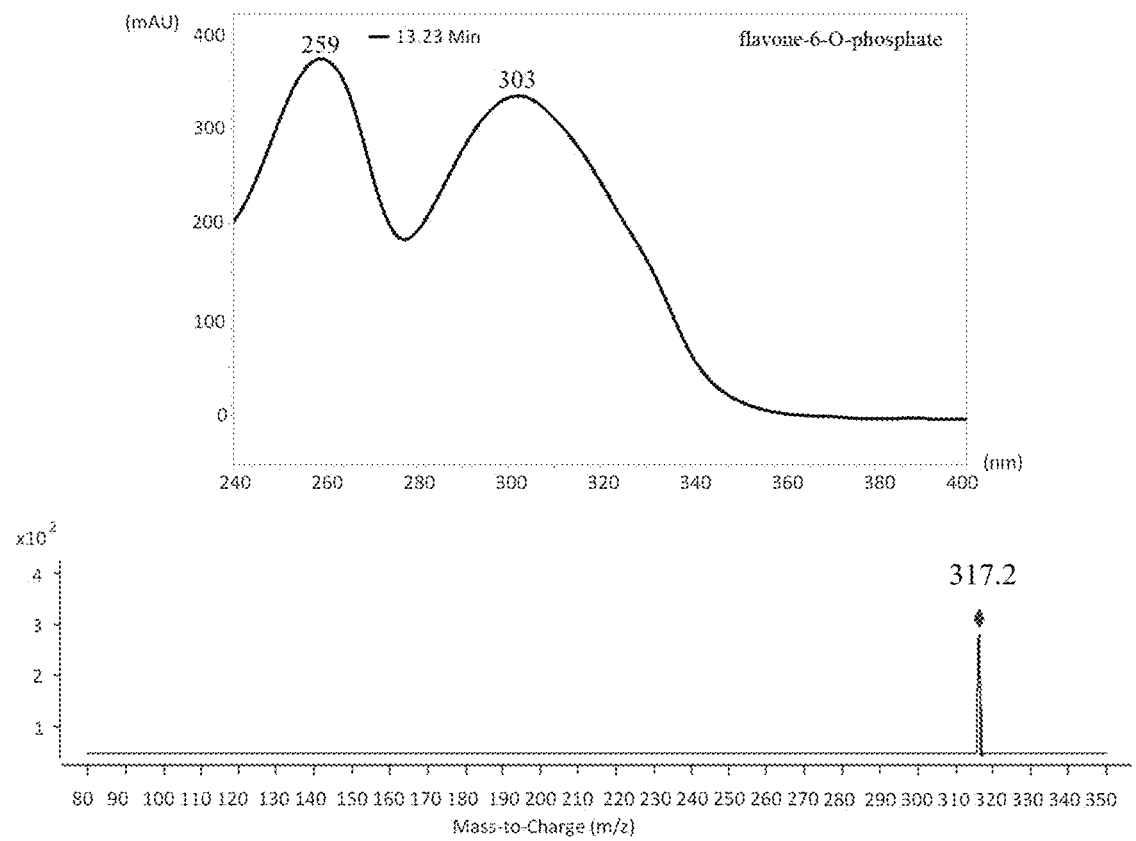
Figure 7A:
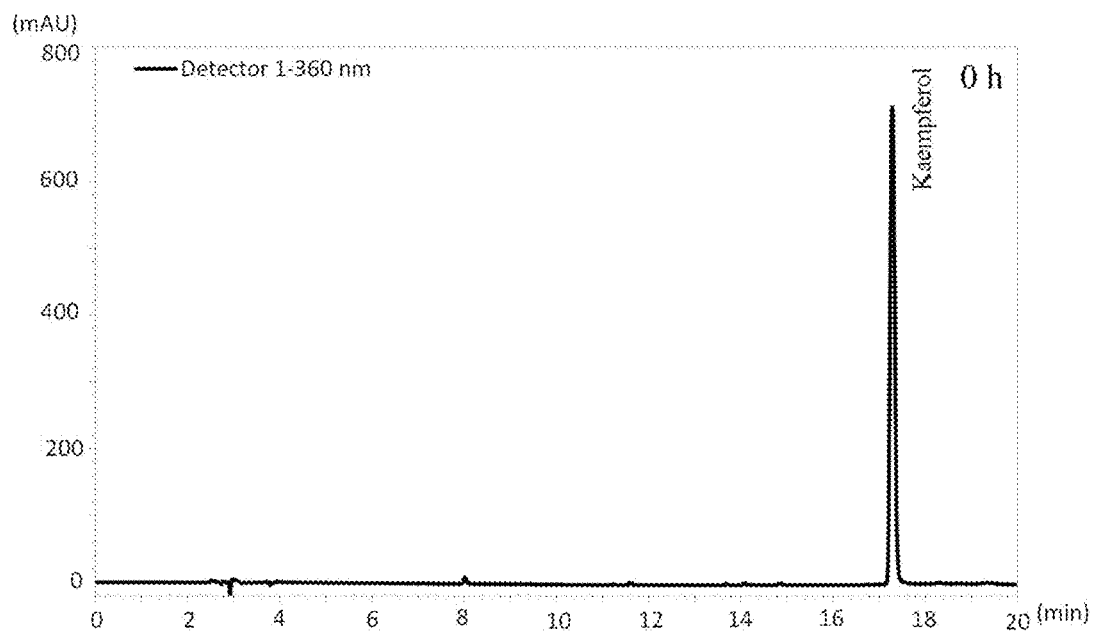
FIG. 7a-7c are the HPLC chromatograms of example 3 for the reaction of kaempferol and benzopyrone phosphate synthetase.
Figure 7A:
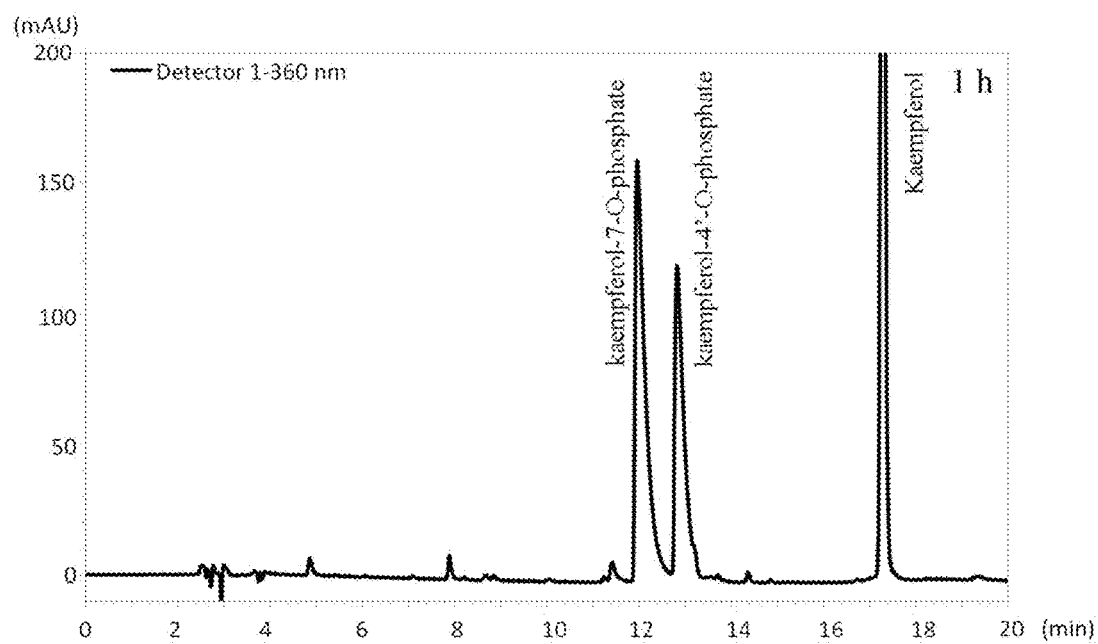
Figure 7B:
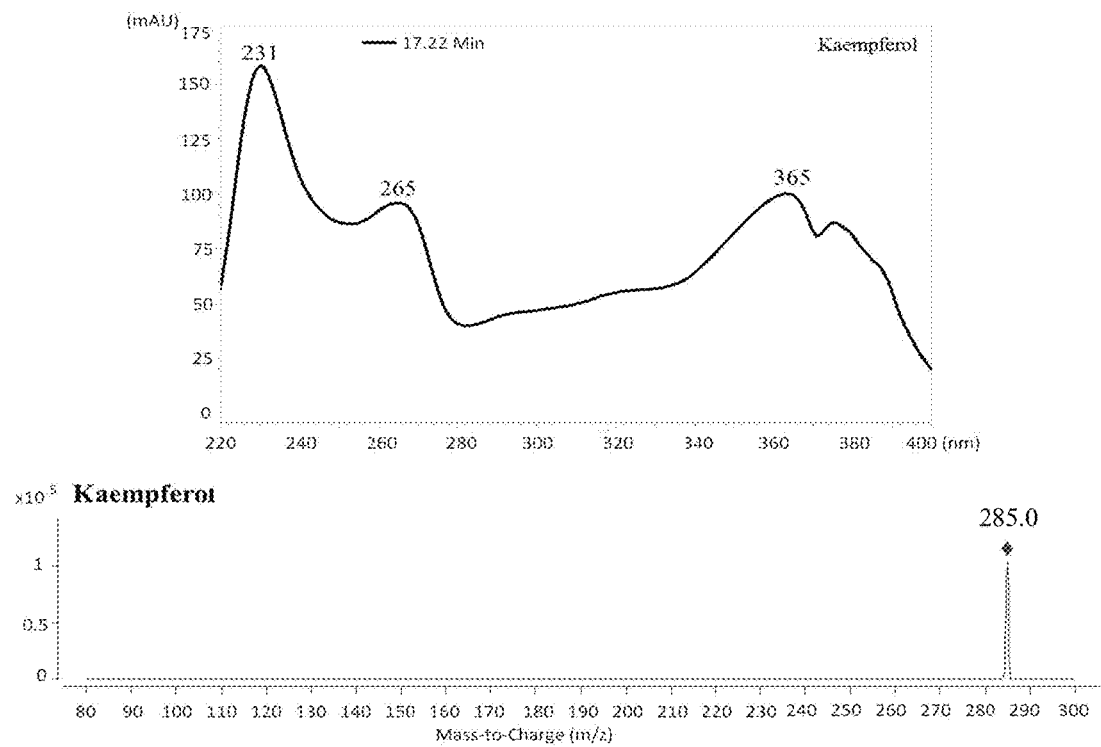
Figure 7C:
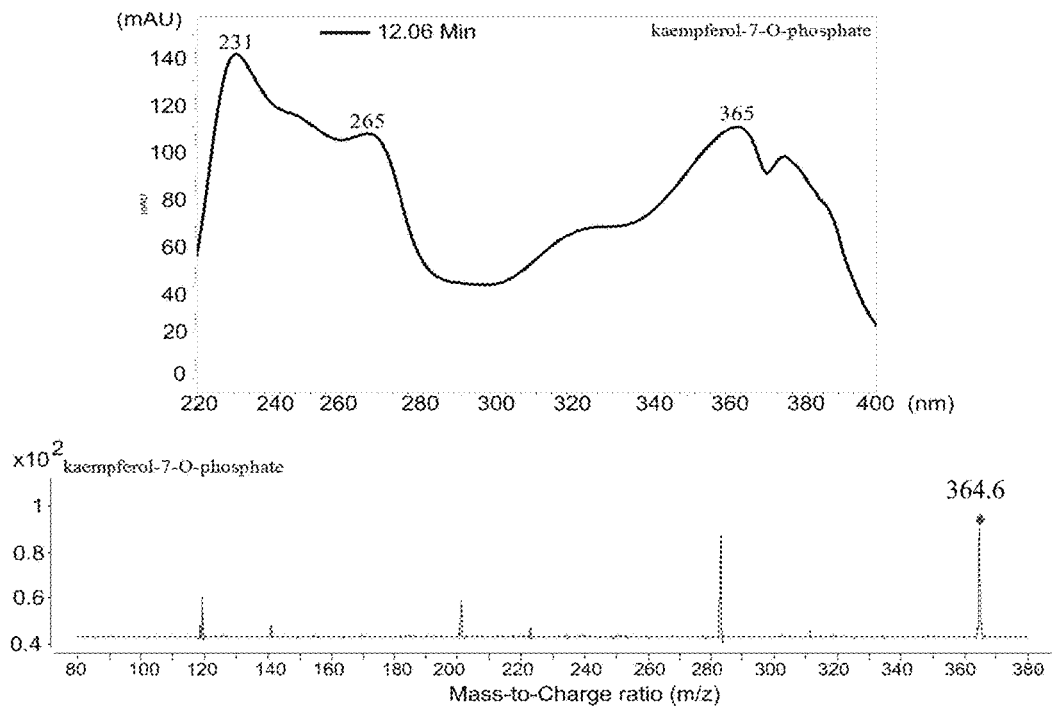

FIGS. 5 and 6 are described together as followed.

The solubility of apigenin and 6-hydroxyflavone is quite low, less than 2.2 μg/mL. Apigenin belongs to Class 4 (low solubility, low penetration) substance in the BCS classification. FIGS. 5 and 6 show the spectral information (UV absorption spectrum and ESI-MS spectrum of parent ion and fragment ion) of the derivatives generated by reaction between benzopyrone phosphate synthetase and flavones. The reaction between apigenin and benzopyrone phosphate synthetase generates apigenin-7-O-phosphate and apigenin-4'-O-phosphate, as shown in Formula 3. After 6-hydroxyflavone reacts with benzopyrone phosphate synthetase, flavone-6-O-phosphate is generated, as illustrated in Formula 4.

Formula 3

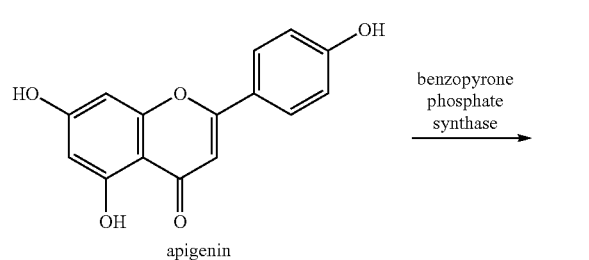

apigenin → benzopyrone phosphate synthase → apigenin-7-O-phosphate +

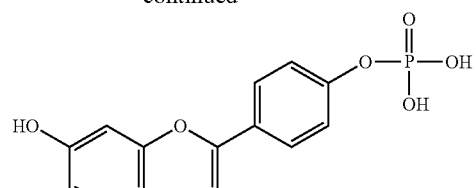

apigenin-4'-O-phosphate

Formula 4

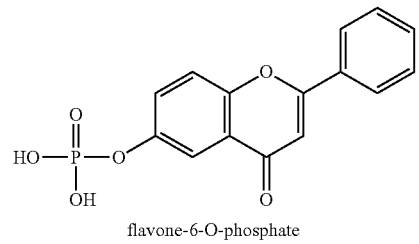

6-hydroxyflavone → benzopyrone phosphate synthase → flavone-6-O-phosphate

[Example 3] Reactions of Benzopyrone Phosphate Synthetase with Flavonols

Figure 8A:
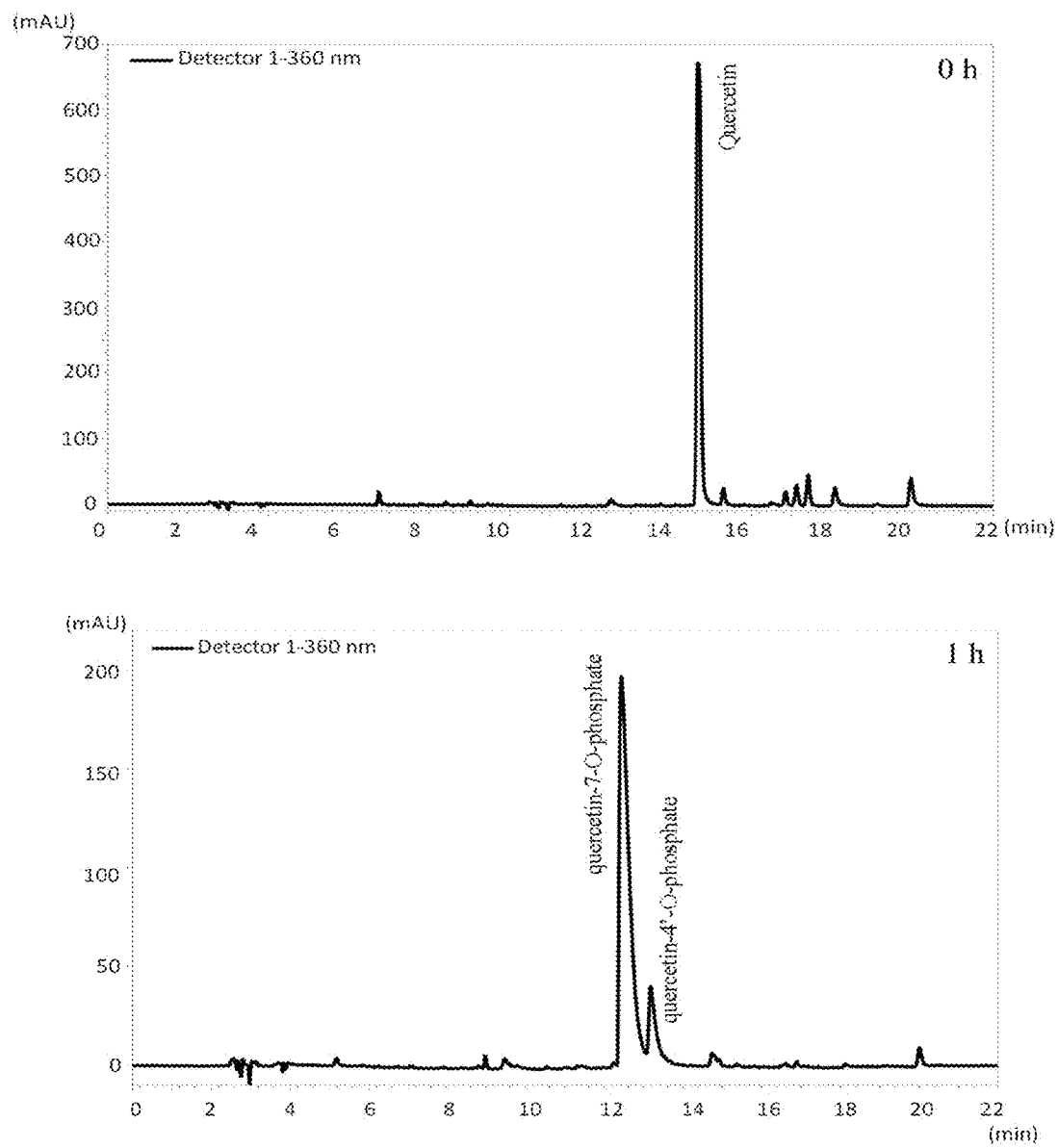
FIG. 8a-8c are the HPLC chromatograms of example 3 for the reaction of quercetin and benzopyrone phosphate synthetase.
Figure 8B:
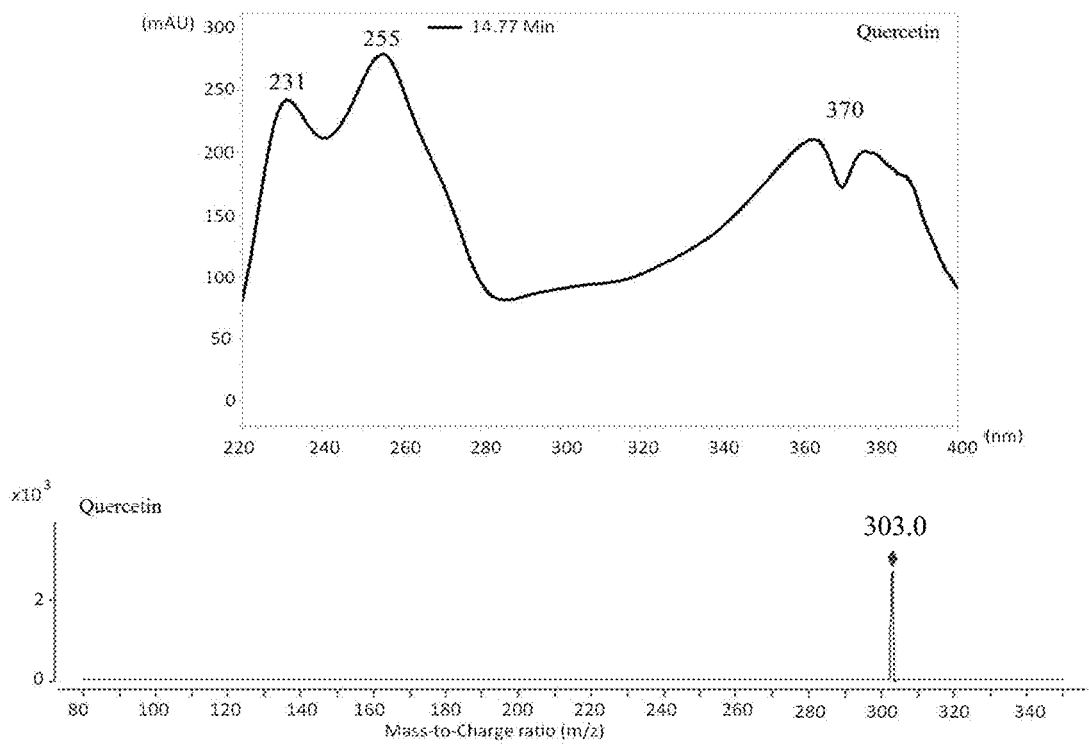
Figure 8C:
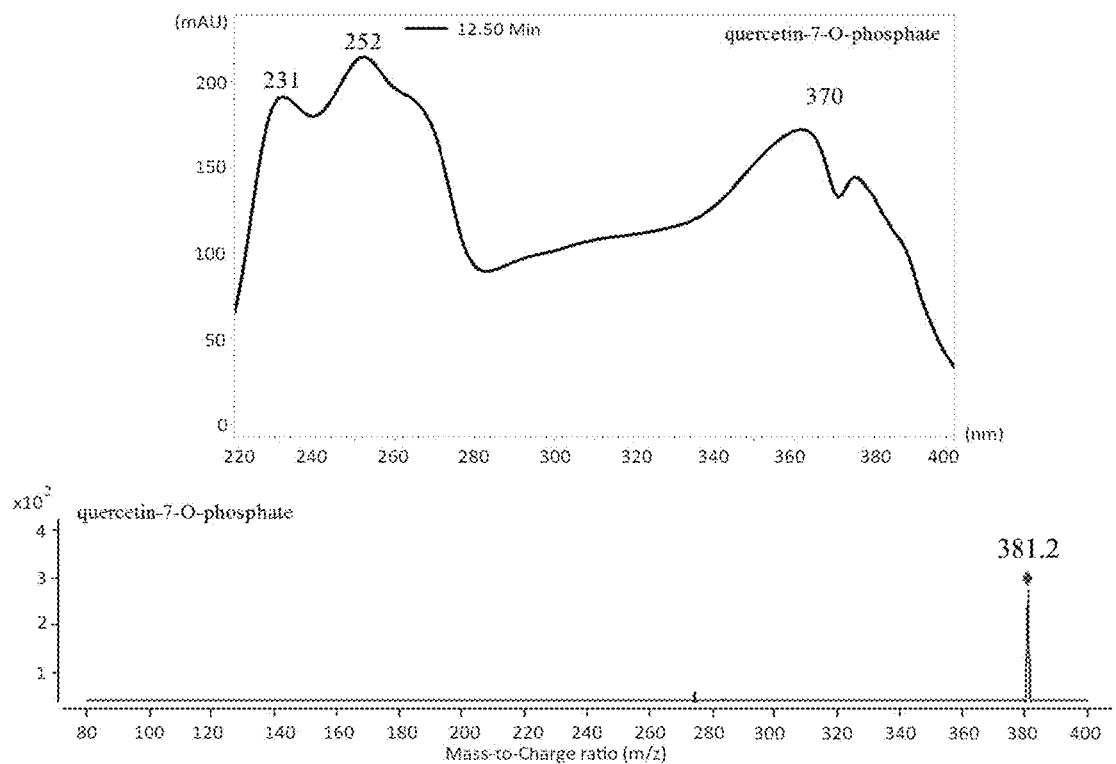

FIGS. 7 and 8 are described together as followed.

Kaempferol and quercetin, types of flavonols are barely insoluble in water, and classified as Class 2 (low solubility, high penetration) substances in the BCS classification. FIGS. 7 and 8 depict the spectral information (UV absorption spectrum and ESI-MS spectrum of parent ion and fragment ion) of the derivatives generated by reaction between benzopyrone phosphate synthetase and flavonols.

Kaempferol reacted with benzopyrone phosphate synthetase and generated kaempferol-7-O-phosphate and kaempferol-4'-O-phosphate, as the following Formula 5. The reaction between kaempferol and benzopyrone phosphate synthetase generates kaempferol-7-O-phosphate and kaempferol-4'-O-phosphate, as shown in Formula 5.

Formula 5

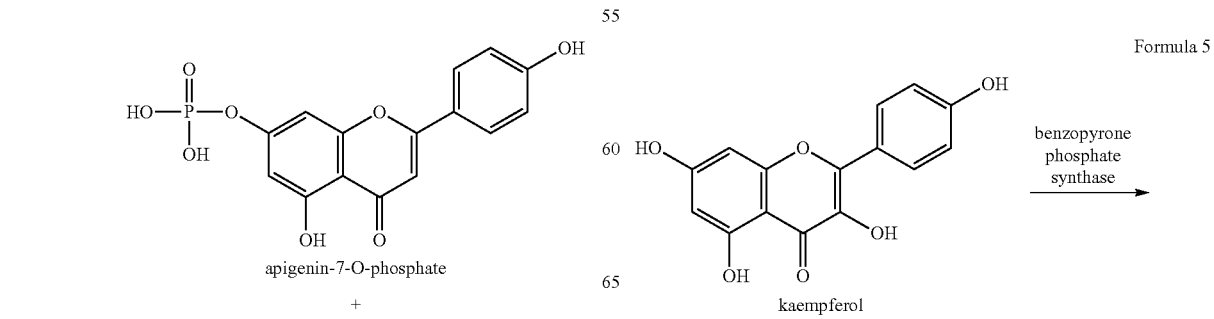

kaempferol → benzopyrone phosphate synthase →

19
-continued

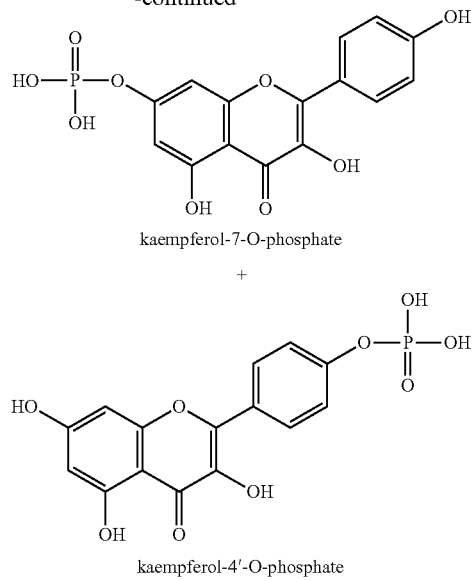

kaempferol-7-O-phosphate

+ kaempferol-4'-O-phosphate

After quercetin reacts with benzopyrone phosphate synthetase, quercetin-7-O-phosphate and quercetin-4'-O-phosphate are synthesized, as illustrated in Formula 6.

Formula 6

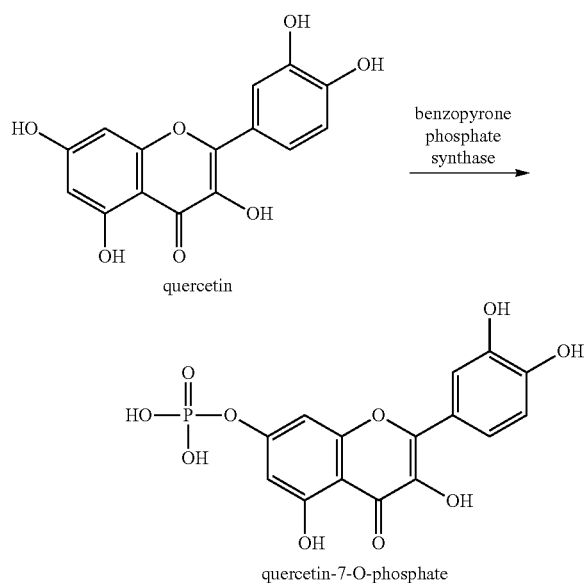

quercetin quercetin-7-O-phosphate

+ quercetin-4'-O-phosphate

20

[Example 4] Reactions of Benzopyrone Phosphate Synthetase with Flavanones

Figure 9A:
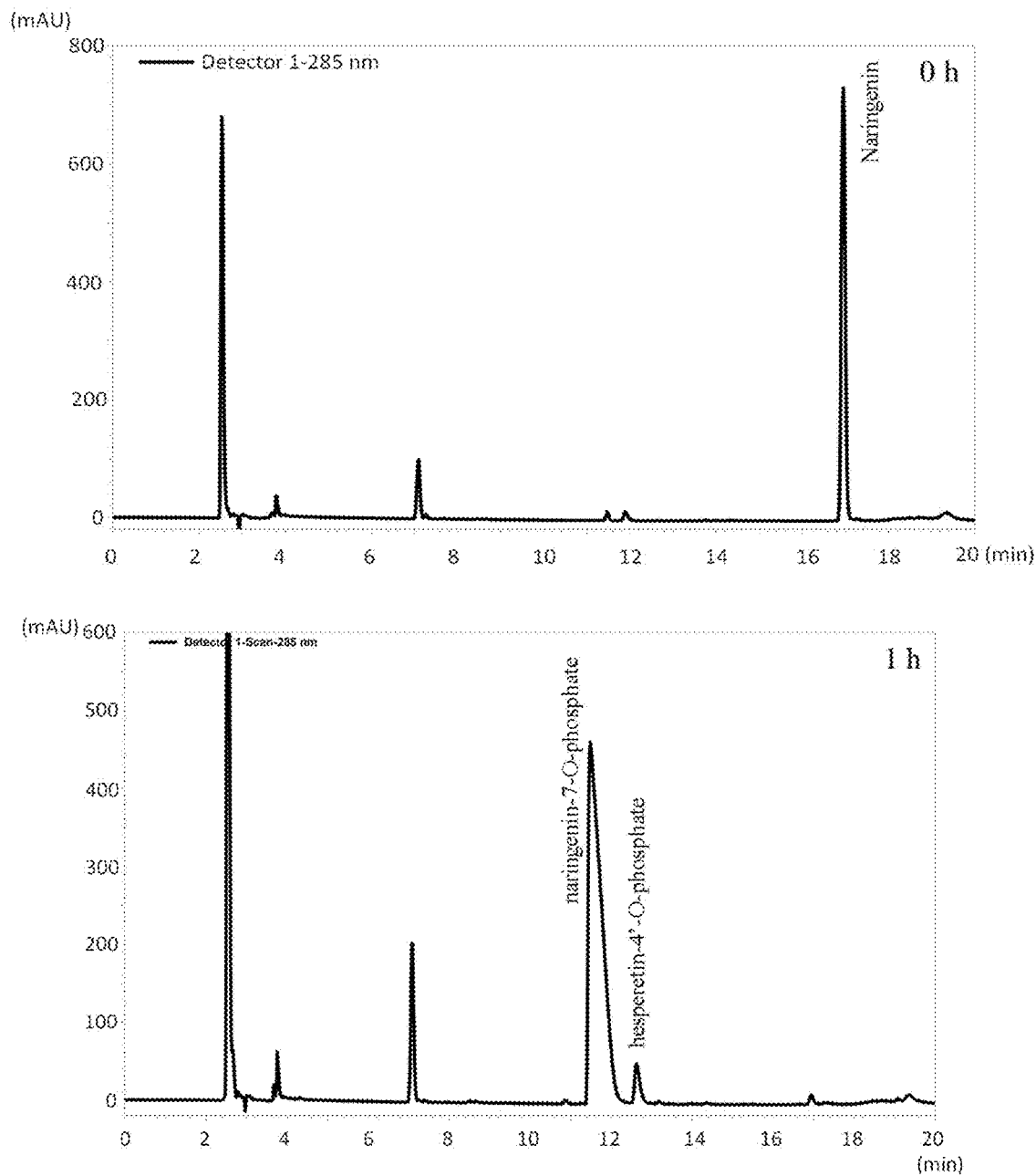
FIG. 9a-9c are the HPLC chromatograms of example 4 for the reaction of naringenin and benzopyrone phosphate synthetase.
Figure 9B:
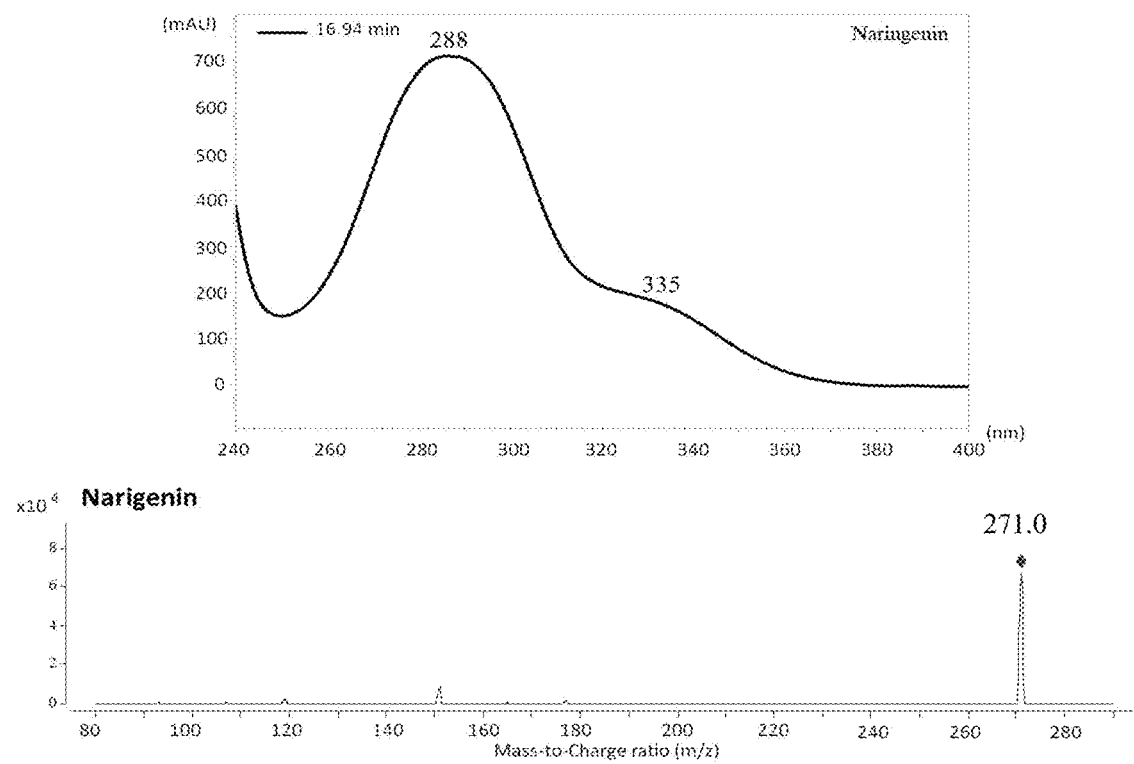
Figure 9C:
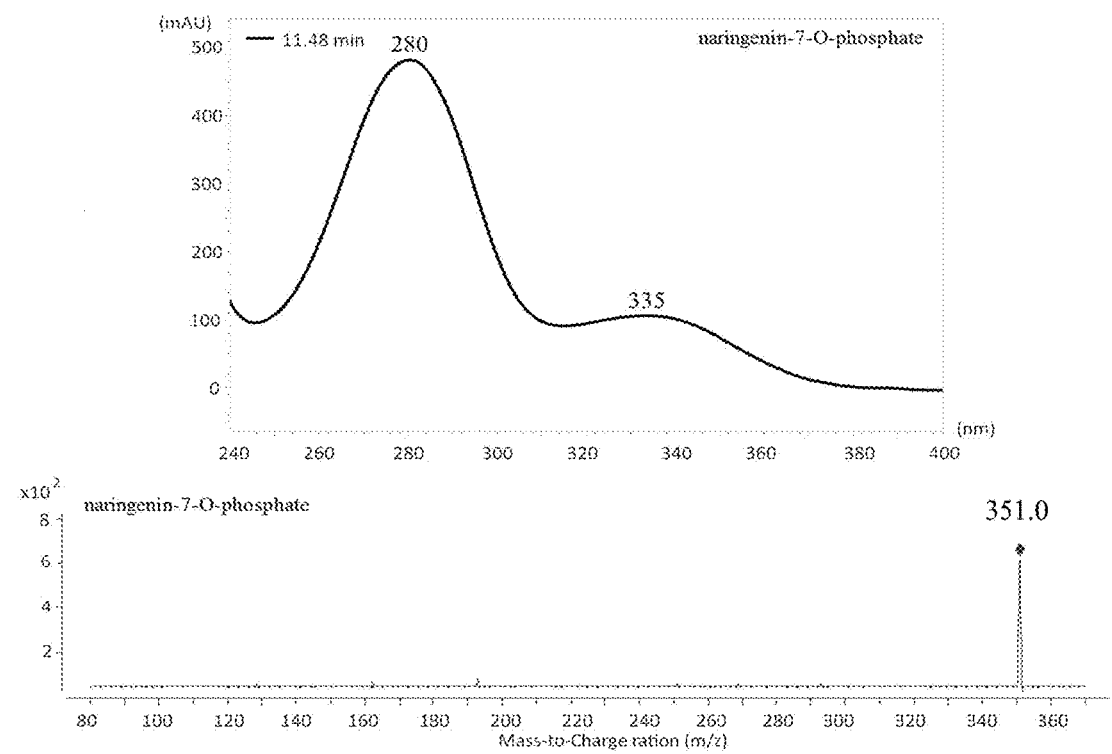
Figure 10A:
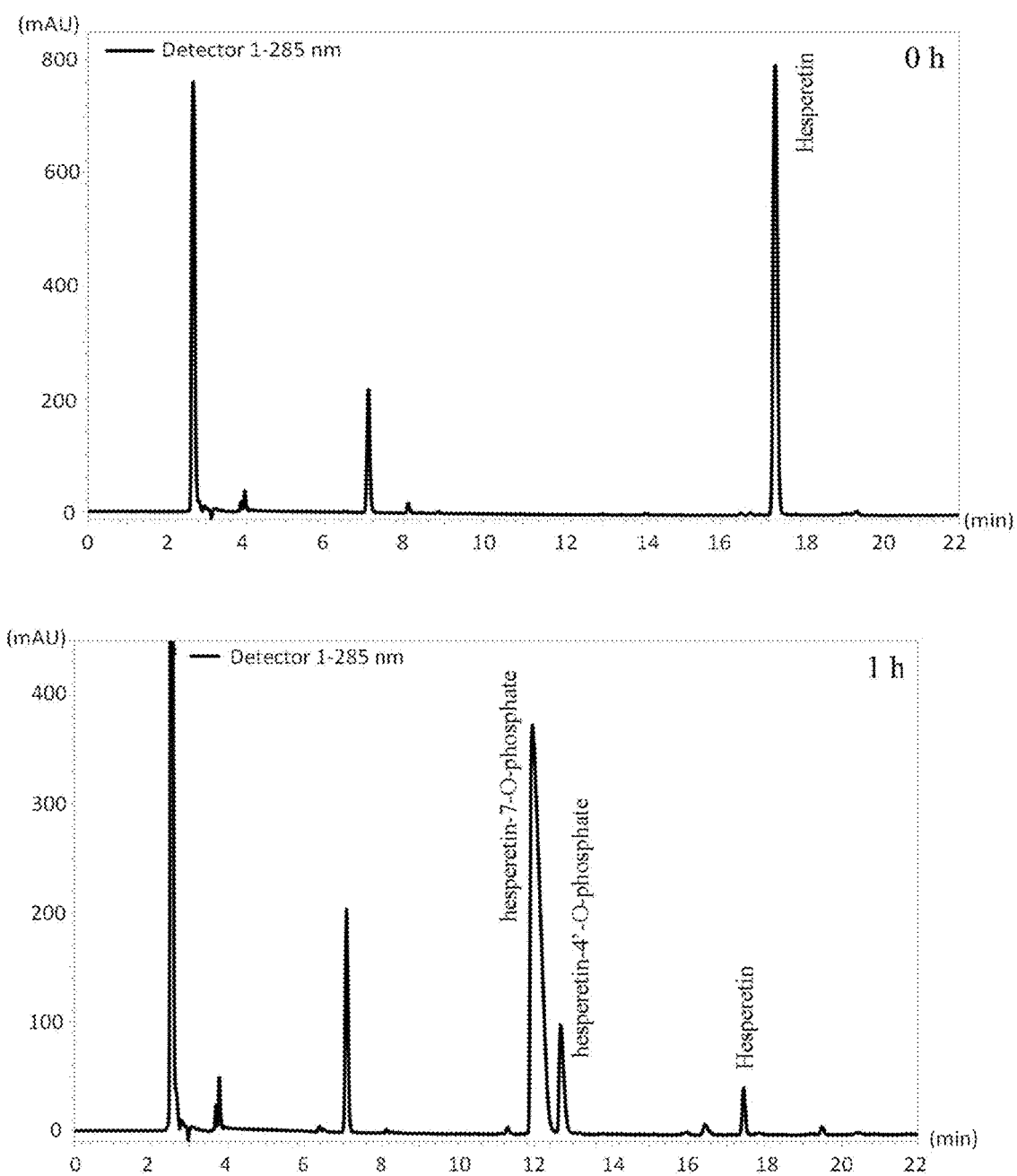
FIG. 10a-10d are the HPLC chromatograms of example 4 for the reaction of hesperetin and benzopyrone phosphate synthetase.
Figure 10B:
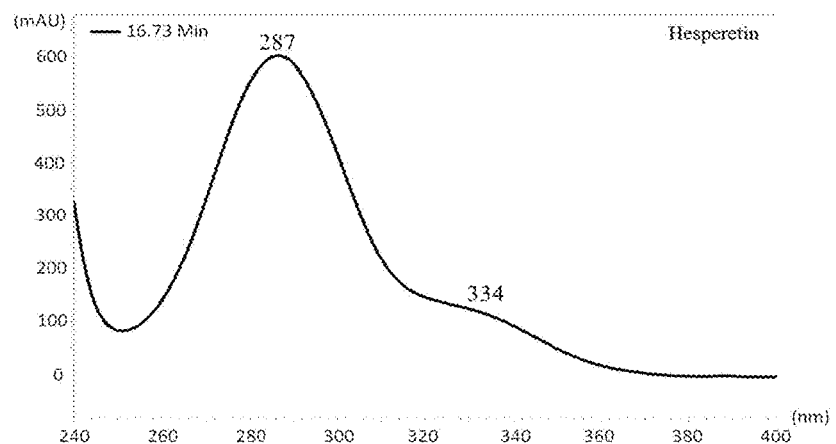
Figure 10B:
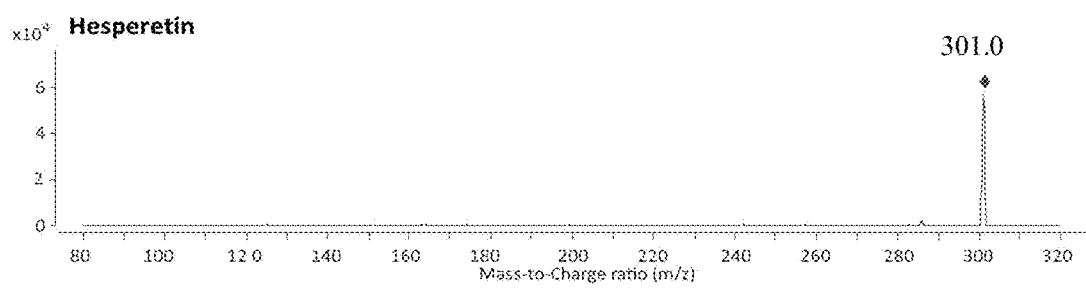
Figure 10C:
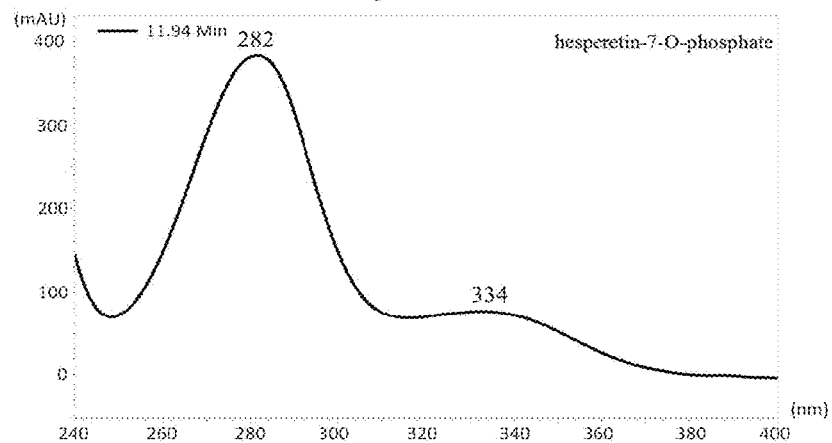
Figure 10C:
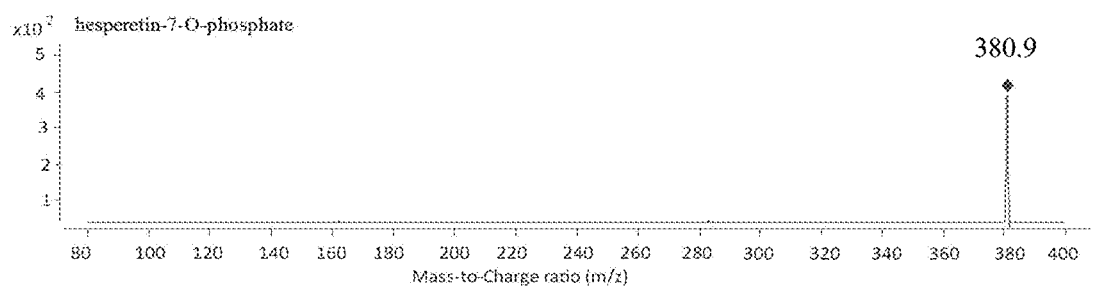
Figure 10D:
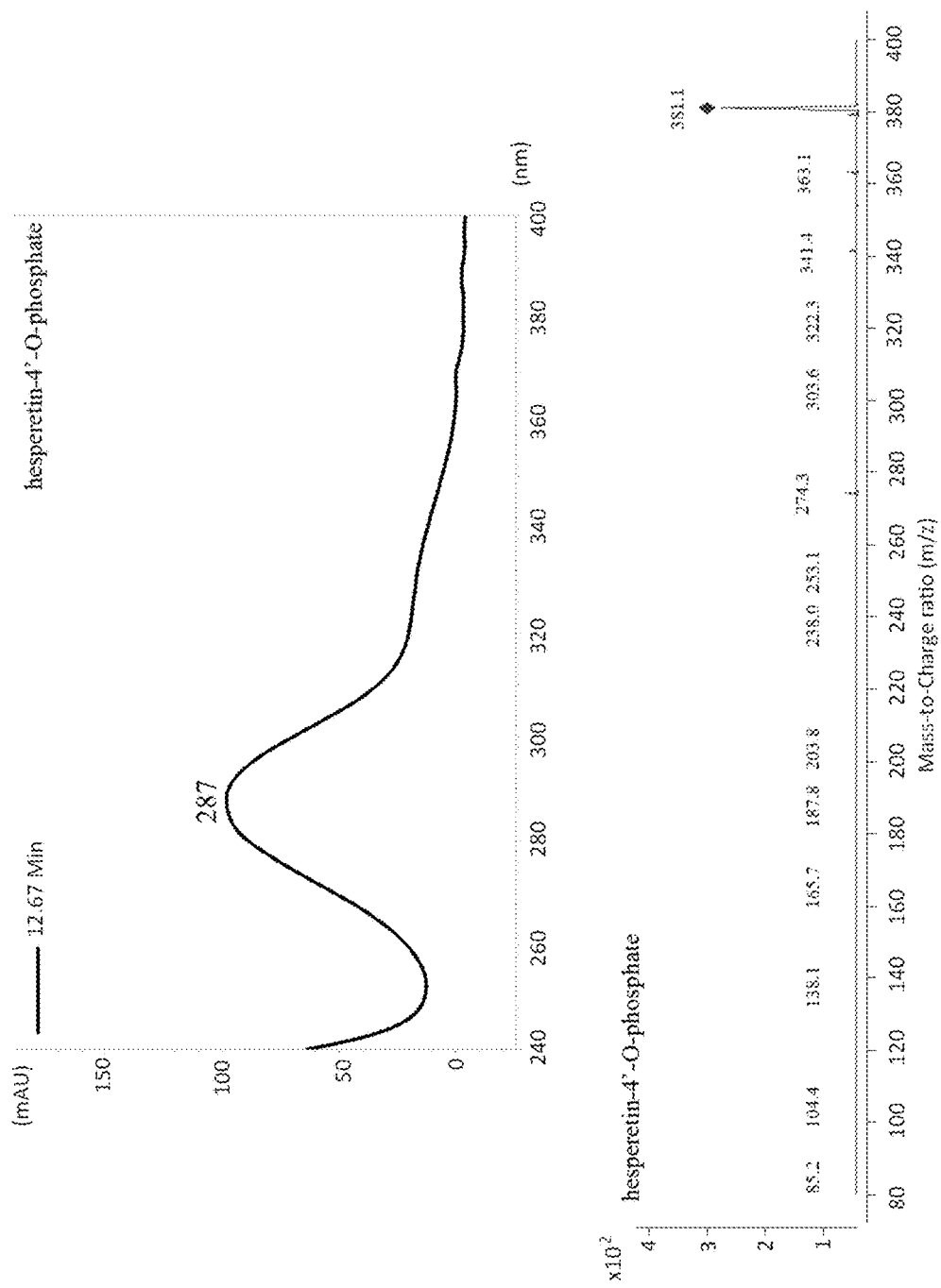
Figure 11A:
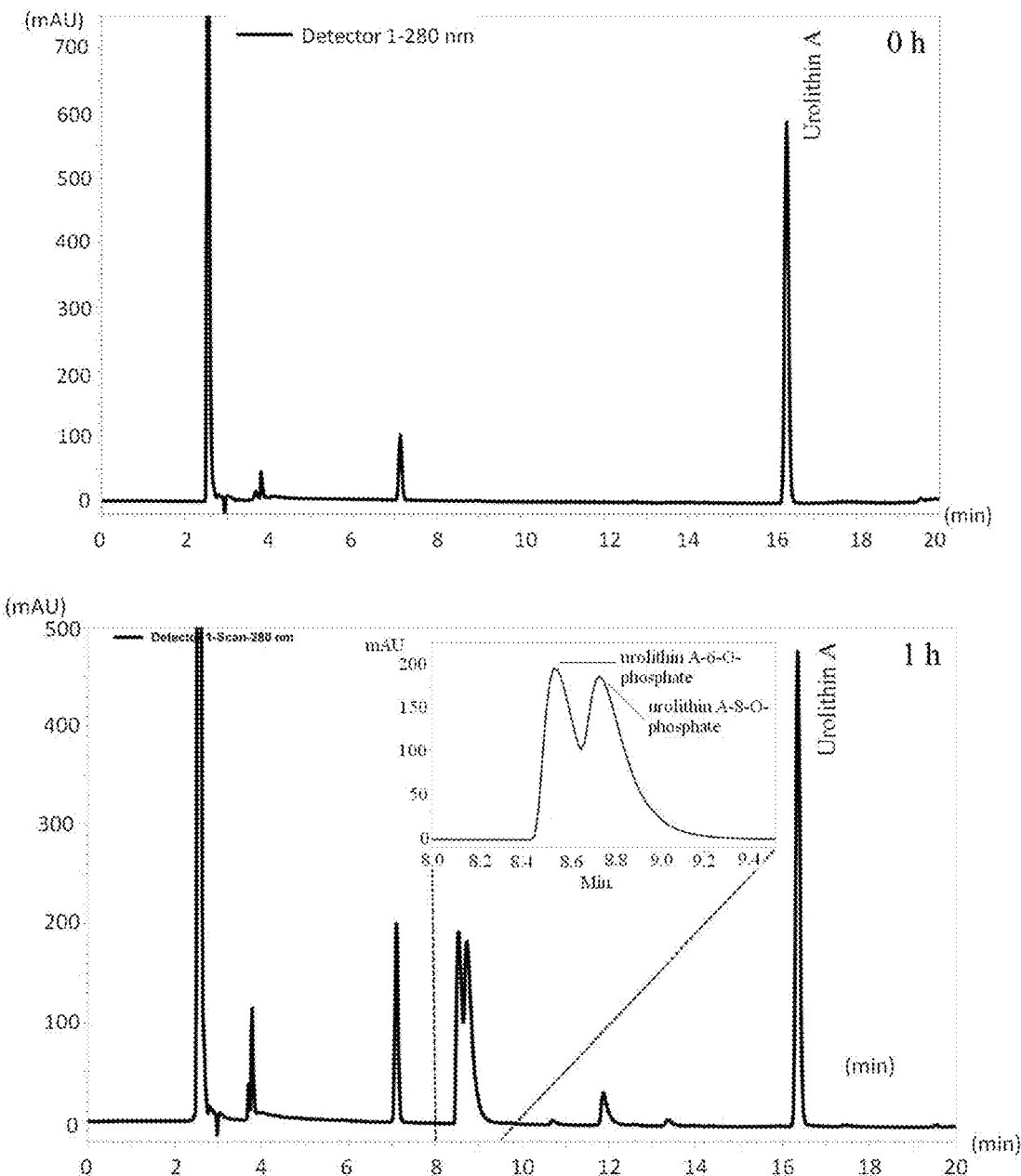
FIG. 11a-11d are the HPLC chromatograms of example 5 for the reaction of urolithin A and benzopyrone phosphate synthetase.
Figure 11B:
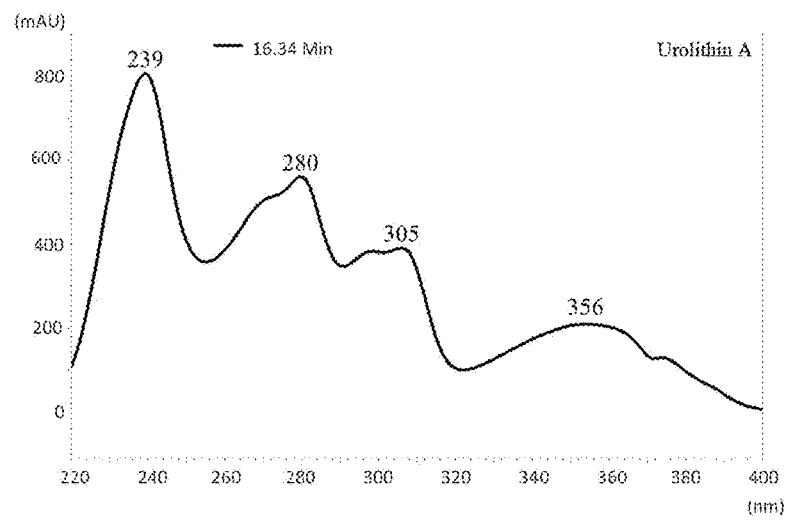
Figure 11C:
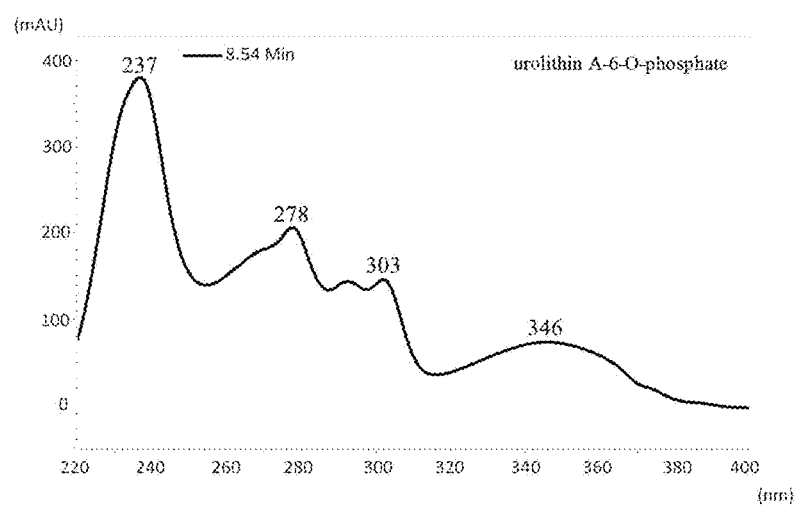
Figure 11D:
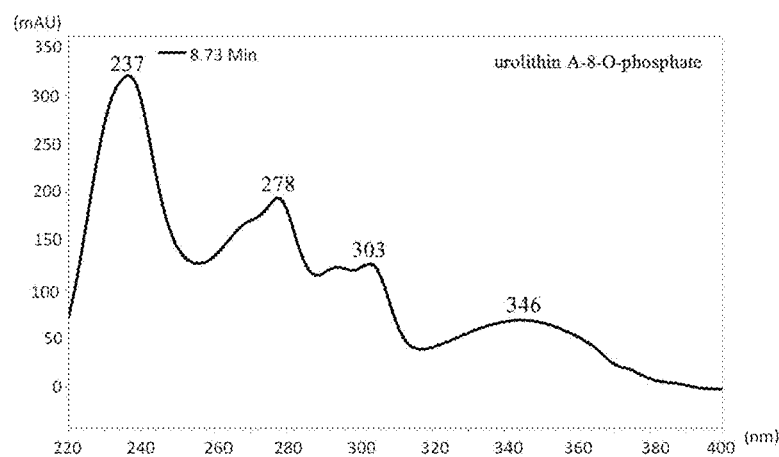

FIGS. 9 and 10 are described together as followed.

Naringenin and hesperetin have low solubility, which is 45 and 1.4 μg/mL, respectively. They are both classified as Class 2 (low solubility, high penetration) substances in the BCS classification. FIGS. 9 and 10 depict the spectral information (UV absorption spectrum and ESI-MS spectrum of parent ion and fragment ion) of the derivatives generated by reaction between benzopyrone phosphate synthetase and flavanones.

The reaction between naringenin and benzopyrone phosphate synthetase generates naringenin-7-O-phosphate, as described in Formula 7.

Formula 7

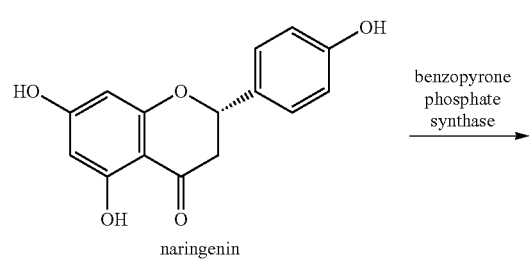

naringenin naringenin-7-O-phosphate

Hesperetin reacted with benzopyrone phosphate synthetase and generated hesperetin-7-O-phosphate and hesperetin-4'-O-phosphate. The hesperetin-7-O-phosphate is in the following Formula 8. After hesperetin reacts with benzopyrone phosphate synthetase, hesperetin-7-O-phosphate and hesperetin-4'-O-phosphate are synthesized. The synthesis of hesperetin-7-O-phosphate is illustrated in Formula 8.

Formula 8

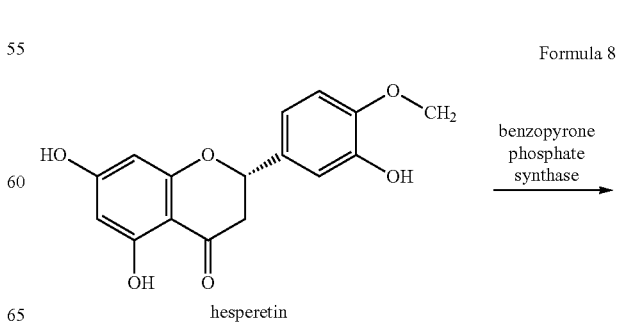

hesperetin

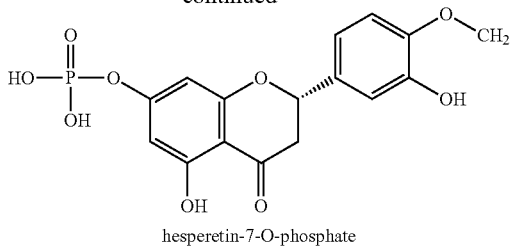

hesperetin-7-O-phosphate

Figure 12A:
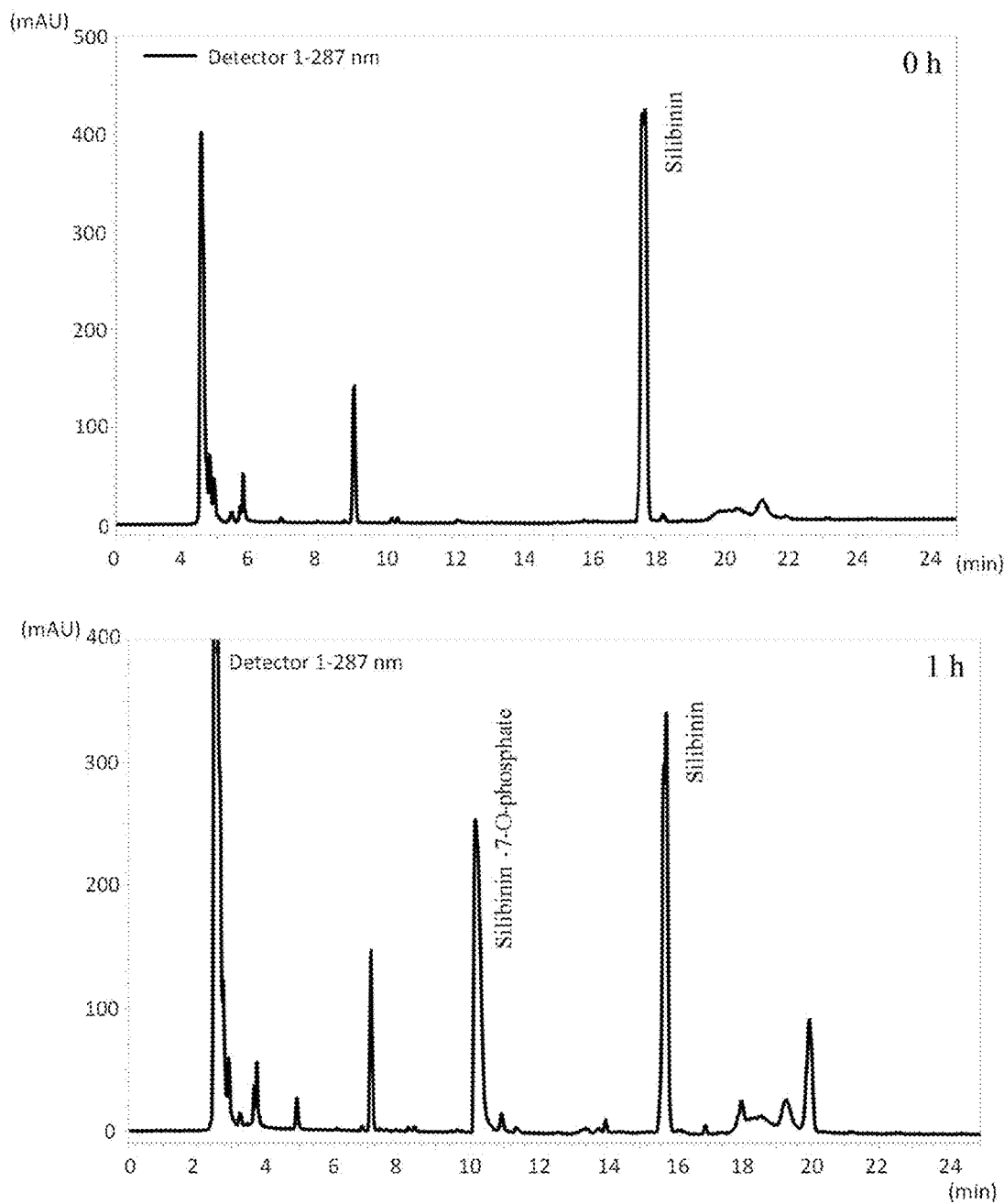
FIG. 12a-12c are the HPLC chromatograms of example 5 for the reaction of silibinin and benzopyrone phosphate synthetase.
Figure 12B:
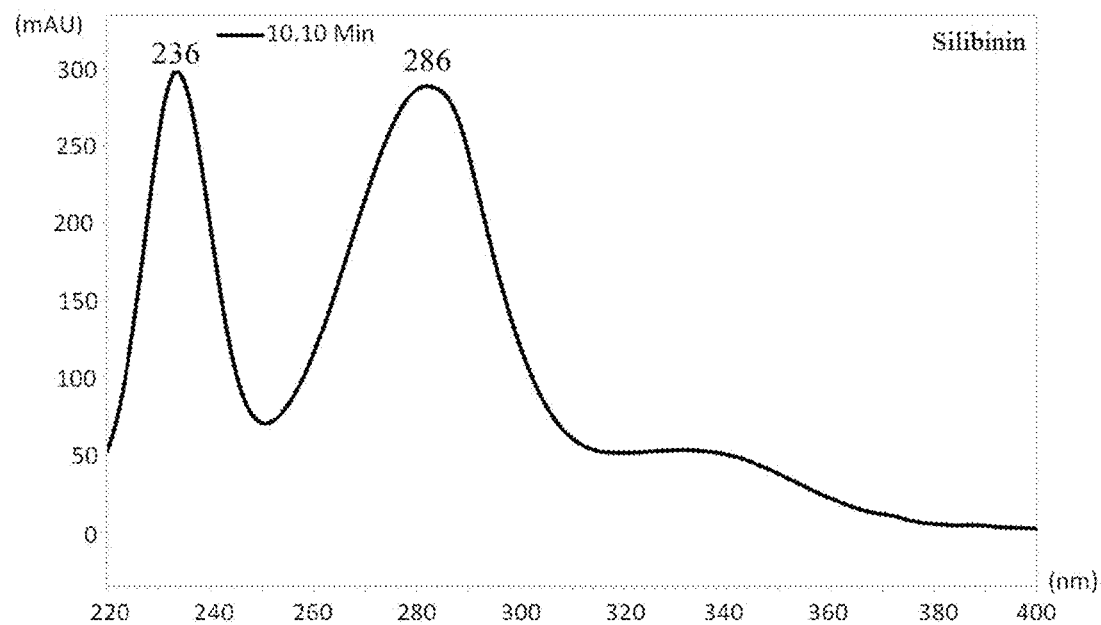
Figure 12C:
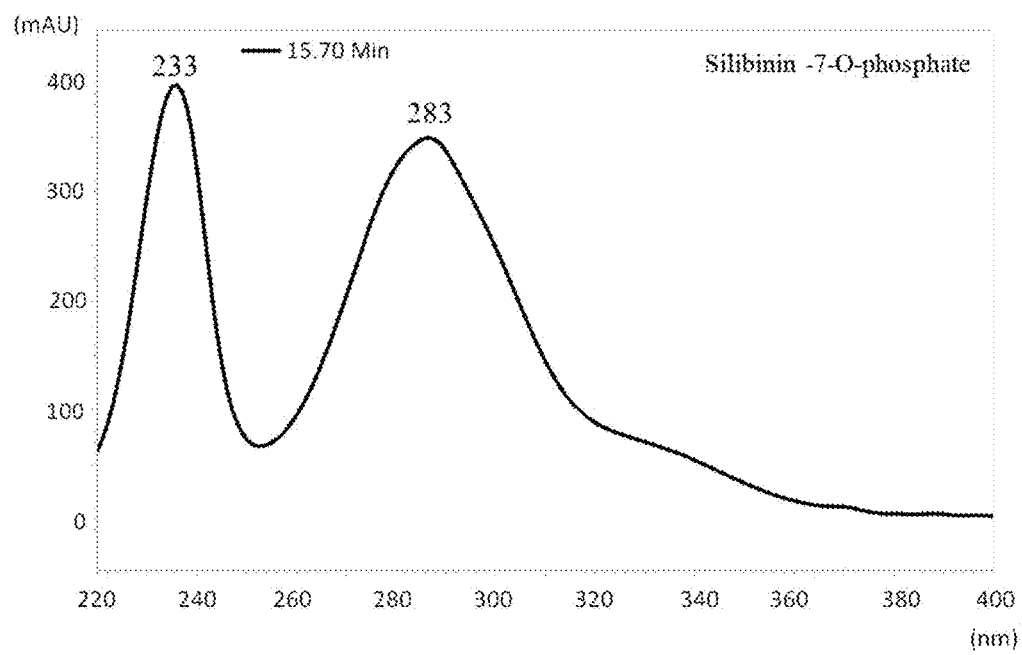

[Example 5] Reactions of Benzopyrone Phosphate Synthetase with Urolithin a and Silibinin FIGS. 11 and 12 are described together as followed.

Urolithin A and silibinin have low solubility, less than 40 μg/mL, and thus are classified as Class 2 (low solubility, high penetration) substances in the BCS classification. The spectral information of the generated derivatives by reaction of urolithin A and silibinin with benzopyrone phosphate synthetase is showed in FIGS. 11 and 12, which are UV absorption spectrum and ESI-MS spectrum of parent ion and fragment ion.

Urolithin A reacted with benzopyrone phosphate synthetase and generated urolithin A-6-O-phosphate and urolithin A-8-O-phosphate, as the following Formula 9.

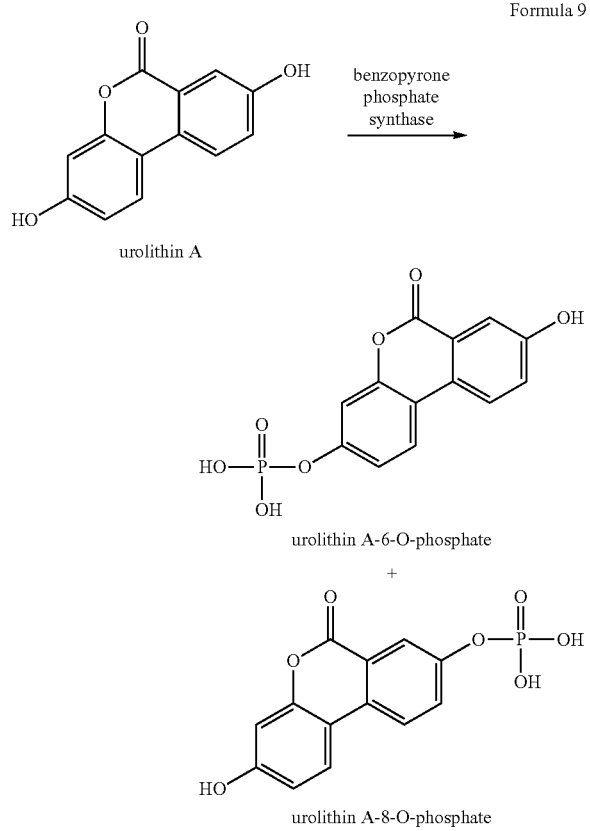

Formula 9

After silibinin reacts with benzopyrone phosphate synthetase, silibinin-7-O-phosphate is generated, as shown in Formula 10.

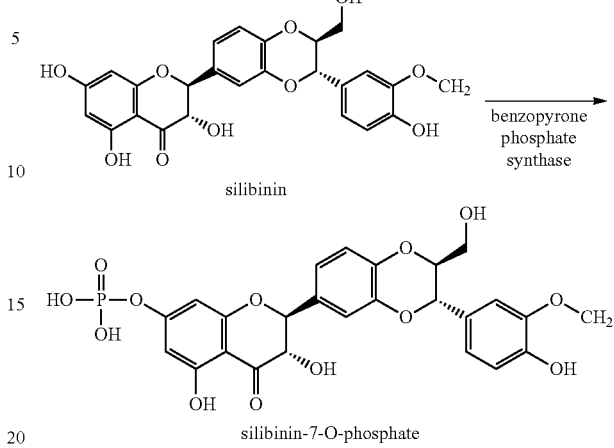

Formula 10

According to the above results, it is concluded that compounds that can be phosphorylated by benzopyrone phosphate synthetase must have chromen-4-one or chroman-4-one as their main structures. The additional OH group on the benzene ring of chromone can be phosphorylated by the enzyme.

The polypeptide of the present invention sequentially comprised (a) ATP binding domain, (b) substrate binding domain, and (c) mobile catalyzing domain, of which the nucleic acid sequences are SEQ ID NO:4, SEQ ID NO: 5, and SEQ ID NO: 6, respectively. The nucleic acid sequence of the polypeptide of the present invention and that of uncharacterized phosphotransferase YvkC [B. subtilis subsp. natto BEST195](Gene ID: 14103593) disclosed on NCBI web are different in five nucleotides. Though the sequence of uncharacterized phosphotransferase YvkC exists in nature, it is not in isolated or purified form. The present invention isolates and purifies the polypeptide from nature for the first time, and finds out that it has activity of benzopyrone phosphate synthetase. Although yvkC protein in B. Subtilis has been disclosed on the NCBI as uncharacterized phosphotransferase, but it is mere anticipation and no experiments have ever shown that it has activity of phosphotransferase. In fact, there were neither studies on benzopyrone phosphate synthetase, nor publication related to production of benzopyrone phosphate by microorganisms or synthesis of benzopyrone compounds by enzymatic phosphorylation prior to the present invention.

Moreover, in general, the phosphorylation substrates of phosphorylase and kinase are usually carbohydrates or proteins. However, the benzopyrone phosphate synthetase of the present invention can transfer phosphate to OH group of benzopyrone compounds. The benzopyrone phosphate synthetase should be classified as EC 2.7.9 according to its biochemical characteristic, but no other enzymes that can phosphorylate similar substrates as the present invention is found in that category, not to mention that no information related to its substrates and mechanism has been disclosed on the NCBI website.

Though many studies have demonstrated that flavonoids have good physiological activity, such as anti-oxidation, anti-inflammatory and antitumor activity, their bioavailability is poor due to their low solubility, i.e., Classes 2 or 4 in the BCS classification. In the present invention, the benzopyrone phosphate synthetase is isolated from B. subtilis BCRC 19679, which can phosphorylate benzopyrone compounds, especially flavonoid compounds such as isoflavone, flavone, flavonol and flavanone. The water solubility of flavonoid compounds is much higher, so does their bioavailability and biological activity of benzopyrone compounds. Recently, many health supplements are sold in the form of beverage. Since the benzopyrone phosphates are water-soluble flavonoids, they can be used as liquid formulation in beverage. Therefore, the present invention has great potential to be applied to the development of new forms of health supplement and pharmaceuticals, and is promising in the health industry in the future.

What is claimed is:
1. A method for producing benzopyrone phosphate derivatives, comprising: using
(1) an isolated polypeptide, classified in EC 2.7.9, being a benzopyrone phosphate synthetase and obtained from *Bacillus subtilis*, comprising the following amino acid sequences (a), (b), and (c) sequentially:
 (a) the amino acid sequence of ATP binding domain of SEQ ID NO: 2;
 (b) the amino acid sequence of substrate binding domain of SEQ ID NO: 1; and
 (c) the amino acid sequence of mobile catalyzing domain of SEQ ID NO: 3; or
(2) a microorganism having a nucleic acid sequence encoding the said isolated polypeptide, to contact or to cultivate with a benzopyrone compound.

2. The method according to claim 1, wherein the benzopyrone phosphate synthetase catalyzes phosphorylation of a benzopyrone compound.

3. The method according to claim 1, wherein the benzopyrone compound is selected from the group consisting of the following formula (I), (II), (III), (IV) and (V):

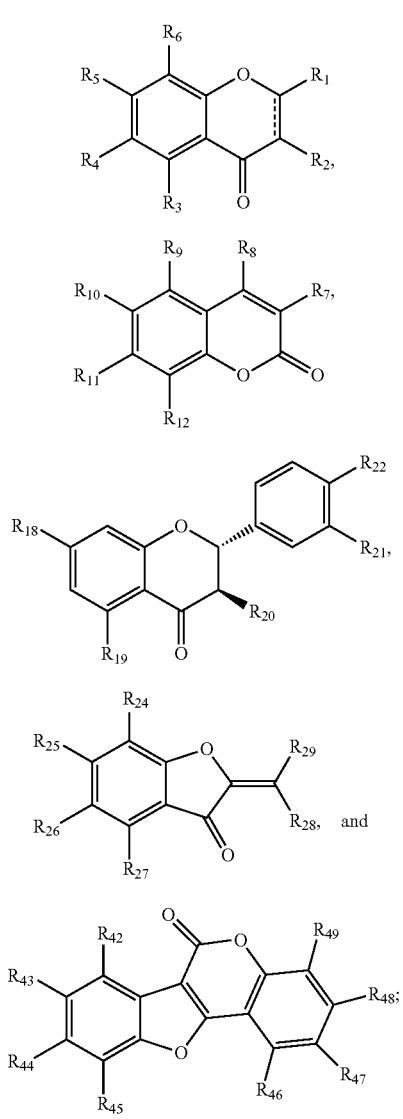

wherein $R_1$ and $R_2$ are independently selected from H, OH,

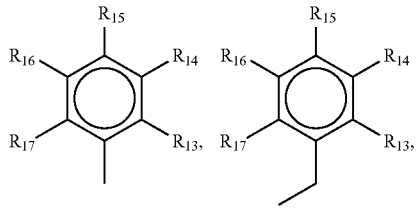

or $R_1$ and $R_2$ are fused to form $C_3$-$C_6$ cycloalkyl or $C_6$-$C_{10}$ aryl group, $R_3$, $R_4$, $R_6$, $R_9$, $R_{10}$, $R_{12}$, with $R^{15}$, $R^{16}$ and $R^{17}$ are H, OH, or $OCH_3$;

$R_5$ and $R_{11}$ are OH;

$R_7$ and $R_8$ are independently selected from H, OH, $OCH_3$, or $R_7$ and $R_8$ are fused to form $C_3$-$C_6$ cycloalkyl or $C_6$-$C_0$ aryl group, and optionally substituted by OH;

$R_{13}$ and $R_{14}$ are independently selected from H, OH, $OCH_3$, or

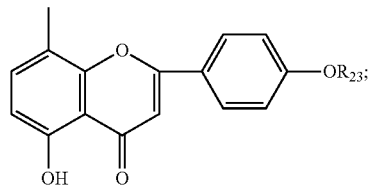

$R_{21}$ and $R_{22}$ are independently selected from hydrogen atom, halogen atom, nitro group, $(C_1$-$C_6)$alkyl, $(C_1$-$C_6)$alkylCOOH, $(C_1$-$C_6)$alkylCOONa, trifluoro$(C_1$-$C_6)$alkyl, $(C_3$-$C_6)$cycloalkyl, acyl, $(C_2$-$C_6)$alkenyl, $(C_2$-$C_6)$alkynyl, $(C_6$-$C_{18})$aryl, $(C_6$-$C_{18})$arylCOOH, $(C_6$-$C_{18})$arylCOONa, $(C_6$-$C_{18})$aryl$(C_1$-$C_4)$alkyl, $(C_1$-$C_6)$alkyl$(C_6$-$C_{18})$aryl, $(C_6$-$C_{18})$heteroaryl containing 1 to 3 heteroatoms, $CH(OH)(C_6$-$C_{18})$aryl, $CO(C_6$-$C_1)$aryl, $(CH_2)_n$CONH—$(CH_2)$ $(C_6$-$C_{18})$aryl, $(CH_2)_n$SO$_2$NH—$(CH_2)_m$C$_6$-$C_{18}$aryl or $(CH_2)_n$CONH—CH(COOH)—$(CH_2)_p$—$(C_6$-$C_{18})$aryl group, wherein n is 1 to 4, m is 0 to 3 and p is 0 to 2, or $OR_x$, $SR_x$, $NR_xR_y$, wherein (i) $R_x$ and $R_y$, independent of each other, are chosen from a hydrogen atom and $(C_1$-$C_6)$alkyl, $(C_3$-$C_6)$cycloalkyl, $(C_6$-$C_{18})$aryl, $(C_6$-$C_{18})$aryl$(C_1$-$C_4)$alkyl, $(C_1$-$C_{12})$alkyl$(C_6$-$C_{18})$aryl, $(C_3$-$C_6)$cyclo-alkyl$(C_6$-$C_{12})$aryl, $(C_5$-$C_{12})$heteroaryl containing 1 to 3 heteroatoms, NR'R" and NHCOR'R" groups, where in R' and R", independent of each other, are chosen from a hydrogen atom and $(C_1$-$C_6)$alkyl, $(C_3$-$C_6)$cycloalkyl and $(C_6$-$C_{12})$aryl groups, and aromatic or non-aromatic $(C_5$-$C_{12})$heterocycles, containing 1 to 3 heteroatoms, or (ii) $R_x$ and $R_y$ together form a linear or branched hydrocarbon-based chain containing 2 to 6 carbon atoms, optionally comprising one or more double bonds and/or optionally include an oxygen, sulfur or nitrogen atom;

$R_{23}$ is H or $CH_3$;

≡ is a single bond or a double bond;

$R_{24}$, $R_{26}$, and $R_{27}$ are independently selected from H, $(C_1$-$C_5)$alkyl, hydroxyl, $OR_{30}$, $OCH_2OR_{31}$, $OCOR_{32}$, $COR_{33}$, $CO_2R_{34}$, $OCH_2COOR_{35}$, $OCH_2(OR_{36})_2$, $OC=ONHR_{37}$, halogen, nitro, amino, $NR_{38}R_{39}$, cyano, mercapto, $SR_{40}$, $S(O)_qR_{41}$, $(C_1$-$C_5)$chloroalkyl, ($C_1$-$C_5$)haloalkoxy, ($C_2$-$C_6$)alkenyl, ($C_2$-$C_6$)alkynyl, ($C_3$-$C_{10}$)cycloalkyl, ($C_6$-$C_{11}$)phenyl, or ($C_7$-$C_{12}$)benzyl, wherein q is an integral of 1 to 3;

$R_{25}$ is OH;

$R_{28}$ is H, ($C_1$-$C_3$)alkyl, ($C_1$-$C_3$)alkoxy, ($C_1$-$C_3$)chloroalkoxy, halogen, nitro, amino, cyano, mercapto, or hydroxyl;

$R_{29}$ is five member ring or six member ring, including benzene, pyridine, furan, thiophene, pyrrole, thiazole, pyridazine, or pyrimidine;

$R_{42}$, $R_{44}$, $R_{45}$, $R_{46}$, $R_{47}$, and $R_{49}$ are independently selected from H, ($C_1$-$C_5$)alkyl, hydroxyl, $OR_{30}$, $OCH_2OR_{31}$, $OCOR_{32}$, $COR_{33}$, $CO_2R_{34}$, $OCH_2COOR_{35}$, $OCH_2(OR_{36})_2$, $OC$=$ONHR_{37}$, halogen, nitro, amino, $NR_{38}R_{39}$, cyano, mercapto, $SR_{40}$, $S(O)_rR_{41}$, ($C_1$-$C_5$)chloroalkyl, ($C_1$-$C_5$)haloalkoxy, ($C_2$-$C_6$)alkenyl, ($C_2$-$C_6$)alkynyl, ($C_3$-$C_{10}$)cycloalkyl, ($C_6$-$C_{11}$)phenyl, or ($C_7$-$C_{12}$)benzyl, wherein r is an integral of 1 to 3;

$R_{43}$ and $R_{48}$ are OH;

$R_{30}$ and $R_{31}$ are independently selected from ($C_1$-$C_5$) alkyl, ($C_1$-$C_5$)haloalkyl, ($C_2$-$C_6$)alkenyl, ($C_2$-$C_6$)alkynyl, ($C_6$-$C_{11}$)phenyl, or ($C_7$-$C_{12}$)benzyl;

$R_{32}$ is ($C_1$-$C_5$)alkyl, ($C_1$-$C_5$)haloalkyl, ($C_6$-$C_{11}$)phenyl, or ($C_7$-$C_{12}$)benzyl;

$R_{33}$ is ($C_1$-$C_5$)alkyl, ($C_1$-$C_5$)haloalkyl, ($C_2$-$C_6$)alkenyl, ($C_2$-$C_6$)alkynyl, ($C_6$-$C_{11}$)phenyl, or ($C_7$-$C_{12}$)benzyl;

$R_{34}$, $R_{35}$, $R_{36}$ and $R_{37}$ are independently selected from ($C_1$-$C_5$)alkyl or ($C_1$-$C_5$)haloalkyl;

$R_{38}$ and $R_{39}$ are independently selected from H, ($C_1$-$C_5$) alkyl or ($C_1$-$C_5$)haloalkyl, wherein only one of $R_{38}$ and $R_{39}$ is H; and, $R_{40}$ and $R_{41}$ are independently selected from ($C_1$-$C_5$)alkyl or ($C_1$-$C_5$)haloalkyl.

4. The method of claim 1, wherein the benzopyrone compound is flavonol, flavone, flavanone, flavonoids lignans, isoflavones, or coumarin.

5. The method of claim 4, wherein the microorganism is *Bacillus subtilis*.

\* \* \* \* \*

SEQUENCE LISTING

```
<160> NUMBER OF SEQ ID NOS: 14

<210> SEQ ID NO 1
<211> LENGTH: 449
<212> TYPE: PRT
<213> ORGANISM: Bacillus subtilis
<220> FEATURE:
<221> NAME/KEY: DOMAIN
<222> LOCATION: (1)..(449)

<400> SEQUENCE: 1
```

Ser Phe Met Ile Thr Asp Thr Asp Met Asn Asp Phe Trp Leu Asn Met
1               5                   10                  15

Glu Ser Asn Ile Glu Gly Pro Val Ser Pro Leu Phe Ser Ser Phe Ile
            20                  25                  30

Val Pro Ala Leu Glu Tyr Gly Leu Lys Lys Ser Met Gln Lys Phe Pro
        35                  40                  45

Ile Gly Val Val Val Asp Glu Val Lys Leu Tyr Arg Gly His Ile Tyr
    50                  55                  60

Ser Lys Asn Gln Gly Gly Gln Gln Pro Pro Ser Glu Asp Cys Gly Lys
65                  70                  75                  80

Glu Leu Phe Pro Ile Leu Ser Glu His Met Tyr Asp Ile Ile Asn His
                85                  90                  95

Thr Tyr Leu Pro Phe Tyr Arg Thr Leu Asp Gln Leu Ala Gln Thr Glu
            100                 105                 110

His Thr Ala Glu Ser Ala Leu Asp Ala Phe Gln Lys Leu Lys Ala Phe
        115                 120                 125

Tyr Leu Thr Ala Tyr Glu Glu His Phe Asn Ile Val Phe Pro Gln Ile
    130                 135                 140

Leu Leu Thr Asn Lys Leu Gln Ala Met Tyr Gln Asp Ile Gln Gly Glu
145                 150                 155                 160

Ser Glu Asn Ala His Phe Tyr Glu Met Leu Thr Gly Lys Met Asn Lys
                165                 170                 175

Ser Leu Glu Thr Asp Arg Cys Leu Trp Leu Phe Ser Met Glu Val Gln
            180                 185                 190

Glu Asn Pro Asn Leu Leu Thr Ile Phe Glu Asn Asn Lys Pro Glu Gln
        195                 200                 205

Leu Gln Glu Lys Leu Glu Gln Thr Asp Glu Gly Arg His Phe Leu Lys
    210                 215                 220

Asn Val His Glu Phe Leu Gln Glu Tyr Gly Trp Arg Ser Val Lys Ser
225                 230                 235                 240

His Asp Leu Ile Glu Gln Ile Trp Val Glu Asn Pro Tyr Phe Ala Leu
                245                 250                 255

Ala Asn Ile Gln Asn Tyr Val Arg Asn Gly Tyr His Phe Asp Asn Glu
            260                 265                 270

Phe Gln Lys Thr Lys Glu Lys Arg Glu Lys Leu Tyr Asn Glu Phe Leu
        275                 280                 285

Glu Asn Ile Glu Asp Pro Gly Leu Arg Thr Glu Phe Asp Arg Tyr Tyr
    290                 295                 300

Gln Trp Thr Leu Asn Ser Ala Asn Ile Lys Asp Asp His His Phe Tyr

```
            305                 310                 315                 320
Ile Asp Ala Met Leu Asp Ala Lys Ala Arg Ile Phe Leu Leu Lys Ile
                325                 330                 335

Gly Glu Leu Leu Ala Glu Asn Gly Val Ile Gln Asp Arg Glu Asp Leu
                340                 345                 350

Trp Phe Leu Tyr Asp Asp Val Glu Gln Ala Leu Leu His Pro Val
                355                 360                 365

Ser Leu Gln Glu Lys Ala Glu Lys Arg Arg Gln Ile Phe His Glu Tyr
370                 375                 380

Glu Leu Ala Gln Ala Pro Ala Tyr Leu Gly Thr Pro Thr Lys Glu Gln
385                 390                 395                 400

Leu Lys Ala Ala Glu Glu Ile Val Gly Ala Val Ile Glu Asp Glu Lys
                405                 410                 415

Asn Thr Glu Asn His Ile Phe Gly Ile Ala Ala Ser Ser Gly Ile Ala
                420                 425                 430

Thr Gly Pro Val Lys Ile Ile Arg Asp Ala Asn Glu Phe Ser Gln Phe
                435                 440                 445

Ala
```

<210> SEQ ID NO 2
<211> LENGTH: 289
<212> TYPE: PRT
<213> ORGANISM: Bacillus subtilis
<220> FEATURE:
<221> NAME/KEY: DOMAIN
<222> LOCATION: (1)..(289)

<400> SEQUENCE: 2

```
Ala Gly Ala Lys Gly Met Asn Leu Ile Lys Leu Thr Lys His Gly Leu
1               5                   10                  15

Pro Val Pro Asp Gly Phe Ile Ile Gln Thr Asn Ala Leu Ala Arg Phe
                20                  25                  30

Met Glu Asp Asn Gln Leu Gln Glu Thr Ser Glu Asn Val Glu Ser Gly
                35                  40                  45

Ile Ile Ser Gly Thr Phe Ser Asp Glu Leu Lys Asp Glu Leu Thr Ser
                50                  55                  60

Ser Phe Tyr Lys Leu Arg Glu Ser Tyr Arg Ser Val Ala Val Arg Ser
65                  70                  75                  80

Ser Ser Ala Ser Glu Asp Leu Glu Gly Ala Ser Phe Ala Gly Gln Tyr
                85                  90                  95

Glu Thr Tyr Leu Asn Ile Lys Thr Glu Glu Glu Phe Leu Ala Lys Val
                100                 105                 110

Lys Glu Cys Trp Ala Ser Phe Phe Ser Gly Arg Val Ser Ser Tyr Lys
                115                 120                 125

Lys Lys Met Asn Asn Gln Ile Ala Glu Pro Leu Met Gly Ile Val Val
                130                 135                 140

Gln Gly Leu Ile Asp Ser Glu Met Ser Gly Val Ile Phe Ser Arg Asn
145                 150                 155                 160

Pro Val Thr His Asp Asp Arg Glu Leu Leu Ile Ser Ala Ser Tyr Gly
                165                 170                 175

Leu Gly Glu Ala Val Val Ser Gly Ser Val Thr Pro Asp Thr Phe Ile
                180                 185                 190

Val Asn Lys Ser Ser Phe Glu Ile Gln Lys Glu Ile Gly Ala Lys Glu
                195                 200                 205

Ile Tyr Met Glu Ser Ala Ala Glu Gly Ile Ala Glu Lys Glu Thr Ser
```

```
            210                 215                 220
Glu Asp Met Arg Ser Arg Phe Cys Leu Thr Asp Glu Gln Val Ile Glu
225                 230                 235                 240

Leu Ala Glu Ile Thr Lys Lys Thr Glu Asp Leu Tyr Gly Tyr Pro Val
                245                 250                 255

Asp Ile Glu Phe Gly Ile Ala Asp His Gln Ile Tyr Leu Leu Gln Ala
                260                 265                 270

Arg Pro Ile Thr Thr Ile Asp Gln Asp Lys Lys Ala Ala Glu Glu Lys
        275                 280                 285

Arg

<210> SEQ ID NO 3
<211> LENGTH: 70
<212> TYPE: PRT
<213> ORGANISM: Bacillus subtilis
<220> FEATURE:
<221> NAME/KEY: DOMAIN
<222> LOCATION: (1)..(70)

<400> SEQUENCE: 3

Pro Gly Asp Val Leu Val Cys Lys Met Thr Thr Pro Leu Trp Thr Ser
1               5                   10                  15

Leu Phe Gln Asp Ala Lys Ala Ile Ile Thr Asp Thr Gly Gly Ile Leu
                20                  25                  30

Ser His Ala Ala Ile Ile Ala Arg Glu Tyr Gly Ile Pro Ala Val Leu
            35                  40                  45

Gly Thr Arg Thr Ala Thr Glu Arg Leu Arg Asp Gly Asp Ile Ile Thr
        50                  55                  60

Val Asp Gly Ser Ser Gly
65                  70

<210> SEQ ID NO 4
<211> LENGTH: 1347
<212> TYPE: DNA
<213> ORGANISM: Bacillus subtilis
<220> FEATURE:
<221> NAME/KEY: Unsure
<222> LOCATION: (1)..(1347)

<400> SEQUENCE: 4
agcttcatga ttaccgacac tgatatgaat gatttctggc ttaacatgga gtctaatatt      60
gaaggtccgg tgagtccgtt attttcatcc ttcatcgtgc cggcattgga atatggcttg     120
aagaagagca tgcaaaagtt tccgattggt gtagttgttg atgaagtaaa actttatcgc     180
ggacatattt attccaaaaa ccaaggtgga cagcagcctc cttctgaaga ctgcggcaaa     240
gagcttttcc cgatttatc ggagcatatg tatgacatca tcaatcacac ataccctccct     300 ttttaccgga cactggacca gctcgcacaa actgagcata ccgcagaaag cgcactggat     360
gcttttcaaa aactaaaggc ctttatctc acggcttatg aagagcactt caatatcgtt     420
ttcccgcaaa tccttttaac aaacaaactg caagcgatgt atcaggacat tcaaggagag     480
tccgaaaacg ctcattttta tgagatgctg acaggaaaaa tgaacaaatc actggaaacg     540
gaccgttgct atggctatt ttctatggaa gttcaggaga acccgaacct tctgaccatt     600
tttgaaaaca acaagcctga acagctccag gagaaattag aacaaacaga tgaggggaga     660
cacttcctga agaacgtcca tgaattcttg caagaatacg gatggagatc tgttaaaagt     720
catgatctga ttgaacaaat ctgggtggaa aatccgtatt cgctctggc taatattcaa     780
```

```
aattatgtcc gtaatggcta tcattttgac aatgaatttc agaaaacgaa agaaaaacga      840
gagaaattat acaatgaatt cttggaaaac atagaagatc ccggtttgcg caccgaattt      900
gaccgctatt atcaatggac actgaactct gcaaatataa aagatgatca ccacttttat      960
attgacgcca tgctggatgc caaggcgaga atctttctgc tgaagatagg tgaattgctg     1020
gcggaaaacg gtgtcattca agatcgtgag gacctttggt ttttatatga cgacgaagtg     1080
gaacaagcgc ttcttcaccc tgtatccctg caagaaaagg ctgaaaaacg cagacagatt     1140
tttcatgagt atgagctggc ccaagcccct gcctacctcg gcaccccgac aaaagaacag     1200
ctcaaagcag ctgaagaaat tgtcggcgct gtgatagagg atgaaaaaaa cacagagaat     1260 catattttg gcattgcggc atcaagcggc attgcgacag gtccggtgaa aatcattcgg      1320
gacgccaatg aattttctca attcgcg                                         1347

<210> SEQ ID NO 5
<211> LENGTH: 936
<212> TYPE: DNA
<213> ORGANISM: Bacillus subtilis
<220> FEATURE:
<221> NAME/KEY: unsure
<222> LOCATION: (1)..(936)

<400> SEQUENCE: 5
atgaagaaaa gaggggtttc aaatatgtat tctgttttat ttcgccaggc agaagagtcc       60
agccagctgg ctggagcaaa aggaatgaat ttgattaaat tgaccaaaca cggtcttcct      120
gttccggacg ggtttattat tcaaacgaat gcgctcgcac gttttatgga ggacaaccag      180
cttcaagaga ctagtgaaaa cgtcgaaagc gggatcattt ctggaacatt ttcggatgag      240
ctgaaagatg agctgactag ttcctttat aagcttagag aatcatatcg atccgtagcc       300
gtgcgttctt cgtctgcttc ggaagattta gaaggcgcct cattcgcggg tcaatatgaa      360
acctacttaa atatcaaaac agaggaagag tttctggcta agtgaaaga atgctgggcc      420 tcattttttt ctgggcgggt cagcagctat aagaaaaaaa tgaacaatca aatcgcagag      480
ccgttaatgg aatagtcgt tcaggggctg atcgattcag aaatgtcagg tgttatcttc      540
agccgcaacc ctgttaccca tgatgataga gagctttta tcagcgccag ctacgggttg      600
ggtgaagctg ttgtttcagg aagtgttacc ccagacacgt tcattgttaa taaatcttcg      660
tttgagattc agaaagaaat aggtgcaaag gaaatctaca tggagtctgc ggcagaagga      720
attgctgaaa agaaacgag tgaagacatg cgcagccgtt tttgccttac agatgaacaa      780
gtgattgaat tggctgaaat cacaaaaaaa accgaagacc tgtacggata tcctgtcgat      840
atagaatttg gaattgctga tcatcaaata taccttctgc aagctcgccc gattacaacc      900
attgatcagg acaaaaaggc ggcagaagaa aaacgc                               936

<210> SEQ ID NO 6
<211> LENGTH: 237
<212> TYPE: DNA
<213> ORGANISM: Bacillus subtilis
<220> FEATURE:
<221> NAME/KEY: Unsure
<222> LOCATION: (1)..(237)

<400> SEQUENCE: 6
cctggggacg tactcgtttg caagatgacc acaccgctat ggaccagcct gtttcaagac       60
gccaaagcga taattacaga cacaggcggc attttgtctc acgctgcgat tattgcccgt      120
gaatacggca ttccagccgt tctcggcaca cgcacggcaa ccgaaagact gcgagacggt      180
```

```
gacatcatca ctgttgacgg tagcagcggc aaaatcacag ttgtcagccg gtcctga       237
```

<210> SEQ ID NO 7
<211> LENGTH: 449
<212> TYPE: PRT
<213> ORGANISM: Bacillus subtilis
<220> FEATURE:
<221> NAME/KEY: DOMAIN
<222> LOCATION: (1)..(449)

<400> SEQUENCE: 7

```
Ser Phe Met Ile Thr Asp Thr Asp Met Asn Asp Phe Trp Leu Asn Met
1               5                   10                  15

Glu Ser Asn Ile Glu Gly Pro Val Ser Pro Leu Phe Ser Ser Phe Ile
            20                  25                  30

Val Pro Ala Leu Glu Tyr Gly Leu Lys Lys Ser Met Gln Lys Phe Pro
        35                  40                  45

Ile Gly Val Val Val Asp Glu Val Lys Leu Tyr Arg Gly His Ile Tyr
    50                  55                  60

Ser Lys Asn Gln Gly Gly Gln Pro Pro Ser Glu Asp Cys Gly Lys
65                  70                  75                  80

Glu Leu Phe Pro Ile Leu Ser Glu His Met Tyr Asp Ile Ile Asn His
                85                  90                  95

Thr Tyr Leu Pro Phe Tyr Arg Thr Leu Asp Gln Leu Ala Gln Thr Glu
            100                 105                 110

His Thr Ala Glu Ser Ala Leu Glu Ala Phe Gln Lys Leu Lys Ala Phe
        115                 120                 125

Tyr Leu Thr Ala Tyr Glu Glu His Phe Asn Ile Val Phe Pro Gln Ile
    130                 135                 140

Leu Leu Thr Asn Lys Leu Gln Ala Met Tyr Gln Asp Ile Gln Gly Glu
145                 150                 155                 160

Ser Glu Asn Ala His Phe Tyr Glu Met Leu Thr Gly Lys Met Asn Lys
                165                 170                 175

Ser Leu Glu Thr Asp Arg Cys Leu Trp Leu Phe Ser Val Glu Val Gln
            180                 185                 190

Glu Asn Pro Asn Leu Leu Ala Ile Phe Glu Asn Asn Lys Pro Glu Gln
        195                 200                 205

Leu Gln Glu Lys Leu Glu Gln Thr Asp Glu Gly Arg His Phe Leu Lys
    210                 215                 220

Asn Val His Glu Phe Leu Gln Glu Tyr Gly Trp Arg Ser Val Lys Ser
225                 230                 235                 240

His Asp Leu Ile Glu Gln Ile Trp Val Glu Asn Pro Tyr Phe Ala Leu
                245                 250                 255

Ala Asn Ile Gln Asn Tyr Val Arg Asn Gly Tyr His Phe Asp Asn Glu
            260                 265                 270

Phe Gln Lys Thr Lys Glu Lys Arg Glu Lys Leu Tyr Asn Glu Phe Leu
        275                 280                 285

Glu Ser Ile Glu Asp Pro Gly Leu Arg Thr Glu Phe Asp Arg Tyr Tyr
    290                 295                 300

Gln Trp Thr Leu Asn Ser Ala Asn Ile Lys Asp His His Phe Tyr
305                 310                 315                 320

Ile Asp Ala Met Leu Asp Ala Lys Ala Arg Ile Phe Leu Leu Lys Ile
                325                 330                 335

Gly Glu Leu Leu Ala Glu Asn Gly Val Ile Gln Asp Arg Glu Asp Leu
            340                 345                 350
```

-continued

Trp Phe Leu Tyr Asp Asp Glu Val Glu Gln Ala Leu Leu His Pro Val
355 360 365

Ser Leu Gln Glu Lys Ala Glu Lys Arg Arg Gln Ile Phe His Glu Tyr
370 375 380

Glu Leu Ala Gln Ala Pro Ala Tyr Leu Gly Thr Pro Thr Lys Glu Gln
385 390 395 400

Leu Lys Ala Ala Glu Glu Ile Val Gly Ala Val Ile Glu Asp Glu Lys
405 410 415

Asn Thr Glu Asn His Ile Phe Gly Ile Ala Ala Ser Ser Gly Ile Ala
420 425 430

Thr Gly Pro Val Lys Ile Ile Arg Asp Ala Asn Glu Phe Ser Gln Phe
435 440 445

Ala

<210> SEQ ID NO 8
<211> LENGTH: 449
<212> TYPE: PRT
<213> ORGANISM: Bacillus tequilensis
<220> FEATURE:
<221> NAME/KEY: domain
<222> LOCATION: (1)..(449)

<400> SEQUENCE: 8

Ser Phe Met Met Thr Asp Ala Asp Met Lys Asp Phe Trp Ile Asn Met
1 5 10 15

Glu Ser Asn Ile Glu Gly Pro Val Ser Pro Leu Phe Ser Ser Phe Ile
20 25 30

Val Pro Ala Met Glu Tyr Gly Leu Lys Arg Asn Met Gln Lys Phe Pro
35 40 45

Leu Gly Ala Ile Ala Glu Glu Val Lys Leu Tyr Arg Gly His Ile Tyr
50 55 60

Ser Lys Asn Gln Gly Gly His Gln Pro Asp Glu Asp Cys Gly Lys Glu
65 70 75 80

Ile Phe Pro Ile Leu Ser Glu Arg Met Tyr Asp Ile Ile Lys His Thr
85 90 95

Tyr Leu Pro Phe Tyr Glu Thr Leu Asp Gln Leu Ala Gln Thr Asp His
100 105 110

Thr Ala Glu Ser Ala Leu Asp Ala Phe Arg Lys Leu Lys Ala Phe Tyr
115 120 125

Leu Arg Ala Tyr Asp Glu His Phe Asn Ile Val Phe Pro Gln Met Leu
130 135 140

Leu Thr Asn Lys Leu Arg Ala Met Tyr Gln His Ile Gln Gly Glu Ser
145 150 155 160

Glu Thr Ala His Phe Tyr Glu Met Leu Thr Gly Lys Met Asn Lys Ser
165 170 175

Leu Glu Thr Asp Arg Cys Leu Trp Leu Tyr Ser Val Glu Val Arg Glu
180 185 190

Asn Pro Asn Leu Leu Ala Ile Phe Glu Asn Thr Glu Pro Glu Gln Leu
195 200 205

Gln Glu Lys Leu Glu Gln Thr Asp Glu Gly Arg His Phe Leu Lys Asn
210 215 220

Ile His Glu Phe Leu Gln Asp Tyr Gly Trp Arg Ser Val Lys Ser His
225 230 235 240

Asp Leu Ile Glu Gln Ile Trp Ala Glu Asn Pro Tyr Phe Ala Leu Ala
245 250 255

```
Asn Ile Gln Asn Tyr Val Arg Asn Gly Tyr His Phe Asp Asn Glu Phe
            260                 265                 270

Gln Lys Thr Lys Glu Lys Arg Glu Lys Leu Tyr His Asp Phe Leu Glu
        275                 280                 285

Asn Ile Glu Asp Pro His Val Arg Glu Gln Phe Asp Gln Tyr Tyr Gln
    290                 295                 300

Trp Thr Leu Asn Ser Ala Asn Ile Met Asp Asp His His Phe Tyr Ile
305                 310                 315                 320

Asp Ala Met Leu Asp Ala Lys Ala Arg Val Phe Leu Leu Lys Val Gly
            325                 330                 335

Glu Leu Leu Val Lys His Gly Val Ile Gln Asp Arg Glu Asp Leu Trp
        340                 345                 350

Phe Leu Tyr Asp Asp Glu Val Glu Asn Ala Leu Leu His Pro Val Ser
    355                 360                 365

Leu Gln Glu Lys Ala Glu Lys Arg Arg Gln Ala Phe His Glu Tyr Glu
370                 375                 380

Leu Ala Lys Ala Pro Ala Tyr Leu Gly Thr Pro Thr Lys Glu Gln Leu
385                 390                 395                 400

Lys Ile Ala Glu Glu Ile Val Gly Ala Val Ile Glu Asp Glu Lys Asn
            405                 410                 415

Thr Glu Asn His Ile Phe Gly Ile Ala Ala Ser Ser Gly Ile Ala Thr
        420                 425                 430

Gly Pro Val Lys Ile Ile Arg Asp Ala Ser Glu Phe Ser Gln Phe Ala
    435                 440                 445

Ser

<210> SEQ ID NO 9
<211> LENGTH: 450
<212> TYPE: PRT
<213> ORGANISM: Bacillus vallismortis
<220> FEATURE:
<221> NAME/KEY: domain
<222> LOCATION: (1)..(450)

<400> SEQUENCE: 9

Ser Phe Met Ile Thr Asp Ala Asp Met Asn Asp Phe Trp Ile Asn Met
1               5                   10                  15

Glu Ser Asn Ile Glu Gly Pro Ile Ser Pro Leu Phe Ser Ser Ile Ile
            20                  25                  30

Val Pro Ala Met Glu Tyr Gly Leu Lys Lys Asn Met Gln Lys Phe Pro
        35                  40                  45

Ile Gly Val Val Val Asp Glu Val Lys Leu Tyr Arg Gly His Val Tyr
    50                  55                  60

Ser Lys Ser Gln Asp Gly Gln Gln Pro Gln Thr Asp Asp Cys Gly Glu
65                  70                  75                  80

Glu Leu Phe Pro Ile Leu Ser Glu Arg Met Tyr Asp Ile Ile Lys His
            85                  90                  95

Thr Tyr Leu Pro Phe Tyr Glu Thr Leu Asp Gln Leu Thr Gln Thr Asp
        100                 105                 110

His Thr Ala Glu Ser Ala Leu Asp Ala Phe Arg Lys Leu Lys Ala Phe
    115                 120                 125

Tyr Leu Thr Ala Tyr Asp Glu His Phe Asn Ile Val Phe Pro Gln Met
130                 135                 140

Leu Leu Thr Asn Lys Leu Gln Ala Met Tyr Gln His Ile Gln Gly Glu
145                 150                 155                 160
```

```
Ser Glu Asn Ala His Phe Tyr Glu Met Leu Thr Gly Lys Met Asn Lys
                165                 170                 175

Ser Leu Glu Thr Asp Arg Leu Leu Trp Leu Phe Ser Val Glu Val Gln
            180                 185                 190

Glu Asn Pro Asn Leu Leu Ser Ile Phe Lys Asn Thr Lys Pro Glu Gln
        195                 200                 205

Leu Gln Glu Lys Leu Lys Gln Thr Asp Glu Gly Lys Gln Phe Leu Arg
    210                 215                 220

Asn Ile His Glu Phe Leu Gln Glu Tyr Gly Trp Arg Ser Val Lys Ser
225                 230                 235                 240

His Asp Leu Ile Glu Gln Thr Trp Ala Glu Asn Pro Tyr Tyr Ala Leu
                245                 250                 255

Ala Asn Ile Gln Asn Tyr Val Arg Asn Gly Tyr His Phe Asp Asn Glu
            260                 265                 270

Phe Gln Lys Thr Lys Glu Lys Arg Glu Ala Leu Tyr Ser Glu Phe Leu
        275                 280                 285

Glu Asn Ile Glu Asp Pro Asn Leu Arg Lys Glu Phe Asp Arg Tyr Tyr
    290                 295                 300

Gln Trp Thr Leu Asn Ala Ala Asn Ile Met Asp Asp His His Phe Tyr
305                 310                 315                 320

Ile Asp Ala Met Leu Asp Ala Lys Ala Arg Ala Phe Leu Leu Lys Val
                325                 330                 335

Gly Glu Leu Leu Ala Glu Asn Gly Val Ile Gln Asp Arg Glu Asp Leu
            340                 345                 350

Trp Phe Leu Tyr Asp Asp Asp Val Glu Asn Ala Leu Leu His Pro Val
        355                 360                 365

Ser Leu Gln Asp Lys Ala Glu Lys Arg Arg Gln Ala Phe His Glu Tyr
    370                 375                 380

Glu Leu Ala Lys Ala Pro Ala Tyr Leu Gly Asn Pro Thr Lys Glu Gln
385                 390                 395                 400

Ile Lys Ile Ala Glu Glu Ile Val Gly Ala Val Ile Glu Asp Glu Lys
                405                 410                 415

Asn Thr Glu Asn His Ile Phe Gly Ile Ala Ala Ser Ser Gly Ile Ala
            420                 425                 430

Thr Gly Pro Val Lys Val Ile Arg Asp Ala Ser Glu Phe Ser Arg Phe
        435                 440                 445

Ala Cys
    450

<210> SEQ ID NO 10
<211> LENGTH: 449
<212> TYPE: PRT
<213> ORGANISM: Bacillus mojavensis
<220> FEATURE:
<221> NAME/KEY: domain
<222> LOCATION: (1)..(449)

<400> SEQUENCE: 10

Asn Phe Met Ile Thr Asp Lys Asp Met Asp Asp Phe Trp Leu Asn Met
1               5                   10                  15

Glu Ser Asn Ile Glu Gly Pro Val Ser Pro Leu Phe Ser Ser Phe Ile
            20                  25                  30

Val Pro Ala Leu Glu Tyr Gly Leu Lys Lys Ser Met Arg Gln Phe Pro
        35                  40                  45

Ile Gly Val Ile Val Asp Glu Val Lys Val Tyr Arg Gly His Ile Tyr
```

```
                  50                  55                  60
Ser Lys Asn Gln Gly Gly Gln Gln Leu Pro Ala Glu Asp Ser Ala Glu
 65                  70                  75                  80

Glu Leu Phe Pro Val Leu Ser Glu Arg Met Tyr Asp Ile Ile His Asn
                 85                  90                  95

Thr Tyr Leu Pro Phe Tyr Arg Thr Leu Asp Gln Leu Ala Gln Thr Glu
                100                 105                 110

His Thr Pro Glu Ser Ala Leu Asp Ala Phe Lys Lys Leu Lys Ser Phe
            115                 120                 125

Tyr Leu Thr Ala Tyr Glu Glu His Phe Asn Ile Val Phe Pro Gln Ile
            130                 135                 140

Leu Leu Thr Asn Lys Leu Gln Ala Met Tyr Gln Asn Ile Gln Gly Glu
145                 150                 155                 160

Thr Glu Asn Ser His Phe Tyr Glu Met Leu Thr Gly Val Met Asn Lys
                165                 170                 175

Ser Leu Glu Thr Asp Arg Arg Leu Trp Gln Phe Ser Val Glu Val Arg
                180                 185                 190

Glu Asn Pro Asn Leu Thr Ala Leu Phe Glu His Ala Gln Pro Glu His
            195                 200                 205

Leu Gln Glu Arg Leu Glu Gln Thr Asp Glu Gly Arg Gln Phe Leu Gln
210                 215                 220

Lys Ala Asn Glu Phe Leu Gln Glu Tyr Gly Trp Arg Ser Val Lys Ser
225                 230                 235                 240

His Asp Leu Ile Glu Gln Thr Trp Ala Glu Asn Pro Phe Tyr Ala Leu
                245                 250                 255

Thr His Ile Gln Asn Tyr Val Arg Asn Gly Tyr His Phe Asp Asn Glu
                260                 265                 270

Phe Lys Lys Thr Ile Lys Lys Arg Glu Lys Leu Tyr Asn Glu Phe Phe
            275                 280                 285

Gln Ser Ile Glu Asp Pro Ala Leu Gln Lys Glu Phe Glu Arg Tyr Tyr
            290                 295                 300

Gln Trp Thr Leu Asn Ser Ser Asn Ile Lys Asp Asp His His Phe Tyr
305                 310                 315                 320

Ile Asp Ala Met Leu Asp Ala Lys Ala Arg Val Phe Leu Leu Lys Val
                325                 330                 335

Gly Glu Leu Leu Ala Glu Ser Gly Val Ile Gln Asp Arg Glu Asp Leu
                340                 345                 350

Trp Phe Leu Tyr Asp Asp Glu Val Glu Asn Ala Leu Leu His Pro Val
            355                 360                 365

Ser Leu Gln Glu Lys Ala Glu Lys Arg Arg Gln Met Phe His Glu Tyr
            370                 375                 380

Glu Leu Ala Gln Ala Pro Ala Tyr Leu Gly Thr Pro Thr Glu Ala Gln
385                 390                 395                 400

Leu Lys Ala Ala Glu Glu Ile Val Gly Ala Val Ile Glu Asp Glu Lys
                405                 410                 415

Asn Thr Glu Asn Asp Ile Phe Gly Val Ala Ala Ser Ser Gly Ile Ala
            420                 425                 430

Thr Gly Pro Val Lys Val Ile Arg Asp Ala Ser Glu Phe Ser Gln Phe
            435                 440                 445

Thr

<210> SEQ ID NO 11
<211> LENGTH: 451
```

```
<212> TYPE: PRT
<213> ORGANISM: Bacillus atrophaeus
<220> FEATURE:
<221> NAME/KEY: domain
<222> LOCATION: (1)..(451)

<400> SEQUENCE: 11
```

| Phe | Met | Ile | Thr | Lys | Glu | Asp | Met | Asn | Asp | Phe | Trp | Leu | Asn | Met | Glu |
|---|---|---|---|---|---|---|---|---|---|---|---|---|---|---|---|
| 1 | | | | 5 | | | | | 10 | | | | | 15 | |
| Ser | Asn | Ile | Glu | Gly | Pro | Ile | Ser | Pro | Leu | Phe | Ser | Ser | Leu | Ile | Val |
| | | | 20 | | | | 25 | | | | | 30 | | | |
| Pro | Ala | Met | Glu | His | Gly | Leu | Lys | Lys | Arg | Ser | Glu | Gln | Phe | Pro | Ile |
| | | 35 | | | | 40 | | | | | 45 | | | | |
| Gly | Val | Thr | Ile | Glu | Glu | Val | Lys | Gln | Tyr | Arg | Gly | His | Ile | Tyr | Ser |
| | 50 | | | | | 55 | | | | | 60 | | | | |
| Lys | Gln | Lys | Gly | Gly | Asp | Pro | Thr | Glu | Ala | Ala | Lys | Ala | Ala | Glu | Ala |
| 65 | | | | | 70 | | | | 75 | | | | | 80 | |
| Ala | Glu | Glu | Leu | Phe | Pro | His | Leu | Ala | Glu | Arg | Met | Tyr | Gly | Ile | Leu |
| | | | | 85 | | | | | 90 | | | | | 95 | |
| Asn | Lys | Thr | Phe | Leu | Pro | Phe | Tyr | Glu | Thr | Leu | Asp | Glu | Leu | Ser | Ala |
| | | | 100 | | | | | 105 | | | | | 110 | | |
| Ala | Ser | His | Thr | Pro | Glu | Ser | Ala | Leu | Asn | Ala | Phe | Lys | Lys | Leu | Lys |
| | | | 115 | | | | | 120 | | | | | 125 | | |
| Ala | Phe | Tyr | Met | Glu | Ala | Tyr | Asp | Glu | His | Phe | Asn | Ile | Val | Phe | Pro |
| | 130 | | | | | 135 | | | | | 140 | | | | |
| Gln | Leu | Leu | Leu | Asn | Thr | Lys | Leu | Glu | Thr | Met | Tyr | Gln | Gln | Val | Gln |
| 145 | | | | | 150 | | | | 155 | | | | | 160 | |
| Gly | Asp | Thr | Glu | Asn | Ser | His | Phe | His | Glu | Met | Leu | Thr | Gly | Lys | Met |
| | | | | 165 | | | | | 170 | | | | | 175 | |
| Asn | Lys | Ser | Leu | Glu | Thr | Asp | Arg | His | Leu | Trp | Leu | Ser | Asn | Glu | |
| | | | 180 | | | | | 185 | | | | | 190 | | |
| Val | Lys | Lys | Asn | Ala | Ala | Leu | Lys | Gln | Val | Phe | Glu | Thr | His | Gln | Ala |
| | | | 195 | | | | | 200 | | | | | 205 | | |
| Glu | Glu | Leu | Gln | Glu | Thr | Leu | Ala | Gln | Thr | Ser | Asp | Gly | Lys | Leu | Phe |
| | 210 | | | | | 215 | | | | | 220 | | | | |
| Leu | Asp | Lys | Val | Asn | Glu | Phe | Leu | Arg | Glu | Tyr | Gly | Trp | Arg | Ser | Val |
| 225 | | | | | 230 | | | | 235 | | | | | 240 | |
| Lys | Ser | His | Asp | Leu | Ile | Glu | Gln | Ile | Trp | Ala | Glu | Asn | Pro | Tyr | Tyr |
| | | | | 245 | | | | | 250 | | | | | 255 | |
| Ala | Leu | Ser | His | Ile | Gln | Asn | Tyr | Val | Arg | Asn | Gly | Tyr | His | Phe | Asp |
| | | | 260 | | | | | 265 | | | | | 270 | | |
| Asn | Glu | Phe | Asn | Lys | Thr | Ile | Glu | Lys | Arg | Lys | Gln | Leu | Tyr | Asn | Glu |
| | | 275 | | | | | 280 | | | | | 285 | | | |
| Phe | Leu | Gln | Gln | Ile | Glu | Asp | Glu | Ala | Phe | Arg | Lys | Glu | Tyr | Asp | Arg |
| | 290 | | | | | 295 | | | | | 300 | | | | |
| Tyr | Tyr | Gln | Trp | Met | Leu | Asn | Ser | Ser | Val | Ile | Arg | Asp | Asp | His | His |
| 305 | | | | | 310 | | | | 315 | | | | | 320 | |
| Phe | Tyr | Ile | Asp | Ala | Met | Leu | Asp | Ala | Lys | Ala | Arg | Ile | Phe | Leu | Leu |
| | | | | 325 | | | | | 330 | | | | | 335 | |
| Arg | Ile | Gly | Glu | Met | Leu | Ala | Asp | Ser | Gly | Val | Ile | Asp | Lys | Glu | |
| | | | 340 | | | | | 345 | | | | | 350 | | |
| Asp | Leu | Trp | Tyr | Leu | Tyr | Asp | Asp | Glu | Ile | Glu | Asn | Ala | Leu | Leu | His |
| | | | | 355 | | | | | 360 | | | | | 365 | |
| Pro | Val | Pro | Leu | Gln | Ala | Lys | Thr | Ala | Lys | Arg | Arg | Glu | Val | Phe | Lys |
| | | | 370 | | | | | 375 | | | | | 380 | | |

```
Glu Tyr Glu Leu Val His Ala Pro Ser Tyr Leu Gly Ser Pro Thr Ala
385                 390                 395                 400

Glu Gln Leu Lys Ala Ala Glu Asp Ile Val Gly Ser Val Thr Glu Asp
                405                 410                 415

Glu Lys Asn Thr Glu Asp His Ile Tyr Gly Val Ala Ala Ser Ser Gly
            420                 425                 430

Ile Val Ser Gly Pro Val Lys Val Ile Arg Asp Ala Asn Glu Phe Ser
        435                 440                 445

Arg Phe Ser
    450

<210> SEQ ID NO 12
<211> LENGTH: 449
<212> TYPE: PRT
<213> ORGANISM: Bacillus amyloliquefaciens
<220> FEATURE:
<221> NAME/KEY: domain
<222> LOCATION: (1)..(449)

<400> SEQUENCE: 12

Phe Ile Met Thr Pro Arg Asp Gln Lys Asp Phe Trp Leu Asn Met Glu
1               5                   10                  15

Ser Asn Ile Glu Gly Pro Val Ser Pro Leu Phe Ala Ser Leu Ile Val
            20                  25                  30

Pro Ala Leu Glu Tyr Gly Leu Lys Glu Ser Thr Lys Thr Phe Pro Val
        35                  40                  45

Met Gly Ile Glu Ile Glu Arg Val Lys Leu His Gln Gly Arg Val Phe
    50                  55                  60

Ser Arg Gln His Lys Thr Asp Asp Glu Pro Pro Ala Glu Gln Leu Glu
65                  70                  75                  80

Ala Leu Phe Pro Ile Leu Ala Asp Arg Met Tyr Asp Ile Ile His Glu
                85                  90                  95

Thr Phe Leu Pro Phe Tyr Gln Lys Leu Asp Glu Leu Ala His Thr Asn
            100                 105                 110

His Thr Pro Glu Thr Ala Leu Asp Ala Phe Arg Asn Leu Gln Asp Phe
        115                 120                 125

Tyr Leu Lys Gly Tyr Glu Glu His Phe Asn Ile Val Phe Pro Gln Val
    130                 135                 140

Ala Leu Asn Met Met Leu Glu Ser Met Tyr Gly Gln Ile Glu Lys Glu
145                 150                 155                 160

Asn Thr Ser Leu Leu Tyr Glu Met Leu Ala Gly Val Met Asn Lys Ser
                165                 170                 175

Leu Glu Thr Asp Arg Gln Leu Trp Leu Leu Ser Gly Gln Val Lys Asp
            180                 185                 190

Ser Pro Glu Leu Arg Arg Val Phe Thr Val Ser Pro Ala Gly Glu Leu
        195                 200                 205

His Gln Thr Leu Leu Gln Ser Asn Glu Gly Lys Arg Phe Leu Glu Gln
    210                 215                 220

Val Gly Glu Phe Leu Gln Glu Tyr Gly Trp Arg Ser Val Lys Ser His
225                 230                 235                 240

Asp Leu Ile Glu Glu Thr Trp Ala Glu Asn Pro Tyr Phe Ala Leu Ala
                245                 250                 255

Asn Ile Gln Asn Tyr Val Arg Asn Gly Tyr Asp Phe Asp Ser Glu Phe
            260                 265                 270

His Lys Thr Ile Glu Lys Arg Lys Gln Leu Tyr Ala Ala Phe Met Glu
```

```
            275                 280                 285
Lys Ile Glu Asp Asp Gly Phe Arg Glu Arg Phe Asp Arg Tyr Tyr Gln
    290                 295                 300

Trp Thr Leu Ser Ser Ser Val Ile Lys Asp Asp His His Phe Tyr Ile
305                 310                 315                 320

Asp Ala Met Leu Asp Ala Lys Ala Arg Leu Cys Leu Leu Lys Ile Gly
                325                 330                 335

Glu Leu Leu Gln Lys Gln Gly Val Ile Asp Asp Arg Glu Asp Met Trp
            340                 345                 350

Tyr Leu Tyr Ser Asp Glu Val Glu Lys Ala Leu Ala Ser Pro Val Pro
        355                 360                 365

Met Gln Glu Lys Ala Ala Glu Arg Lys Gln Leu Phe Gln Gln Tyr Gln
    370                 375                 380

Leu Leu Glu Ala Pro Ala Tyr Leu Gly Thr Pro Thr Pro Glu Gln Leu
385                 390                 395                 400

Gln Ala Ala Glu Gln Ile Thr Gly Ser Ile Thr Glu Asp Glu Lys Asn
                405                 410                 415

Thr Glu His His Ile Tyr Gly Leu Ala Ala Ser Ser Gly Ile Ala Ser
            420                 425                 430

Gly Pro Val Lys Val Ile Arg Asp Ala Ser Glu Phe Ser Arg Phe Ser
        435                 440                 445

Ser

<210> SEQ ID NO 13
<211> LENGTH: 470
<212> TYPE: PRT
<213> ORGANISM: Bacillus pumilus
<220> FEATURE:
<221> NAME/KEY: domain
<222> LOCATION: (1)..(470)

<400> SEQUENCE: 13

Ala Ala Leu Ser Lys Ala Ala Asp Glu Thr Val Gly Ala Ser Phe Gln
1               5                   10                  15

Met Gln Pro Asp Glu Leu Gln Asp Phe Trp Ile Ser Met Asp Asp His
            20                  25                  30

Met Pro Gly Pro Thr Ser Pro Leu Phe Ser Ser Leu Ile Ile Pro Ala
        35                  40                  45

Leu Lys Ser Gly Met Lys Lys Asn Gly Glu Lys Tyr Gln Val Pro Asp
    50                  55                  60

Leu Asn Ile Lys Asp Ile Lys Leu Tyr Arg Gly His Leu Tyr Ser Ser
65                  70                  75                  80

Pro Ser Leu Pro Glu Ala Ser Ala Glu Ala Val Pro Val Phe Asp Glu
                85                  90                  95

Ser Leu Phe Glu Leu Phe Pro His Leu Ser Glu Arg Met Tyr Glu Ile
            100                 105                 110

Leu Glu Lys Asn Phe Phe Pro Phe Tyr Glu Lys Leu Asp Leu Lys Ile
        115                 120                 125

Lys Glu Pro Met Thr Ile Glu Glu Ala Ile Gly Phe Glu Glu Leu
    130                 135                 140

Lys Ala Phe Tyr Ile Gln Ala Tyr Asp Asp His Phe Asp Ile Val Ile
145                 150                 155                 160

Pro Gln Val Ile Leu Ser Ala Met Ile Glu Asp Met Leu Val Thr Tyr
                165                 170                 175

Thr Gly Asp Gln Ser Gln Val Ile Leu Leu His Glu Met Met Ile Gly
```

```
                      180                 185                 190
        Val Met Asn Lys Ser Leu Glu Thr Asp Lys Lys Leu Ser Asp Phe Ala
                        195                 200                 205
        Lys Ser Val Leu Gln Asp Lys Glu Leu Tyr Gln Ala Phe Ile Asn Asn
                    210                 215                 220
        Glu Lys Asn Ser Glu Leu Leu Asp Ala Leu Thr Gln Ser Glu Lys Gly
        225                 230                 235                 240
        Arg His Phe Ile Ser Thr Leu Glu Glu Phe Leu Gln Val Tyr Gly Trp
                        245                 250                 255
        Arg Ser Val Lys Ser His Asp Leu Thr Glu Glu Thr Trp Val Glu Asn
                    260                 265                 270
        Pro Glu Phe Ile Leu Asp Ile Ile Arg Ser Asn Ile Gln His Gln Ser
                275                 280                 285
        Asp Phe Asp Glu Glu Phe Ala Gln Ala Val Ile Lys Arg Gln Glu Thr
                    290                 295                 300
        Tyr Glu His Phe Met Ser Gln Val Lys Asp Glu Ala Phe Lys Thr Lys
        305                 310                 315                 320
        Phe Glu Thr Leu Tyr Gln Phe Ala Leu Gln Ala Ala Asn Ile Arg Asp
                        325                 330                 335
        Asp His His Phe Tyr Ile Asp Ala Met Leu Asp Ala Lys Ala Arg Val
                    340                 345                 350
        Tyr Leu Leu Lys Ile Gly Glu Leu Leu Val Gln Lys Gly Thr Leu Pro
                        355                 360                 365
        His Gln Glu Asp Leu Trp Tyr Leu Tyr Asp Glu Glu Val His Thr Ala
                    370                 375                 380
        Leu Thr Thr Ser Thr Ser Phe Asp Thr Val Ile Ala Gln Arg Lys Ile
        385                 390                 395                 400
        Asp Met Lys Glu Asn Glu Ala Ile Gln Pro Pro Ala Tyr Met Gly Thr
                        405                 410                 415
        Pro Thr Glu Ala Glu Leu Gln Gln Val Glu Arg Thr Leu Gly Ser Leu
                    420                 425                 430
        Arg Glu Asn Glu Asn Asn Thr Ser Asp Met Ile Tyr Gly Ile Gly Ala
                        435                 440                 445
        Ser Ser Gly Ile Val Ser Gly Arg Val Lys Val Ile Thr Cys Ala Glu
                    450                 455                 460
        Glu Phe Ser Gln Phe Gln
        465                 470

<210> SEQ ID NO 14
<211> LENGTH: 462
<212> TYPE: PRT
<213> ORGANISM: Bacillus megaterium
<220> FEATURE:
<221> NAME/KEY: domain
<222> LOCATION: (1)..(462)

<400> SEQUENCE: 14

Leu Thr Pro Phe Gln Lys Asp Ile Ser Leu Asn Phe Glu Asp Met Glu
        1               5                   10                  15
        Glu Phe Trp Ile Leu Asn Asp Thr Ser Phe Ser His Ala Val Ser Pro
                    20                  25                  30
        Leu Tyr Ala Ser Phe Ile Ile Pro Ala Phe Ser Glu Gly Thr Ala Ser
                        35                  40                  45
        Ser Phe Gln Lys Leu Asn Phe Ile Phe Lys Arg Leu Asn Leu Lys Val
                    50                  55                  60
```

-continued

Tyr Lys Gly His Ile Tyr Thr Arg Thr Glu Pro Phe Lys Gly Asp Ser
 65                  70                  75                  80

Asp Lys Arg Ser Gln Glu His Lys Glu Leu Met Glu Ser Ile Tyr Pro
             85                  90                  95

Val Leu Thr Lys Arg Met Asn Gln Ile Ile Lys Glu Gln Phe Leu Pro
            100                 105                 110

Tyr Tyr Asp Lys Leu Asp Ser Ser Thr Trp Glu Asn Leu Asn Leu Gln
            115                 120                 125

Arg Gly Lys Glu Ile Leu Gln Ser Leu Thr Asp Phe Tyr Lys Thr Ala
130                 135                 140

Tyr Asp Leu His Phe Asp Ile Val Met Pro Gln Met Ser Leu Asn Thr
145                 150                 155                 160

Ile Val Glu Glu Tyr Tyr Lys Asn Leu Thr Asn Lys Lys Ser Gly His
                165                 170                 175

Asp Val Tyr Glu Leu Leu Thr Gly Lys Met Asn Lys Ser Leu Glu Thr
            180                 185                 190

Asp Gln Gln Leu Ser Arg Leu Ala Leu Ile Val Lys Gly Asp Ala Glu
            195                 200                 205

Leu Thr Lys Ile Phe Gln Glu Glu Cys Thr Glu Thr Leu Leu Lys Lys
210                 215                 220

Leu Glu Glu Asn Lys Ala Ala Lys Ser Phe Met Ala Glu Val Asp Ala
225                 230                 235                 240

Phe Leu Lys Gln Tyr Gly Tyr Arg Ser Val Val Ser His Asp Phe Val
                245                 250                 255

Gly Glu Thr Trp Leu Glu Asn Pro Leu His Ala Leu Ser Ile Ile Gln
            260                 265                 270

Gly Tyr Val Asn Asp Gly Tyr Asn Phe Asp Glu Asn Phe Lys Gln Thr
            275                 280                 285

Val Lys Lys Arg Glu Gln Asn Tyr Asn Glu Leu Leu Met Gln Ile Glu
290                 295                 300

Asp Ser Gln His Lys Glu Glu Phe Lys Lys Tyr Tyr His Trp Ala Leu
305                 310                 315                 320

Asp Ala Ser Val Ile Arg Asp Asp His His Phe Tyr Ile Asp Ala Met
                325                 330                 335

Leu Asp Ala Lys Ala Arg Leu Phe Leu Leu Lys Leu Gly Asn Leu Leu
            340                 345                 350

Val His His His Val Phe Leu Val Lys Glu Asp Ile Phe Phe Leu Tyr
            355                 360                 365

Leu Asp Glu Leu Glu Ser Leu Leu Glu Asn Pro Val Asp Met Thr Glu
370                 375                 380

Leu Ile Glu Lys Arg Lys Lys Glu His Ala Glu His Glu Lys Met Ser
385                 390                 395                 400

Asn Leu Pro Lys Tyr Phe Gly Val Pro Glu Pro Ala Gln Leu Lys Glu
                405                 410                 415

Ala Glu Lys Tyr Met Gly Ala Ile Glu Glu Asn Asp Ala Asn Ser Glu
            420                 425                 430

His Ser Ile Lys Gly Leu Ala Ser Ser Gly Thr Tyr Thr Gly Lys
            435                 440                 445

Val Lys Val Ile Ser Asn Thr Lys Glu Phe Ser Lys Leu Glu
450                 455                 460